(12) United States Patent
Urade et al.

(10) Patent No.: US 7,951,956 B2
(45) Date of Patent: May 31, 2011

(54) BENZOIMIDAZOLE COMPOUND CAPABLE OF INHIBITING PROSTAGLANDIN D SYNTHETASE

(75) Inventors: Yoshihiro Urade, Kyoto (JP); Yoshiki Tanaka, Hanno (JP); Keiko Yamane, Hanno (JP); Michinori Togawa, Hanno (JP)

(73) Assignee: Taiho Pharmaceuticals Co., Ltd., Tokyo (JP)

( * ) Notice: Subject to any disclaimer, the term of this patent is extended or adjusted under 35 U.S.C. 154(b) by 572 days.

(21) Appl. No.: 11/995,437

(22) PCT Filed: Jul. 12, 2006

(86) PCT No.: PCT/JP2006/313827
§ 371 (c)(1),
(2), (4) Date: Jan. 11, 2008

(87) PCT Pub. No.: WO2007/007778
PCT Pub. Date: Jan. 18, 2007

(65) Prior Publication Data
US 2009/0281098 A1    Nov. 12, 2009

(30) Foreign Application Priority Data

Jul. 13, 2005   (JP) ................................ 2005-204957
Sep. 22, 2005   (JP) ................................ 2005-275919

(51) Int. Cl.
*A61K 31/4184* (2006.01)
*C07D 403/04* (2006.01)
*C07D 407/04* (2006.01)

(52) U.S. Cl. ................... 548/306.1; 548/304.7; 514/394

(58) Field of Classification Search .............. 548/306.1, 548/304.7
See application file for complete search history.

(56) References Cited

FOREIGN PATENT DOCUMENTS

| GB | 1113808 A | 5/1968 |
|---|---|---|
| JP | 2000-026430 A | 1/2000 |
| JP | 2004-002248 A | 1/2004 |
| JP | 2004-051600 A | 2/2004 |
| JP | 2004-067629 A | 3/2004 |
| WO | WO 98/39343 A1 | 9/1998 |
| WO | WO 99/65886 A1 | 12/1999 |
| WO | WO 02/076454 A1 | 10/2002 |
| WO | WO 03/035065 A1 | 5/2003 |
| WO | WO 2004/017963 A1 | 3/2004 |
| WO | WO 2005/054232 A1 | 6/2005 |
| WO | WO 2006/034418 A2 | 3/2006 |

OTHER PUBLICATIONS

Thompson et al., Current Medicinal Chemistry, Oct. 2002, 9(19), pp. 1751-1762.*

Lee et al., Traceless solid-phase synthesis of 5-benzoylbenzimidazoles, *Canadian Journal of Chemistry*, 2001, vol. 79, No. 11, pp. 1556-1561, table 1.

Lewis et al., "Prostaglandin $D_2$ Generation After Activation of Rat and Human Mast Cells with Anti-IgE[1]", The Journal of Immunology, vol. 129, No. 4, Oct. 1982, pp. 1627-1631.

Murray et al., "Release of Prostaglandin $D_2$ into Human Airways During Acute Antigen Challenge", The New England Journal of Medicine, vol. 315, No. 13, Sep. 25, 1986, pp. 800-804.

Hardy et al., "The Bronchoconstrictor Effect of Inhaled Prostaglandin $D_2$ in Normal and Asthmatic Men", The New England Journal of Medicine, vol. 311, Jul. 26, 1984, No. 4, pp. 209-213.

Nantel et al., "Expression of prostaglandin D synthase and the prostaglandin $D_2$ receptors DP and CRTH2 in human nasal mucosa", Prostaglandins & Other Lipid Mediators, vol. 73 (2004), pp. 87-101.

Iwasaki et al., "Association of a New-Type Prostaglandin $D_2$ Receptor CRTH2 with Circulating T Helper 2 Cells in Patients with Atopic Dermatitis", The Journal of Investigative Dermatology, vol. 119, No. 3 (2002), pp. 609-616.

Urade et al., "The Major Source of Endogenous Prostaglandin $D_2$ Production is Likely Antigen-Presenting Cells", The Journal of Immunology, vol. 143, No. 9, Nov. 1, 1989, pp. 2982-2989.

Urade et al., "Mast Cells Contain Spleen-type Prostaglandin D Synthetase", The Journal of Biological Chemistry, vol. 265, No. 1, Issue of Jan. 5, pp. 371-375, 1990.

Murakami et al., "c-Kit Ligand Mediates Increased Expression of Cytosolic Phospholipase $A_2$, Prostaglandin Endoperoxide Synthase-1, . . . ", The Journal of Biological Chemistry, vol. 270, No. 7, Issue of Feb. 17, pp. 3239-3246, 1995.

(Continued)

*Primary Examiner* — Laura L. Stockton
(74) *Attorney, Agent, or Firm* — Rothwell, Figg, Ernst & Manbeck, P.C.

(57) ABSTRACT

The present invention provides a benzimidazole compound represented by Formula (I)

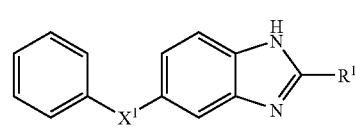

(I)

wherein $X^1$ is oxygen or carbonyl, and $R^1$ is a furan ring having 1 to 3 substituents or a pyrrole ring that may have 1 to 3 substituents; excluding compounds represented by Formula (I) wherein at least one of the substituents is a phosphoric acid group or a phosphoric ester group; or a salt thereof. The benzimidazole compound or salt thereof has excellent prostaglandin synthase inhibitory activity, and is useful as an agent for preventing and/or treating diseases in which prostaglandin D2 or metabolites thereof participates, such as allergic and inflammatory diseases, and as inhibitor for the exacerbation of Alzheimer's disease or cerebral damage.

12 Claims, No Drawings

OTHER PUBLICATIONS

Fujitani et al., "Pronounced Eosinophilic Lung Inflammation and Th2 Cytokine Release in Human Lipocalin-Type Prostaglandin D Synthase Transgenic Mice", The American Associate of Immunologists, vol. 168, pp. 443-449 (2002).

Matsuoka et al., "Prostaglandin $D_2$ as a Mediator of Allergic Asthma", Science, vol. 287, Mar. 17, 2000, pp. 2013-2017.

Matsushita et al., "Pharmacological Studies on the Novel Antiallergic Drug HQL-79: I. Antiallergic and Antiasthmatic Effects in Various Experimental Models", Jpn. J. Pharmacol, vol. 78, pp. 1-10, (1998).

Matsushita et al., "Pharmacological Studies on the Novel Antiallergic Drug HQL-79: II. Elucidation of Mechanisms for Antiallergic and Antiasthmatic Effects", Jpn. J. Pharmacol. vol. 78, pp. 11-22, (1998).

Ito Yoshiki et al., "Allergic Diseases—Diagnosis and Treatment, Based on Guideline—Therapeutics for Allergic Diseases and Current Status . . .", Japanese Journal of Clinical and Experimental Medicine, 2001, vol. 79, No. 2, pp. 218-221 with abstract.

* cited by examiner

BENZOIMIDAZOLE COMPOUND CAPABLE OF INHIBITING PROSTAGLANDIN D SYNTHETASE

CROSS REFERENCE TO RELATED APPLICATION

This application is a 35 U.S.C. 371 National Phase Entry Application from PCT/JP2006/313827, filed Jul. 12, 2006, which claims the benefit of Japanese Patent Application Nos. 2005-204957 filed on Jul. 13, 2005 and 2005-275919 filed Sep. 22, 2005, the disclosures of which are incorporated herein in its entirety by reference.

TECHNICAL FIELD

The present invention relates to a pharmaceutical agent having a novel benzimidazole compound or a salt thereof as an active ingredient, and in particular, to a pharmaceutical agent having a novel benzimidazole compound or a salt thereof as an active ingredient useful for the prevention and/or treatment of allergic and inflammatory diseases, and as inhibitor for exacerbation of Alzheimer's disease or cerebral damage, due to its prostaglandin D synthase inhibitory activity.

BACKGROUND OF THE INVENTION

A series of lipid mediators named eicosanoids, such as prostaglandins and leukotrienes, can be generically synthesized by the arachidonic acid cascade starting from arachidonic acid which is cleaved by various stimuli from membranous phospholipids. In particular, prostanoids are a type of arachidonic acid metabolites synthesized with prostaglandin H2, as an intermediate generated by cyclooxygenase in the arachidonic acid. It is known that prostaglandin D2, prostaglandin E2, prostaglandin F2α, prostaglandin I2, and thromboxane A2, are also synthesized by such a biosynthetic pathway.

Prostanoids act as locally chemical transmitters like active hormones, and are generally synthesized in response to stimuli such as local tissue damage, hormones, bacterial peptides, antigens, and inflammatory mediators such as cytokines. These prostanoids manifest various effects in different tissues by binding to specific receptors on cell surfaces. In addition to regulating gastric acid secretion and blood flow, they are known to have considerable influence on inflammatory responses and immune system in the body.

Synthases that generate prostaglandin D2 are referred to as prostaglandin D synthases. It is known that two different types, hematopoietic and lipocalin-type synthase are existed.

Human hematopoietic synthases are distributed throughout the placenta, lung, fetus liver, lymphonodus, brain, heart, thymus, bone marrow, and spleen. Moreover, at the cellular level, they are reported to be expressed in microneuroglia in the brain, megakaryocytes and Langerhans cells in the skin; Kupffer cells in the liver; macrophages; and many antigen-presenting cells, such as dendritic cells, mast cells, and Th2 cells.

On the other hand, lipocalin-type synthases are distributed mainly in the central nervous system of the brain and spinal cord, the heart, the testis epithelium, and testis. It is known that not only does the prostaglandin D2 produced by lipocalin-type synthase act as a humoral regulator of sleep, and mediator of cranial nerve system control via the arachnoid membrane, nociception control as typified by allodynia, and spermatogenesis control, but also that lipocalin-type enzymes themselves have a function as transporter proteins of lipophilic low-molecular-weight compounds.

Two types of specific receptors of prostaglandin D2, DP1 and DP2 (also referred to as CRTH2), are known. It is reported that DP1 is expressed in tissues such as bone marrow, brain, retina and digestive organs, respiratory epithelial cells, vascular smooth muscle, platelets and cells such as basophils, while DP2 is expressed in tissues such as bone marrow, brain, thymus and heart, Th2 cells, and eosinophils, basophils and monocytes. The prostaglandin D2 mainly produced locally by hematopoietic synthases due to various stimuli, that binds with these receptors, has various actions such as inhibition of platelet aggregation, vasodilation, enhancement of vascular permeability, increased mucus production, airway smooth muscle contraction, and mobilization and activation of antigen-presenting cells, Th2 cells, and eosinophils. In particular, it is thought to participate in the onset and exacerbation of allergic diseases and inflammatory diseases.

In allergic diseases, such as bronchial asthma and allergic rhinitis, mast cells are activated by the binding of antigens with immunogloblin E, thereafter various inflammatory mediators are produced by the activation of an arachidonic acid cascade, which is thought to play an important role in elucidation of allergic reactions. Among these, prostaglandin D2 is the inflammatory mediator produced in the largest amounts, and it is detected at high concentration in an asthmatic's bronchoalveolar fluid (Non-patent documents 1 and 2). Further, it was reported that bronchoconstriction was simultaneously induced by prostaglandin D2 inhalation in asthmatic patients but not healthy subjects (Non-patent document 3). Moreover, from the facts that hematopoietic synthases are highly expressed in mast cells or inflammatory cells at nasal mucosa in allergic rhinitis, or nasal polyps in chronic sinusitis, DP1 and DP2 are also expressed in the infiltrated eosinophils, and DP2 is expressed in T cells (Non-patent document 4), and that in atopic dermatitis the proportion of DP2 positive skin lymphocyte homing antigen-positive cells (CLA) is high depending on the severity of symptoms (Non-patent document 5), it is thought that prostaglandin D2 produced by hematopoietic enzyme plays an important role in the onset and exacerbation of allergic diseases (Non-patent documents 6-8).

Recently, it has been reported that in prostaglandin D synthase transgenic mice, allergic responses were promoted (Non-patent document 9), whereas prostaglandin D2 receptor-knockout mice did not show allergic responses (Non-patent document 10). It was also reported that in hematopoietic synthase-deficient mice, the expansion of myonecrosis or traumatic cerebral damage is also minor.

Therefore, the prostaglandin D2 produced by these two types of enzymes, hematopoietic synthases and lipocalin-type synthases, participates in the onset and exacerbation of various diseases including allergy, and in the regulatory mechanisms of the body, so pharmaceutical preparations that can ameliorate excess production are considered to be very effective in the treatment of various diseases.

For example, as a hematopoietic synthase inhibitor, HQL-79 (4-benzhydryloxy-1-((3-(1H-tetrazol-5-yl)-propyl))piperidine) has been reported (Non-patent documents 11 and 12). Although HQL-79 is a compound having histamine H1 receptor antagonistic activity, is reported to inhibit airway inflammation such as suppression of eosinophil infiltration into the airway and the delayed asthmatic response in experimental asthmatic models, it cannot be said to have sufficient activity. Another prostaglandin D synthase inhibitor has been disclosed (Patent documents 8 and 9), and its enzyme inhibitory activity exceeds that of HQL-79, but it also does not have sufficient activity.

Anti-allergic agents currently used to prevent or treat allergic disorders include antihistamines, chemical mediator release inhibitors, leukotriene receptor antagonists, thromboxane-A2 synthesis inhibitors and receptor antagonists, Th2 cytokine inhibitors, and immunosuppressants (Non-patent document 13). However, these anti-allergic drugs cannot be said to have sufficient medicinal action, and since some of them have side-effects on the central nervous system, such as sleepiness and drowsiness; or cause digestive symptoms such as diarrhea; or cause immunosuppression; they have problematic issues and not easy to use. Moreover, although steroids are often employed for the treatment not only for allergic diseases but also for many inflammatory diseases due to their powerful anti-inflammatory action, they may lead to a higher susceptibility to infection, have an adverse effect on bone, interfere with growth, and also cause a rebound phenomenon after their use is discontinued, so they also are not easy to use.

On the other hand, it may be expected that a inhibitor of prostaglandin D synthase would be a useful drug in the prevention and/or treatment of allergic or inflammatory diseases in which prostaglandin D2 produced by hematopoietic synthase or their metabolites are involved.

Conventionally, benzimidazole compounds have been widely studied as useful pharmacological agents.

For example, in Patent document 1 (International Publication WO No. 2004017963), a wide range of benzimidazole compounds including 5-phenoxy benzimidazole) are described as blood coagulation factor Xa inhibitors.

In Patent document 2 (JP-A 2004-067629), a 5-phenoxybenzimidazole compound and 5-benzoylbenzimidazole compound are described as mitochondrion functional activators.

In Patent document 3 (International Publication WO No. 2003035065), a wide range of benzimidazole compounds including a 5-phenoxybenzimidazole compound and 5-benzoylbenzimidazole compound are described as protein kinase inhibitors.

In Patent document 4 (Patent No. 2001-515482), a 5-phenoxybenzimidazole compound and 5-benzoylbenzimidazole compound are described as FBP-ase inhibitors.

In Patent document 5 (International Publication WO No. 2002076454), a 5-phenoxybenzimidazole compound and 5-benzoylbenzimidazole compound are described as pharmaceutical applications of an antitumor agent.

In Patent document 6 (JP-A 2000-026430), a 5-phenoxybenzimidazole compound is described wherein pyridyl, furyl, and thienyl are substituents at position 2 of the benzimidazole.

In Patent document 7 (International Publication WO No. 9965886), a 5-benzoylbenzimidazole compound is described as an insect and mite repellent, wherein a thiazolyl group is disclosed as the heterocyclic ring of the substituent at position 2 of the benzimidazole.

Patent document 1: International Publication No. WO 2004017963
Patent document 2: Japanese Unexamined Patent Publication No. 2004-067629
Patent document 3: International Publication No. WO 2003035065
Patent document 4: Japanese Unexamined Patent Publication No. 2001-515482
Patent document 5: International Publication No. WO 2002076454
Patent document 6: Japanese Unexamined Patent Publication No. 2000-026430
Patent document 7: International Publication No. WO 9965886
Patent document 8: Japanese Unexamined Patent Publication No. 2004-2248
Patent document 9: Japanese Unexamined Patent Publication No. 2004-51600
Non-patent document 1: J. Immumol., 129, 1627-1631 (1982)
Non-patent document 2: N. Eng. J. Med., 315, 800-804 (1986)
Non-patent document 3: N. Eng., J. Med., 311, 209-213 (1984)
Non-patent document 4: Prostaglandins & Other Lipid, Med. 73, 87-101 (2004)
Non-patent document 5: J. Invest. Dermatol. 119, 609-616 (2002)
Non-patent document 6: J. Immunol., 143, 2982-2989 (1989)
Non-patent document 7: J. Biol. Chem., 265, 371-375 (1990)
Non-patent document 8: J. Biol. Chem., 270, 3239-3246 (1995)
Non-patent document 9: J. Immunol., 168, 443-449 (2002)
Non-patent document 10: Science, 287, 2013-2017 (2000)
Non-patent document 11: Jpn. J. Pharmacol., 78, 1-10 (1998)
Non-patent document 12: Jpn. J. Pharmacol., 78, 11-22 (1998)
Non-patent document 13: "Rinsho to Kenkyu (Japanese Journal of Clinical and Experimental Medicine)", vol. 79, No. 2, pp. 30-33 (February, 2002)

DISCLOSURE OF THE INVENTION

Problems to be Solved by the Invention

The main object of the present invention is to provide a novel compound that exhibits, at a low dose, a high inhibitory effect on prostaglandin D synthases, and in particular on hematopoietic prostaglandin D synthases.

Another object of the present invention is to provide a medicine with few side effects and high safety, the medicine being effective, due to its prostaglandin synthase inhibitory action, in preventing and/or treating diseases mediated by prostaglandin D2, which is generated by a prostaglandin D synthase, or metabolites thereof.

Means for Solving the Problems

The present inventors conducted extensive research on compounds having prostaglandin D synthase inhibitory activity, and found that a novel benzimidazole compound represented by Formula (I) and salts thereof have an extremely excellent inhibitory action on prostaglandin D synthases. The inventors conducted further research and have accomplished the present invention.

The present invention provides a novel benzimidazole compound represented by Formula (I) or a salt thereof; a prostaglandin D synthase inhibitor containing the compound or salt as an active ingredient; a method for preventing or treating a disease in which prostaglandin D2 or a metabolite thereof participates.

Item 1. A benzimidazole compound represented by Formula (I)

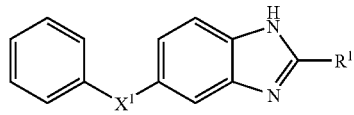

wherein $X^1$ is oxygen or carbonyl, and $R^1$ is a furan ring having 1 to 3 substituents or a pyrrole ring that may have 1 to 3 substituents;
excluding compounds represented by Formula (I) wherein at least one of the substituents is a phosphoric acid group or a phosphoric ester group;
or a salt thereof.

Item 2. The benzimidazole compound or salt thereof according to item 1, wherein $X^1$ is carbonyl.

Item 3. The benzimidazole compound or salt thereof according to item 1, wherein:
$X^1$ is oxygen or carbonyl;
$R^1$ is a furan ring having 1 to 3 substituents or a pyrrole ring that may have 1 to 3 substituents, and
the substituents on the pyrrole ring or furan ring are selected from the group consisting of halogen, cyano, nitro, $C_{1-6}$ alkyl that may have one or more substituents, $C_{3-7}$ cycloalkyl that may have one or more substituents, $C_{2-6}$ alkenyl that may have one or more substituents, and —(C=O)—$R^2$;
$R^2$ is hydrogen, hydroxy, $C_{1-6}$ alkyl that may have one or more substituents, $C_{1-6}$ alkoxy that may have one or more substituents, or —$NR^3R^4$; and
$R^3$ and $R^4$ are the same or different, and are each hydrogen, hydroxy, $C_{1-6}$ alkyl that may have one or more substituents, $C_{1-6}$ alkoxy that may have one or more substituents, amino, mono- or di($C_1$-$C_6$ alkyl)amino that may have one or more substituents, $C_{6-14}$ aryl that may have one or more substituents, or a saturated or unsaturated heterocyclic group that may have one or more substituents, or
$R^3$ and $R^4$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom [the cyclic amino group may have one or more substituents.

Item 4. The benzimidazole compound or salt thereof according to item 1, wherein:
$X^1$ is carbonyl;
$R^1$ is a furan ring having 1 to 3 substituents or a pyrrole ring that may have 1 to 3 substituents, and
the substituents on the pyrrole ring or furan ring are each halogen, cyano, nitro, $C_{1-6}$ alkyl that may have 1 to 3 substituents selected from the group consisting of halogen, hydroxy, and —$NR^{3'}R^{4'}$, $C_{2-6}$ alkenyl that may have 1 to 3 substituents selected from the group consisting of cyano, carboxy, and ($C_1$-$C_6$ alkoxy)carbonyl, or —(C=O)—$R^2$;
$R^2$ is hydrogen, hydroxy, $C_{1-6}$ alkoxy, or —$NR^3R^4$;
$R^{3'}$ and $R^{4'}$ are the same or different, and are each hydrogen or $C_{1-6}$ alkyl, or
$R^{3'}$ and $R^{4'}$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom; and one of $R^3$ and $R^4$ is hydrogen or $C_{1-6}$ alkyl, and the other is hydrogen, hydroxy, $C_{1-6}$ alkyl that may have one or more substituents, $C_{1-6}$ alkoxy that may have one or more substituents, amino, mono- or di($C_1$-$C_6$ alkyl)amino that may have one or more substituents, $C_{6-14}$ aryl that may have one or more substituents, or a monocyclic or bicyclic, saturated or unsaturated heterocyclic group that may have one or more substituents, or
$R^3$ and $R^4$, taken together with the adjacent nitrogen atom, may form a saturated or unsaturated cyclic amino group that may have, in the ring structure, one heteroatom selected from the group consisting of nitrogen, oxygen, and sulfur, in addition to the adjacent nitrogen atom, the cyclic amino group optionally having 1 to 3 substituents selected from the group consisting of halogen, hydroxy, cyano, nitro, formyl, carboxy, $C_{1-6}$ alkyl that may have one or more substituents, $C_{6-14}$ aryl that may have one or more substituents, ($C_1$-$C_6$ alkoxy)carbonyl that may have one or more substituents, and mono- or di($C_1$-$C_6$ alkyl)aminocarbonyl that may have one or more substituents.

Item 5. The benzimidazole compound or salt thereof according to item 1, wherein:
$X^1$ is carbonyl;
$R^1$ is a furan ring having 1 to 3 substituents or a pyrrole ring having 1 to 3 substituents as well as a hydrogen atom bonded to the nitrogen atom, and
the substituents attached to the pyrrole ring or furan ring are selected from the group consisting of halogen, cyano, nitro, $C_{1-6}$ alkyl that may have one or more substituents selected from the group consisting of halogen, hydroxy, dimethylamino, and pyrrolidinyl, ethenyl that may have one substituent selected from the group consisting of cyano, carboxy, and ($C_1$-$C_6$ alkoxy)carbonyl, and —(C=O)—$R^2$;
$R^2$ is hydrogen, hydroxy, $C_{1-6}$ alkoxy, or —$NR^3R^4$; and
one of $R^3$ and $R^4$ is hydrogen or $C_{1-6}$ alkyl, and the other is hydrogen, hydroxy, $C_{1-3}$ alkyl that may have one or more substituents, $C_{1-3}$ alkoxy that may have one or more substituents, phenyl that may have one or more substituents, or a heterocyclic group selected from the group consisting of morpholino, isoxazolyl, indolyl, methylenedioxyphenyl, ethylenedioxyphenyl, dihydrobenzofuranyl, and benzothiazolyl [the heterocyclic group may have one or more substituents], or
$R^3$ and $R^4$, taken together with the adjacent nitrogen atom, may form a saturated or unsaturated cyclic amino group that may have, in the ring structure, one heteroatom selected from nitrogen and oxygen, in addition to the adjacent nitrogen atom.

Item 6. The benzimidazole compound or salt thereof according to item 1, wherein:
$X^1$ is carbonyl;
$R^1$ is a furan ring having 2 or 3 substituents or a pyrrole ring having 2 or 3 substituents as well as a hydrogen atom bonded to the nitrogen atom, the substituents on two carbon atoms of the furan ring or pyrrole ring being $C_{1-6}$ alkyl, and the remaining carbon atom having a hydrogen atom bonded thereto or cyano or —(C=O)—$R^2$ as a substituent bonded thereto;
$R^2$ is hydroxy, $C_{1-3}$ alkoxy, or —$NR^3R^4$; and
one of $R^3$ and $R^4$ is hydrogen or $C_{1-3}$ alkyl, and the other is hydrogen, hydroxy, $C_{1-3}$ alkyl that may have one or more substituents, $C_{1-3}$ alkoxy that may have one or more substituents, phenyl that may have 1 to 3 substituents selected from the group consisting of halogen, cyano, and $C_{1-6}$ alkoxy, morpholino, isoxazolyl, indolyl, methylenedioxyphenyl, ethylenedioxyphenyl, dihydrobenzofuranyl, or benzothiazolyl, or —$NR^3R^4$ is pyrrolidinyl, thiazolidinyl, pyrazolinyl, morpholino, or piperazinyl.

Item 7. The benzimidazole compound or salt thereof according to item 1, wherein:

$X^1$ is carbonyl;

$R^1$ is a furan ring that has three substituents and that is attached to the benzimidazole ring at the 4-position, or a pyrrole ring that has three substituents as well as a hydrogen atom bonded to the nitrogen atom and that is attached to the benzimidazole ring at the 4-position, and of the substituents on the furan ring or pyrrole ring, substituents at the 3- and the 5-positions are $C_{1-3}$ alkyl, and the substituent at the 2-position is cyano or —(C=O)—$R^2$;

$R^2$ is hydroxy, ethoxy, or —$NR^3R^4$; and one of $R^3$ and $R^4$ is hydrogen or $C_{1-3}$ alkyl, and the other is hydrogen, hydroxy, $C_{1-3}$ alkyl that may have one or more substituents, $C_{1-3}$ alkoxy that may have one or more substituents, or phenyl that may have 1 to 3 substituents selected from the group consisting of halogen, cyano, and $C_{1-3}$ alkoxy, or —$NR^3R^4$ is pyrrolidinyl, pyrazolinyl, or morpholino.

Item 8. The benzimidazole compound or salt thereof according to item 1, wherein:

$X^1$ is carbonyl;

$R^1$ is a pyrrole ring that has three substituents, as well as a hydrogen atom bonded to the nitrogen atom, and that is attached to the benzimidazole ring at the 4-position, and of the substituents on the pyrrole ring, the substituents at the 3- and 5-positions are methyl, and the substituent at the 2-position is —(C=O)—$R^2$;

$R^2$ is hydroxy, ethoxy, or —$NR^3R^4$; and one of $R^3$ and $R^4$ is hydrogen or $C_{1-3}$ alkyl, and the other is $C_{1-3}$ alkyl that may have one or more substituents, or $C_{1-3}$ alkoxy, or —$NR^3R^4$ is pyrrolidinyl or morpholino.

Item 9. The benzimidazole compound or salt thereof according to item 1, which is:

(4-(5-benzoylbenzimidazol-2-yl)-3,5-dimethyl-2-furanyl-carbonyl)pyrrolidine, 4-(5-benzoylbenzimidazol-2-yl)-3,5-dimethylpyrrole-2-carboxylic acid, 2-(2-cyano-3,5-dimethyl-pyrrol-4-yl)-5-benzoylbenzimidazole, N-(methoxy)-4-(5-benzoylbenzimidazol-2-yl)-3,5-dimethylpyrrole-2-carboxamide, (N-methoxy-N-methyl)-4-(5-benzoylbenzimidazol-2-yl)-3,5-dimethylpyrrole-2-carboxamide, N-(3-dimethylaminopropyl)-4-(5-benzoylbenzimidazol-2-yl)-3,5-dimethylpyrrole-2-carboxamide, N-(2-(2-pyridyl)ethyl)-4-(5-benzoylbenzimidazol-2-yl)-3,5-dimethylpyrrole-2-carboxamide, ((4-(5-benzoylbenzimidazol-2-yl)-3,5-dimethylpyrrol-2-yl)carbonyl)morpholine, ((4-(5-benzoylbenzimidazol-2-yl)-3,5-dimethylpyrrol-2-yl)carbonyl)pyrazoline, or (N,N-dimethyl)-4-(5-benzoylbenzimidazol-2-yl)-3,5-dimethylpyrrole-2-carboxamide.

Item 10. A pharmaceutical composition comprising an effective amount of at least one of the compounds according to items 1 to 9 and pharmaceutically acceptable salts thereof, and a pharmaceutically acceptable carrier.

Item 11. A prostaglandin D synthase inhibitor comprising an effective amount of at least one of the compounds according to items 1 to 9 and pharmaceutically acceptable salts thereof, and a pharmaceutically acceptable carrier.

Item 12. An agent for preventing and/or treating a disease in which prostaglandin D2 or a metabolite thereof participates, the agent comprising an effective amount of at least one of the compounds according to items 1 to 9 and pharmaceutically acceptable salts thereof, and a pharmaceutically acceptable carrier.

Item 13. The agent according to item 12, wherein the disease in which prostaglandin D2 or a metabolite thereof participates is allergic and inflammatory disease, Alzheimer's disease, or cerebral damage.

Item 14. An agent for preventing and/or treating allergic diseases, the agent comprising an effective amount of a compound according to any one of items 1 to 9 or a pharmaceutically acceptable salt thereof, and a pharmaceutically acceptable carrier.

Item 15. An agent for preventing and/or treating an inflammatory disease, the agent comprising an effective amount of a compound according to any one of items 1 to 9 or a pharmaceutically acceptable salt thereof, and a pharmaceutically acceptable carrier.

Item 16. An agent for preventing and/or treating Alzheimer's disease or cerebral damage, the agent comprising an effective amount of a compound according to any one of items 1 to 9 or a pharmaceutically acceptable salt thereof, and a pharmaceutically acceptable carrier.

Item 17. A method for preventing or treating a disease in which prostaglandin D2 or a metabolite thereof participates, the method comprising administering, to a patient, an effective amount of a compound according to any one of items 1 to 9 or a pharmaceutically acceptable salt thereof.

Item 18. Use of a compound according to any one of items 1 to 9 or a pharmaceutically acceptable salt thereof, for producing a prostaglandin D synthase inhibitor.

Effects of the Invention

The present invention provides a novel benzimidazole compound represented by the above Formula (I) or a salt thereof, which is useful as a prostaglandin D synthase inhibitor, and in particular a hematopoietic synthase inhibitor.

The benzimidazole compound or salt thereof according to the present invention has excellent prostaglandin D synthase inhibitory activity, and has higher inhibitory activity against hematopoietic prostaglandin D synthases, than, for example, HQL-79, which is a known hematopoietic enzyme inhibitor (see Experiment 1 given below).

Thus, based on its excellent prostaglandin D synthase inhibitory activity, the benzimidazole compound or salt thereof according to the present invention is useful as an agent for preventing and/or treating a disease in which prostaglandin D2 or a metabolite thereof participates, such as allergic or an inflammatory disease, and as an exacerbation inhibitor for Alzheimer's disease or cerebral damage, and is expected to have other useful effects.

BEST MODE FOR CARRYING OUT THE INVENTION

Benzimidazole Compound of the Present Invention

The benzimidazole compound of the present invention is a compound represented by Formula (I).

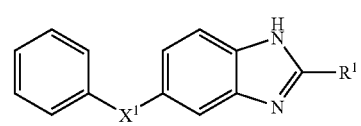

(I)

wherein $X^1$ is oxygen or carbonyl, $R^1$ is a furan ring having one or more substituents or a pyrrole ring that may have one or more substituents, and in particular, $R^1$ is a furan ring having 1 to 3 substituents or a pyrrole ring that may have 1 to 3 substituents;

excluding compounds represented by Formula (I) wherein at least one of the substituents is a phosphoric acid group or a phosphoric ester group.

The benzimidazole compound of the present invention, which is represented by Formula (I), is a novel compound and is not specifically disclosed in the above-mentioned documents.

For example, Patent document 1 (International Publication No. WO 2004017963) describes a wide range of benzimidazole compounds including a 5-phenoxybenzimidazole compound, as blood coagulation factor Xa inhibitors, but does not specifically disclose the benzimidazole compound of the present invention, which has a pyrrole ring or furan ring as a substituent at the 2-position of the benzimidazole.

Patent document 2 (Japanese Unexamined Patent Publication No. 2004-067629) describes a 5-phenoxybenzimidazole compound and a 5-benzoylbenzimidazole compound as mitochondrial functional activators. However, the compounds described in Patent document 2 have phenyl, pyridyl, or the like, as a substituent at the 2-position of the benzimidazole, and thus are different from the compound of the present invention, which has a pyrrole ring or furan ring as a substituent at the 2-position of the benzimidazole.

Patent document 3 (International Publication No. WO 2003035065) describes a wide range of benzimidazole compounds including a 5-phenoxybenzimidazole compound and a 5-benzoylbenzimidazole compound, as protein kinase inhibitors. However, Patent document 3 does not specifically disclose the benzimidazole compound of the present invention, which has a pyrrole ring or furan ring as a substituent at the 2-position of the benzimidazole.

Patent document 4 (Japanese Unexamined Patent Publication No. 2001-515482) describes a 5-phenoxybenzimidazole compound and a 5-benzoylbenzimidazole compound as FBPase inhibitors. However, the compounds described in Patent document 4 are different from the compound of the present invention since the disclosed compounds have a phosphoric acid group or a phosphoric ester group as a substituent on the furyl group at the 2-position of the benzimidazole.

Patent document 5 (International Publication No. WO 2002076454) describes pharmaceutical applications of a 5-phenoxybenzimidazole compound and a 5-benzoylbenzimidazole compound as antitumor agents, but does not specifically disclose the benzimidazole compound of the present invention, which has a pyrrole ring or furan ring as a substituent at the 2-position of the benzimidazole.

Patent document 6 (Japanese Unexamined Patent Publication No. 2000-026430) describes a 5-phenoxybenzimidazole compound, and claims pyridyl, furyl, and thienyl as substituents at the 2-position of the benzimidazole. However, the compound of Patent document 6 has a substituent at the 6-position of the benzimidazole, and in this regard, is different from the compound of the present invention, which does not have a substituent at the 6-position of the benzimidazole.

Patent document 7 (International Publication No. WO 9965886) describes a 5-benzoylbenzimidazole compound as an insect and mite repellent, and discloses a thiazolyl group as a heterocyclic ring of the substituent at the 2-position of the benzimidazole. The compound described in Patent document 7 is different from the compound of the present invention, since the compound of the present invention has a pyrrole ring or furan ring as a substituent at the 2-position of the benzimidazole.

The compound represented by Formula (I) is described below in further detail.

Of the compounds of the present invention, Compound (I) in which $X^1$ is carbonyl is preferable.

The compound of the present invention is typically a benzimidazole compound represented by Formula (I) wherein:

$X^1$ is oxygen or carbonyl;

$R^1$ is a furan ring having 1 to 3 substituents or a pyrrole ring that may have 1 to 3 substituents, and the substituents on the furan ring or pyrrole ring are selected from the group consisting of halogen, cyano, nitro, $C_{1-6}$ alkyl that may have one or more substituents, $C_{3-7}$ cycloalkyl that may have one or more substituents, $C_{2-6}$ alkenyl that may have one or more substituents, and —(C=O)—$R^2$;

$R^2$ is hydrogen, hydroxy, $C_{1-6}$ alkyl that may have one or more substituents, $C_{1-6}$ alkoxy that may have one or more substituents, or —$NR^3R^4$; and $R^3$ and $R^4$ are the same or different, and are each hydrogen, hydroxy, $C_{1-6}$ alkyl that may have one or more substituents, $C_{1-6}$ alkoxy that may have one or more substituents, amino, mono- or di($C_1$-$C_6$ alkyl)amino that may have one or more substituents, $C_{6-14}$ aryl that may have one or more substituents, or a saturated or unsaturated heterocyclic group that may have one or more substituents, or $R^3$ and $R^4$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom [the cyclic amino group may have one or more substituents].

Specifically, one embodiment of the present invention provides a benzimidazole compound represented by Formula (I) wherein:

$X^1$ is carbonyl;

$R^1$ is a furan ring having 1 to 3 substituents or a pyrrole ring that may have 1 to 3 substituents, and the substituents on the pyrrole ring or furan ring are each halogen, cyano, nitro, $C_{1-6}$ alkyl that may have 1 to 3 substituents selected from the group consisting of halogen, hydroxy, and —$NR^{3'}R^{4'}$, $C_{2-6}$ alkenyl that may have 1 to 3 substituents selected from the group consisting of cyano, carboxy, and ($C_1$-$C_6$ alkoxy)carbonyl, or —(C=O)—$R^2$;

$R^2$ is hydrogen, hydroxy, $C_{1-6}$ alkoxy, or —$NR^3R^4$;

$R^{3'}$ and $R^{4'}$ are the same or different, and are each hydrogen or $C_{1-6}$ alkyl, or $R^3$ and $R^4$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom; and one of $R^3$ and $R^4$ is hydrogen or $C_{1-6}$ alkyl, and the other is hydrogen, hydroxy, $C_{1-6}$ alkyl that may have one or more substituents, $C_{1-6}$ alkoxy that may have one or more substituents, amino, mono- or di($C_1$-$C_6$ alkyl)amino that may have one or more substituents, $C_{6-14}$ aryl that may have one or more substituents, or a monocyclic or bicyclic, saturated or unsaturated heterocyclic group that may have one or more substituents, or $R^3$ and $R^4$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom, the cyclic amino group optionally having 1 to 3 substituents selected from the group consisting of halogen, hydroxy, cyano, nitro, formyl, carboxy, $C_{1-6}$ alkyl that may have one or more substituents, $C_{6-14}$ aryl that may have one or more substituents, $C_{1-6}$ alkoxycarbonyl, and mono- or di($C_1$-$C_6$ alkyl)aminocarbonyl that may have one or more substituents.

In this specification and the appended claims, when a structure "may have one or more substituents", the structure may have one or more "substituents" at chemically substitutable positions. Further, in this specification and the appended claims, when a structure "has one or more substituents", the structure has one or more "substituents" at chemically substitutable positions.

The type, number, and position of the substituents that are present (or may be present) in the structure are not limited. When two or more substituents are present, they may be the same or different. Examples of "substituents" include halogen, hydroxy, cyano, nitro, $C_{1-6}$ alkyl, $C_{3-7}$ cycloalkyl, $C_{2-6}$ alkenyl, $C_{1-6}$ alkoxy, —(C=O)—$R^2$, —$NR^3R^4$, —$NR^{3'}R^{4'}$, oxo, saturated or unsaturated heterocyclic rings, $C_{6-14}$ aryl, etc. When such substituents are present, the number thereof is typically 1 to 3.

Examples of "halogen atoms" include fluorine, chlorine, bromine, and iodine.

"$C_{1-6}$ alkyl" is a straight- or branched-chain alkyl group having 1 to 6 carbon atoms, such as methyl, ethyl, n-propyl, isopropyl, n-butyl, isobutyl, sec-butyl, tert-butyl, n-pentyl, isopentyl, neopentyl, n-hexyl, or the like.

"$C_{3-7}$ cycloalkyl" is, for example, cyclopropyl, cyclobutyl, cyclopentyl, cyclohexyl, cycloheptyl, or the like.

"$C_{2-6}$ alkenyl" is, for example, ethenyl, allyl, butenyl, butadienyl, hexatrienyl, or the like.

"$C_{1-6}$ alkoxy" is a straight- or branched-chain alkoxy group having 1 to 6 carbon atoms, such as methoxy, ethoxy, n-propoxy, isopropoxy, n-butoxy, isobutoxy, sec-butoxy, tert-butoxy, n-pentyloxy, isopentyloxy, neopentyloxy, n-hexyloxy, etc.

$R^2$ in "—(C=O)—$R^2$" is, for example, hydrogen, hydroxy, $C_{1-6}$ alkyl, $C_{1-6}$ alkoxy, —$NR^3R^4$, a saturated or unsaturated heterocyclic group, a $C_{6-14}$ aryl, or the like.

$R^3$, $R^4$, $R^{3'}$, and $R^{4'}$ in "—$NR^3R^4$" and "—$NR^{3'}R^{4'}$" are the same or different, and are each, for example, hydrogen, hydroxy, $C_{1-6}$ alkyl, $C_{1-6}$ alkoxy, amino, mono- or di($C_1$-$C_6$ alkyl)amino, ($C_1$-$C_6$ alkoxy)carbonyl, mono- or di($C_1$-$C_6$ alkyl)aminocarbonyl, a saturated or unsaturated heterocyclic group, $C_{6-14}$ aryl, or the like.

"—$NR^3R^4$" and "—$NR^{3'}R^{4'}$" may each form a saturated or unsaturated cyclic amino group (in particular, may form, taken together with the adjacent nitrogen atom, a 5- or 6-membered saturated or unsaturated cyclic amino group that may have, in addition to the adjacent nitrogen atom, 1 or 2 heteroatoms selected from the group consisting of nitrogen, oxygen, and sulfur). Examples include azetidinyl, pyrrolidinyl, piperidinyl, piperazinyl, morpholino, thiomorpholino, homopiperidinyl, imidazolyl, pyrrolyl, imidazolidinyl, oxazolidinyl, thiazolidinyl, pyrazolidinyl, imidazolinyl, pyrazolinyl, pyrazolyl, triazolyl, etc.

Examples of "saturated or unsaturated heterocyclic rings" include pyrrolidinyl, piperidinyl, piperazinyl, morpholino, thiomorpholino, homopiperidinyl, imidazolyl, thienyl, furyl, pyrrolyl, oxazolyl, isoxazolyl, thiazolyl, isothiazolyl, pyrazolinyl, triazolyl, tetrazolyl, pyridyl, pyrazyl, pyrimidinyl, pyridazyl, indolyl, isoindolyl, indazolyl, methylenedioxyphenyl, ethylenedioxyphenyl, benzofuranyl, dihydrobenzofuranyl, benzoimidazolyl, benzoxazolyl, benzothiazolyl, purinyl, quinolyl, isoquinolyl, quinazolinyl, quinoxalyl, 2,3,4,5-tetrahydro-3-oxo-pyridazin-6-yl, etc.

"$C_{6-14}$ aryl" is, for example, phenyl, naphthyl, anthracene, or the like.

"Mono- or di($C_1$-$C_6$ alkyl)amino" is an amino group having, as substituents, one or two straight- or branched-chain alkyl groups having 1 to 6 carbon atoms. Examples include methylamino, ethylamino, n-propylamino, n-hexylamino, dimethylamino, methylethylamino, ethylisobutylamino, etc.

"($C_1$-$C_6$ alkyl)carbonyl" is, for example, acetyl, propionyl, butyroyl, etc.

"($C_1$-$C_6$ alkoxy)carbonyl" is, for example, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, neopentyloxycarbonyl, n-hexyloxycarbonyl, etc.

"Mono- or di($C_1$-$C_6$ alkyl)aminocarbonyl" is, for example, methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl, n-pentylaminocarbonyl, isopentylaminocarbonyl, neopentylaminocarbonyl, n-hexylaminocarbonyl, dimethylaminocarbonyl, methylethylaminocarbonyl, ethylisobutylaminocarbonyl, etc.

In Formula (I), examples of substituents that are possessed by the furan ring represented by $R^1$ or that may be possessed by the pyrrol ring represented by $R^1$ include the above-mentioned substituents, and are each preferably halogen, cyano, nitro, $C_{1-6}$ alkyl, $C_{3-7}$ cycloalkyl, $C_{2-6}$ alkenyl, or —(C=O)—$R^2$ (the alkyl, cycloalkyl, and alkenyl may further have the above-mentioned substituents); and more preferably halogen, cyano, nitro, $C_{1-6}$ alkyl, $C_{2-6}$ alkenyl, or —(C=O)—$R^2$ [the alkyl may have one or more substituents selected from halogen, hydroxy, and —$NR^{3'}R^{4'}$, and the alkenyl may have one or more substituents selected from cyano, carboxy, and ($C_1$-$C_6$ alkoxy)carbonyl]. Still more preferably, substituents that may be possessed by the pyrrole ring represented by $R^1$ or substituents possessed by the furan ring represented by $R^1$ are cyano, $C_{1-6}$ alkyl, or —(C=O)—$R^2$.

In Formula (I), examples of "halogen", which is a substituent that is possessed by the furan ring represented by $R^1$ or that may be possessed by the pyrrole ring represented by $R^1$ include the above-mentioned halogen atoms, among which fluorine, chlorine, and bromine are preferable. The number of such halogen atoms is typically 1.

In Formula (I), examples of the "$C_{1-6}$ alkyl" of the "$C_{1-6}$ alkyl that may have one or more substituents", which is a substituent that is possessed by the furan ring represented by $R^1$ or that may be possessed by the pyrrol ring represented by $R^1$, include the above-mentioned alkyl groups. Preferable examples include $C_1$-$C_3$ alkyl, and more preferable examples include methyl and ethyl. Examples of substituents of "$C_{1-6}$ alkyl that may have one or more substituents" include the above-mentioned substituents. Preferable examples include halogen, hydroxy, di($C_1$-$C_6$ alkyl)amino, and saturated or unsaturated heterocyclic rings, and more preferable examples include 5- or 6-membered heterocyclic rings having one nitrogen atom in the ring structure as a heteroatom, such as di($C_1$-$C_6$ alkyl)amino, pyrrolidinyl, etc. The number of such substituents is typically 1.

In Formula (I), examples of the "$C_{3-7}$ cycloalkyl" of the "$C_{3-7}$ cycloalkyl that may have one or more substituents", which is a substituent that is possessed by the furan ring represented by $R^1$ or that may be possessed by the pyrrole ring represented by $R^1$, include the above-mentioned cycloalkyl groups, among which cyclopentyl and cyclohexyl are preferable. Examples of substituents of the "$C_{3-7}$ cycloalkyl that may have one or more substituents" include the above-mentioned substituents. The number of such substituents is typically 1.

In Formula (I), examples of the "$C_{2-6}$ alkenyl" of the "$C_{2-6}$ alkenyl that may have one or more substituents", which is a substituent that is possessed by the furan ring or that may be possessed by the pyrrole ring, include the above-mentioned alkenyl groups, among which ethenyl is preferable. Examples of substituents of the "$C_{2-6}$ alkenyl that may have one or more substituents" include the above-mentioned substituents, preferably 1 to 3 groups selected from the group consisting of cyano, carboxy, and ($C_1$-$C_6$ alkoxy)carbonyl, and more preferably cyano. The number of such substituents is typically 1.

Examples of the "$C_{1-6}$ alkyl" of the "$C_{1-6}$ alkyl that may have one or more substituents" represented by $R^2$ in Formula (I) include the above-mentioned alkyl groups, among which $C_1$-$C_3$ alkyl is preferable, and methyl and ethyl are more preferable. Examples of substituents of the "$C_{1-6}$ alkyl that may have one or more substituents" include the above-mentioned substituents. The number of such substituents is typically 1.

Examples of the "$C_{1-6}$ alkoxy" of the "$C_{1-6}$ alkoxy that may have one or more substituents" represented by $R^2$ in Formula (I) include the above-mentioned alkoxy groups, among which $C_1$-$C_3$ alkoxy is preferable, and methoxy and ethoxy are more preferable. Examples of substituents of "$C_{1-6}$ alkoxy that may have one or more substituents" include the above-mentioned substituents. The number of such substituents is typically 1.

Examples of the "$C_{1-6}$ alkyl" represented by $R^3$ and $R^4$ in Formula (I) include the above-mentioned alkyl groups, among which $C_{1-3}$ alkyl is preferable, and methyl is more preferable.

Examples of the "saturated or unsaturated cyclic amino group that may have, in the ring structure, 1 or 2 heteroatoms selected from the group consisting of nitrogen, oxygen, and sulfur, in addition to the adjacent nitrogen atom" represented by —$NR^3R^{4'}$ in Formula (I) include azetidinyl, pyrrolidinyl, piperidinyl, piperazinyl, morpholino, thiomorpholino, homopiperidinyl, imidazolyl, pyrrolyl, hexamethyleneimino, imidazolidinyl, oxazolidinyl, thiazolidinyl, pyrazolidinyl, imidazolinyl, pyrazolinyl, imidazolyl, pyrazolyl, triazolyl, etc., among which pyrrolidinyl is preferable.

Examples of the "$C_{1-6}$ alkyl" of the "$C_{1-6}$ alkyl that may have one or more substituents" represented by $R^3$ and $R^4$ in Formula (I) include the above-mentioned alkyl groups, among which $C_{1-3}$ alkyl is preferable, and methyl, ethyl, and propyl are more preferable. Examples of substituents of the "$C_{1-6}$ alkyl that may have one or more substituents" include the above-mentioned substituents; preferable examples include $C_{3-7}$ cycloalkyl, $C_{1-6}$ alkoxy, di($C_1$-$C_6$ alkyl)amino, ($C_1$-$C_6$ alkyl)carbonylamino, ($C_1$-$C_6$ alkoxy)carbonyl, carboxy, saturated or unsaturated heterocyclic rings (in particular, saturated or unsaturated 5- or 6-membered heterocyclic groups that have 1 or 2 nitrogen atoms in the ring structure and that may have one oxo group), phenyl having 1 or 2 substituents selected from the group consisting of halogen, $C_{1-6}$ alkoxy, and methylenedioxy; and more preferable examples include methoxy, dimethylamino, acetamide, methoxycarbonyl, ethoxycarbonyl, carboxy, pyrrolidinyl, piperidinyl, pyridyl, methylenedioxyphenyl, dichlorophenyl, dimethoxyphenyl, and 2,3,4,5-tetrahydro-3-oxo-pyridazin-6-yl. The number of such substituents is typically 1.

Examples of the "$C_{1-6}$ alkoxy" of the "$C_{1-6}$ alkoxy that may have one or more substituents" represented by $R^3$ and $R^4$ in Formula (I) include the above-mentioned alkoxy groups, among which $C_{1-3}$ alkoxy is preferable. Examples of substituents of the "$C_{1-6}$ alkoxy that may have one or more substituents" include the above-mentioned substituents. The number of such substituents is typically 1.

Examples of the "mono- or di($C_1$-$C_6$ alkyl)amino" of the "mono- or di($C_1$-$C_6$ alkyl)amino that may have one or more substituents" represented by $R^3$ and $R^4$ include the above-mentioned mono- or di($C_1$-$C_6$ alkyl)amino groups. Examples of substituents of the "mono- or di($C_{1-6}$ alkyl)amino that may have one or more substituents" include the above-mentioned substituents. The number of such substituents is typically 1.

Examples of the "$C_{6-14}$ aryl" of the "$C_{6-14}$ aryl that may have one or more substituents" represented by $R^3$ and $R^4$ in Formula (I) include the above-mentioned aryl groups, among which phenyl is preferable. Examples of substituents of the "$C_{6-14}$ aryl that may have one or more substituents" include the above-mentioned substituents, among which halogen, cyano, and $C_{1-6}$ alkoxy are preferable, and cyano is more preferable. The number of such substituents is typically 1 to 3, and in particular 1.

Examples of the "saturated or unsaturated heterocyclic ring" of the "saturated or unsaturated heterocyclic ring that may have one or more substituents" represented by $R^3$ and $R^4$ in Formula (I) include the above-mentioned saturated or unsaturated heterocyclic rings; preferable examples include monocyclic or bicyclic, saturated or unsaturated heterocyclic rings; and more preferable examples include morpholino, isooxazolyl, indolyl, methylenedioxyphenyl, ethylenedioxyphenyl, dihydrobenzofuranyl, and benzothiazolyl. Examples of substituents of the "saturated or unsaturated heterocyclic ring that may have one or more substituents" include the above-mentioned substituents. The number of such substituents is typically 1.

Examples of the "saturated or unsaturated cyclic amino group that may have, in the ring structure, 1 or 2 heteroatoms selected from the group consisting of nitrogen, oxygen, and sulfur, in addition to the adjacent nitrogen atom" represented by —$NR^3R^4$ in Formula (I) include azetidinyl, pyrrolidinyl, piperidinyl, piperazinyl, morpholino, thiomorpholino, homopiperidinyl, pyrrolidinyl, imidazolyl, pyrrolyl, hexamethyleneimino, imidazolidinyl, oxazolidinyl, thiazolidinyl, pyrazolidinyl, imidazolinyl, pyrazolinyl, imidazolyl, pyrazolyl, triazolyl, etc. Preferable examples include a 5- or 6-membered saturated or unsaturated cyclic amino group that is formed together with the adjacent nitrogen atom and that may have, in the ring structure, one heteroatoms selected from the group consisting of nitrogen, oxygen, and sulfur, in addition to the adjacent nitrogen atom. More preferable examples include pyrrolidinyl, thiazolidinyl, pyrazolinyl, morpholino, piperazinyl, and piperidinyl; still more preferable examples include pyrrolidinyl, pyrazolinyl, and morpholino; and even more preferable examples include pyrrolidinyl and morpholino.

Examples of substituents that may be possessed by the "saturated or unsaturated cyclic amino group that may have, in the ring structure, 1 or 2 heteroatoms selected from the group consisting of nitrogen, oxygen, and sulfur, in addition to the adjacent nitrogen atom" represented by —$NR^3R^4$ in Formula (I) include the above-mentioned substituents, among which (a) halogen, (b) hydroxy, (c) cyano, (d) nitro, (e) formyl, (f) carboxy, (g) $C_{1-6}$ alkyl, (h) $C_{6-14}$ aryl, (i) ($C_1$-$C_6$ alkoxy)carbonyl, or (j) mono- or di($C_1$-$C_6$ alkyl)aminocarbonyl are preferable. Alkyl (g), aryl (h), ($C_1$-$C_6$ alkoxy)carbonyl (i), and mono- or di($C_1$-$C_6$ alkyl)aminocarbonyl (j) may have substituents as mentioned above. The number of substituents (in particular the above-mentioned substituents (a) to (j)) that may be possessed by the saturated or unsaturated heterocyclic ring is 1 or 2, and in particular 1.

Examples of "halogen (a)" include the above-mentioned halogen atoms.

Examples of the "$C_{1-6}$ alkyl" of "$C_{1-6}$ alkyl (g)", which may have one or more substituents, include the above-mentioned alkyl groups. Examples of substituents of the "$C_{1-6}$ alkyl", which may have one or more substituents, include the above-mentioned substituents. The number of such substituents is typically 1 to 3.

Examples of the "aryl" of "$C_{6\text{-}14}$ aryl (h)", which may have one or more substituents, include the above-mentioned aryl groups, among which phenyl is preferable. Examples of substituents of the "$C_{6\text{-}14}$ aryl", which may have one or more substituents, include the above-mentioned substituents. The number of such substituents is typically 1 to 3.

Examples of the "$C_{1\text{-}6}$ alkoxycarbonyl" of "($C_1$-$C_6$ alkoxy) carbonyl (i)", which may have one or more substituents, include the above-mentioned alkoxycarbonyl groups, with ethoxycarbonyl being preferable. Examples of substituents of the "($C_1$-$C_6$ alkoxy)carbonyl", which may have one or more substituents, include the above-mentioned substituents. The number of such substituents is typically 1 to 3.

Examples of "mono- or di($C_1$-$C_6$ alkyl)aminocarbonyl (j)", which may have one or more substituents, include the above-mentioned mono- or di($C_1$-$C_6$ alkyl)aminocarbonyl groups. Examples of substituents of the "mono- or di($C_1$-$C_6$ alkyl)aminocarbonyl", which may have one or more substituents, include the above-mentioned substituents. Preferable examples include di($C_1$-$C_6$ alkyl)amino, $C_{1\text{-}6}$ alkoxy, and $C_{3\text{-}7}$ cycloalkyl, and more preferable examples include dimethylamino, methoxy, and cyclohexyl. The number of such substituents is typically 1.

Among the compounds represented by Formula (I), the following compounds are more preferable.

(A) A benzimidazole compound represented by Formula (I), wherein:
$X^1$ is carbonyl;
$R^1$ is a furan ring having 2 or 3 substituents, or a pyrrole ring having 2 or 3 substituents as well as a hydrogen atom bonded to the nitrogen atom, the substituents on two carbon atoms of the furan ring or pyrrole ring being $C_{1\text{-}6}$ alkyl, and the remaining carbon atom having a hydrogen atom bonded thereto, or cyano or —(C=O)—$R^2$ as a substituent bonded thereto;
$R^2$ is hydroxy, $C_{1\text{-}6}$ alkoxy, or —$NR^3R^4$; and
one of $R^3$ and $R^4$ is hydrogen or $C_{1\text{-}3}$ alkyl, and the other is hydrogen, hydroxy, $C_{1\text{-}3}$ alkyl that may have one or more substituents, $C_{1\text{-}3}$ alkoxy that may have one or more substituents, phenyl that may have 1 to 3 substituents selected from the group consisting of halogen, cyano, and $C_{1\text{-}6}$ alkoxy, morpholino, isooxazolyl, indolyl, methylenedioxyphenyl, ethylenedioxyphenyl, dihydrobenzofuranyl, or benzothiazolyl, or
—$NR^3R^4$ is pyrrolidinyl, thiazolidinyl, pyrazolinyl, morpholino, or piperazinyl;
or a salt thereof.

(B) A benzimidazole compound represented by Formula (I), wherein:
$X^1$ is carbonyl;
$R^1$ is a furan ring that has three substituents and that is attached to the benzimidazole ring at the 4-position, or a pyrrole ring that has three substituents as well as a hydrogen atom bonded to the nitrogen atom and that is attached to the benzimidazole ring at the 4-position, and
of the substituents on the furan ring or pyrrole ring, the substituents at the 3- and 5-positions are $C_{1\text{-}3}$ alkyl, and the substituent at the 2-position is cyano or —(C=O)—$R^2$;
$R^2$ is hydroxy, ethoxy, or —$NR^3R^4$; and
one of $R^3$ and $R^4$ is hydrogen or $C_{1\text{-}3}$ alkyl, and the other is hydrogen, hydroxy, $C_{1\text{-}3}$ alkyl that may have one or more substituents, $C_{1\text{-}3}$ alkoxy that may have one or more substituents, or phenyl that may have 1 to 3 substituents selected from the group consisting of halogen, cyano, and $C_{1\text{-}3}$ alkoxy, or —$NR^3R^4$ is pyrrolidinyl, pyrazolinyl, or morpholino;
or a salt thereof.

(C) A benzimidazole compound represented by Formula (I), wherein:
$X^1$ is carbonyl;
$R^1$ is a pyrrole ring that has three substituents as well as a hydrogen atom bonded to the nitrogen atom and that is attached to the benzimidazole ring at the 4-position, and
of the substituents of the pyrrole ring, the substituents at the 3- and 5-positions are methyl, and the substituent at the 2-position is —(C=O)—$R^2$;
$R^2$ is hydroxy, ethoxy, or —$NR^3R^4$; and
one of $R^3$ and $R^4$ is hydrogen or $C_{1\text{-}3}$ alkyl, and the other is $C_{1\text{-}3}$ alkyl that may have one or more substituents, $C_{1\text{-}3}$ alkoxy, or
—$NR^3R^4$ is pyrrolidinyl or morpholino;
or a salt thereof.

In Compounds (A) to (C) described above, examples of substituents of the "$C_{1\text{-}3}$ alkyl that may have one or more substituents" include $C_{1\text{-}6}$ alkoxy, di($C_1$-$C_6$ alkyl)amino, acetamide, ($C_1$-$C_6$ alkoxy)carbonyl, carboxy, saturated or unsaturated heterocyclic groups (preferably 5- or 6-membered heterocyclic rings having 1 or 2 nitrogen atoms in the ring structure, the heterocyclic rings optionally having one oxo group); and more preferably pyrrolidinyl, piperidinyl, pyridyl, or 2,3,4,5-tetrahydro-3-oxo-pyridazin-6-yl], $C_{3\text{-}7}$ cycloalkyl, or phenyl having 1 or 2 substituents selected from halogen and $C_{1\text{-}6}$ alkoxy. The number of such substituents is 1.

In Compounds (A) and (B) described above, examples of substituents of the "$C_{1\text{-}3}$ alkoxy that may have one or more substituents" include the above-mentioned substituents. The number of such substituents is typically 1.

Of Compounds (A) to (C), Compounds (A') to (C') shown below are particularly preferable.

(A') A benzimidazole compound represented by Formula (I), wherein:
$X^1$ is carbonyl;
$R^1$ is a furan ring having 2 or 3 substituents or a pyrrole ring having 2 or 3 substituents as well as a hydrogen atom bonded to the nitrogen atom, the substituents on two carbon atoms of the furan ring or pyrrole ring being $C_{1\text{-}6}$ alkyl, and the remaining carbon atom having a hydrogen atom bonded thereto, or cyano or —(C=O)—$R^2$ as a substituent bonded thereto;
$R^2$ is hydroxy, $C_{1\text{-}6}$ alkoxy, or —$NR^3R^4$; and
one of $R^3$ and $R^4$ is hydrogen or $C_{1\text{-}3}$ alkyl, and the other is hydrogen, hydroxy, $C_{1\text{-}3}$ alkyl that may have one or more substituents (the substituent of the alkyl is $C_{1\text{-}6}$ alkoxy, di($C_1$-$C_6$ alkyl)amino, acetamide, ($C_1$-$C_6$ alkoxy)carbonyl, carboxy, a saturated or unsaturated 5- or 6-membered heterocyclic ring having 1 or 2 nitrogen atoms in the ring structure (the heterocyclic ring optionally having one oxo group), $C_{3\text{-}7}$ cycloalkyl, or phenyl having 1 or 2 substituents selected from halogen and $C_{1\text{-}6}$ alkoxy), $C_{1\text{-}3}$ alkoxy, phenyl that may have 1 to 3 substituents selected from the group consisting of halogen, cyano, and $C_{1\text{-}3}$ alkoxy, morpholino, isoxazolyl, indolyl, methylenedioxyphenyl, ethylenedioxyphenyl, dihydrobenzofuranyl, or benzothiazolyl, or
—$NR^3R^4$ is pyrrolidinyl, thiazolidinyl, pyrazolinyl, morpholino, or piperazinyl;
or a salt thereof.

(B') A benzimidazole compound represented by Formula (I), wherein:
$X^1$ is carbonyl;
$R^1$ is a furan ring that has three substituents and that is attached to the benzimidazole ring at the 4-position, or a pyrrole ring that has three substituents as well as a hydrogen atom bonded to the nitrogen atom and that is attached to the benzimidazole ring at the 4-position, and of the substituents on the furan ring and pyrrole ring, the substituents at the 3- and the 5-positions are $C_{1-3}$ alkyl, the substituent at the 2-position is cyano or —(C=O)—$R^2$;

$R^2$ is hydroxy, ethoxy, or —$NR^3R^4$; and one of $R^3$ and $R^4$ is hydrogen or $C_{1-3}$ alkyl, and the other is hydrogen, hydroxy, $C_{1-3}$ alkyl that may have one or more substituents (the substituent of the alkyl is $C_{1-6}$ alkoxy, di($C_1$-$C_6$ alkyl)amino, acetamide, ($C_1$-$C_6$ alkoxy)carbonyl, carboxy, pyrrolidinyl, piperidinyl, pyridyl, 2,3,4,5-tetrahydro-3-oxo-pyridazin-6-yl, $C_{3-7}$ cycloalkyl, or phenyl having 1 or 2 substituents selected from halogen and $C_{1-6}$ alkoxy), $C_{1-3}$ alkoxy, or phenyl that may have 1 to 3 substituents selected from the group consisting of halogen, cyano, and $C_{1-3}$ alkoxy, or —$NR^3R^4$ is pyrrolidinyl, pyrazolinyl, or morpholino;

or a salt thereof.

(C') A benzimidazole compound represented by Formula (I), wherein:

$X^1$ is carbonyl;

$R^1$ is a pyrrole ring that has three substituents as well as a hydrogen atom bonded to the nitrogen atom and that is attached to the benzimidazole ring at the 4-position, and of the substituents of the pyrrole ring, the substituents at the 3- and the 5-position are methyl, and the substituent at the 2-position is —(C=O)—$R^2$;

$R^2$ is hydroxy, ethoxy, or —$NR^3R^4$; and one of $R^3$ and $R^4$ is hydrogen or $C_{1-3}$ alkyl, and the other is $C_{1-3}$ alkyl that may have one or more substituents (the substituent of the alkyl is $C_{1-6}$ alkoxy, di($C_1$-$C_6$ alkyl)amino, acetamide, ($C_1$-$C_6$ alkoxy)carbonyl, carboxy, pyrrolidinyl, piperidinyl, pyridyl, 2,3,4,5-tetrahydro-3-oxo-pyridazin-6-yl, $C_{3-7}$ cycloalkyl, or phenyl having 1 or 2 substituents selected from halogen and $C_{1-6}$ alkoxy, or $C_{1-3}$ alkoxy, or —$NR^3R^4$ is pyrrolidinyl or morpholino;

or a salt thereof.

(D) The following are specific examples of the compounds represented by Formula (I). In the following, the numbers in the parentheses after the compound names are numbers assigned to the compounds obtained in the Examples given hereinafter.

4-(5-Benzoylbenzimidazol-2-yl)-3,5-dimethylfuran-2-carboxamide (2), (4-(5-benzoylbenzimidazol-2-yl)-3,5-dimethyl-2-furanylcarbonyl)pyrrolidine (3), N-(3,4-methylenedioxyphenyl)methyl-4-(5-benzoylbenzimidazol-2-yl)-3,5-dimethylfuran-2-carboxamide (4), 2-(2-formyl-3,5-dimethyl-pyrrol-4-yl)-5-benzoylbenzimidazole (8), 2-(2-acrylonitrile-3,5-dimethyl-pyrrol-4-yl)-5-benzoylbenzimidazole (9), 4-(5-benzoylbenzimidazol-2-yl)-3,5-dimethylpyrrole-2-carboxylic acid (10), N-methyl-N-(2-dimethylaminoethyl)-4-(5-benzoylbenzimidazol-2-yl)-3,5-dimethylpyrrole-2-carboxamide (11), 4-(5-benzoylbenzimidazol-2-yl)-3,5-dimethylpyrrole-2-carboxamide (12), 2-(2-cyano-3,5-dimethyl-pyrrol-4-yl)-5-benzoylbenzimidazole (13), N-(methoxy)-4-(5-benzoylbenzimidazol-2-yl)-3,5-dimethylpyrrole-2-carboxamide (14), (N-methoxy-N-methyl)-4-(5-benzoylbenzimidazol-2-yl)-3,5-dimethylpyrrole-2-carboxamide (15), N-(3-methoxypropyl)-4-(5-benzoylbenzimidazol-2-yl)-3,5-dimethylpyrrole-2-carboxamide (16), N-(3-dimethylaminopropyl)-4-(5-benzoylbenzimidazol-2-yl)-3,5-dimethylpyrrole-2-carboxamide (17), N-(2-acetamidoethyl)-4-(5-benzoylbenzimidazol-2-yl)-3,5-dimethylpyrrole-2-carboxamide (18), N-(2-ethoxycarbonylethyl)-4-(5-benzoylbenzimidazol-2-yl)-3,5-dimethylpyrrole-2-carboxamide (19), N-(1-methoxycarbonylmethyl)-4-(5-benzoylbenzimidazol-2-yl)-3,5-dimethylpyrrole-2-carboxamide (20), N-(2-carboxyethyl)-4-(5-benzoylbenzimidazol-2-yl)-3,5-dimethylpyrrole-2-carboxamide (21), N-(1-carboxymethyl)-4-(5-benzoylbenzimidazol-2-yl)-3,5-dimethylpyrrole-2-carboxamide (22), N-(2-pyrrolidin-1-yl-ethyl)-4-(5-benzoylbenzimidazol-2-yl)-3,5-dimethylpyrrol-2-carboxamide (23), N-(2-piperidin-1-yl-ethyl)-4-(5-benzoylbenzimidazol-2-yl)-3,5-dimethylpyrrole-2-carboxamide (24), N-(cyclohexylmethyl)-4-(5-benzoylbenzimidazol-2-yl)-3,5-dimethylpyrrole-2-carboxamide (25), N-(5-methylisoxazol-3-yl)-4-(5-benzoylbenzimidazol-2-yl)-3,5-dimethylpyrrole-2-carboxamide (26), N-(4-cyanophenyl)-4-(5-benzoylbenzimidazol-2-yl)-3,5-dimethylpyrrole-2-carboxamide (27), N-(indol-5-yl)-4-(5-benzoylbenzimidazol-2-yl)-3,5-dimethylpyrrole-2-carboxamide (28), N-(3,4-methylenedioxyphenyl-1-yl)-4-(5-benzoylbenzimidazol-2-yl)-3,5-dimethylpyrrole-2-carboxamide (29), N-(2,3-dihydrobenzofuran-5-yl)-4-(5-benzoylbenzimidazol-2-yl)-3,5-dimethylpyrrole-2-carboxamide (30), N-(benzothiazol-6-yl)-4-(5-benzoylbenzimidazol-2-yl)-3,5-dimethylpyrrole-2-carboxamide (31), N-(3,4-ethylenedioxyphenyl)-4-(5-benzoylbenzimidazol-2-yl)-3,5-dimethylpyrrole-2-carboxamide (32), N-(2-pyridylmethyl)-4-(5-benzoylbenzimidazol-2-yl)-3,5-dimethylpyrrole-2-carboxamide (33), N-(2-(2-pyridyl)ethyl)-4-(5-benzoylbenzimidazol-2-yl)-3,5-dimethylpyrrole-2-carboxamide (34), N-(3,4-dichlorobenzyl)-4-(5-benzoylbenzimidazol-2-yl)-3,5-dimethylpyrrole-2-carboxamide (35), N-(3,4-dimethoxybenzyl)-4-(5-benzoylbenzimidazol-2-yl)-3,5-dimethylpyrrole-2-carboxamide (36), N-(3,4-methylenedioxyphenylmethyl)-4-(5-benzoylbenzimidazol-2-yl)-3,5-dimethylpyrrole-2-carboxamide (37), N-(2,3,4,5-tetrahydro-3-oxo-pyridazin-6-yl-methyl)-4-(5-benzoylbenzimidazol-2-yl)-3,5-dimethylpyrrole-2-carboxamide (38), ((4-(5-benzoylbenzimidazol-2-yl)-3,5-dimethylpyrrol-2-yl)-carbonyl)pyrrolidine (39), ((4-(5-benzoylbenzimidazol-2-yl)-3,5-dimethylpyrrol-2-yl)-carbonyl)morpholine (40), ((4-(5-benzoylbenzimidazol-2-yl)-3,5-dimethylpyrrol-2-yl)-carbonyl-4-phenylpiperazine (41), ((4-(5-benzoylbenzimidazol-2-yl)-3,5-dimethylpyrrol-2-yl)-carbonyl)pyrazoline (42), ((4-(5-benzoylbenzimidazol-2-yl)-3,5-dimethylpyrrol-2-yl)-carbonyl-4-hydroxypiperidine (43), ((4-(5-benzoylbenzimidazol-2-yl)-3,5-dimethylpyrrol-2-yl)-carbonyl)-4-ethoxycarbonylpiperidine (44), ((4-(5-benzoylbenzimidazol-2-yl)-3,5-dimethylpyrrol-2-yl)-carbonyl)piperidine-4-carboxylic acid (45), N-dimethylaminoethyl-1-(4-(5-benzoylbenzimidazol-2-yl)-3,5-dimethylpyrrol-2-yl)-carbonyl)piperidine-4-carboxamide (46), N-methyl-N-(2-dimethylaminoethyl)-1-(4-(5-benzoylbenzimidazol-2-yl)-3,5-dimethylpyrrol-2-yl)-carbonyl)piperidine-4-carboxamide (47), N-(3-dimethylaminopropyl)-1-((4-(5-benzoylbenzimidazol-2-yl)-3,5-dimethylpyrrol-2-yl)-carbonyl)piperidine-4-carboxamide (48), N-(3-methoxypropyl)-1-(4-(5-benzoylbenzimidazol-2-yl)-3,5-dimethylpyrrol-2-yl)-carbonyl)piperidine-4-carboxamide (49), N-cyclohexylmethyl-1-((4-(5-benzoylbenzimidazol-2-yl)-3,5-dimethylpyrrol-2-yl)-carbonyl)piperidine-4-carboxamide (50), (N,N-dimethyl)-4-(5-benzoylbenzimidazol-2-yl)-3,5-dimethylpyrrole-2-carboxamide (64), (N-hydroxy-N-methyl)-4-(5-benzoylbenzimidazol-2-yl)-3,5-dimethylpyrrole-2-carboxamide (65), (N-methyl)-4-(5-benzoylbenzimidazol-2-yl)-3,5-dimethylpyrrole-2-carboxamide (66), (N-hydroxymethyl)-4-(5-benzoylbenzimidazol-2-yl)-3,5-dimethylpyrrole-2-carboxamide (67), 4-(5-phenoxybenzimidazol-2-yl)-3,5-dimethylpyrrole-2-carboxylic acid ethyl ester (68), 4-(5-phenoxybenzimidazol-2-yl)-3,5-dimethylpyrrole-2-carboxylic acid (69), (4-(5-phenoxybenzimidazol-2-yl)-3,5-dimethylpyrrol-2-yl)-2-carbonyl)pyrrolidine (70), (4-(5-phenoxybenzimidazol-2-yl)-3,5-dimethylpyrrol-2-yl)-2-carbonyl)morpholine (71), N-(2-(2-pyridyl)ethyl)-4-(5-phenoxybenzimidazol-2-yl)-3,5-dimethylpyrrole-2-carboxamide (72), N-(methoxy)-4-(5-phenoxybenzimidazol-2-yl)-3,5-dimethylpyrrole-2-carboxamide (73), (N-methoxy-N-methyl)-4-(5-phenoxybenzimidazol-2-yl)-3,5-dimethylpyrrole-2-carboxamide (74), 2-(2-cyano-3,5-dimethylpyrrol-4-yl)-5-phenoxybenzimidazole (75), 4-(5-phenoxybenzimidazol-2-yl)-3,5-dimethylfuran-2-carboxamide (76), and salts thereof.

(E) Of the compounds represented by Formula (I), the following are particularly preferable.

(4-(5-benzoylbenzimidazol-2-yl)-3,5-dimethyl-2-furanylcarbonyl)pyrrolidine, 4-(5-benzoylbenzimidazol-2-yl)-3,5-dimethylpyrrole-2-carboxylic acid, 2-(2-cyano-3,5-dimethyl-pyrrol-4-yl)-5-benzoylbenzimidazole, N-(methoxy)-4-(5-benzoylbenzimidazol-2-yl)-3,5-dimethylpyrrole-2-carboxamide, (N-methoxy-N-methyl)-4-(5-benzoylbenzimidazol-2-yl)-3,5-dimethylpyrrole-2-carboxamide, N-(3-dimethylaminopropyl)-4-(5-benzoylbenzimidazol-2-yl)-3,5-dimethylpyrrole-2-carboxamide, N-(2-(2-pyridyl)ethyl)-4-(5-benzoylbenzimidazol-2-yl)-3,5-dimethylpyrrole-2-carboxamide, ((4-(5-benzoylbenzimidazol-2-yl)-3,5-dimethylpyrrol-2-yl)carbonyl)morpholine, ((4-(5-benzoylbenzimidazol-2-yl)-3,5-dimethylpyrrol-2-yl)-carbonyl)pyrazoline, (N,N-dimethyl)-4-(5-benzoylbenzimidazol-2-yl)-3,5-dimethylpyrrole-2-carboxamide, and salts thereof.

Some of Compounds (1) of the present invention may exist as tautomers due to the benzimidazole ring, optical isomers due to asymmetric carbon atoms (when asymmetric carbon atoms are present), and/or other isomers. The present invention encompasses such tautomers and isomers isolated, and mixtures of thereof.

Compound (I) of the present invention encompasses pharmaceutically acceptable prodrugs. The pharmaceutically acceptable prodrugs are compounds having functional groups that can be converted, under chemical conditions such as solvolysis or under physiological conditions, into amino, hydroxy, carboxy, carbonyl, or like functional groups of Compound (I), which is an active ingredient of the pharmaceutical agent of the present invention. Representative functional groups of prodrugs include groups mentioned in "Iyakuhin no Kaihatsu (Development of Pharmaceuticals)", vol. 7, pp. 163-198, Hirokawa Publishing (1990).

Compound (I) of the present invention may form an acid addition salt or a salt with a base, and the present invention also encompasses such salts, and in particular pharmaceutically acceptable salts. Specific examples include acid addition salts with inorganic acids such as hydrochloric acid, hydrobromic acid, hydroiodic acid, sulfuric acid, nitric acid, phosphoric acid, etc., or organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluenesulfonic acid, glutamic acid, etc.; salts with inorganic bases such as sodium, potassium, magnesium, calcium, aluminium, etc., organic bases such as methylamine, ethylamine, meglumine, ethanolamine, etc., or basic amino acids such as lysine, arginine, ornithine, etc.; and ammonium salts.

The present invention further encompasses the hydrates, solvates, and crystal polymorphs, of Compound (I) of the present invention and salts thereof.

Method for Manufacturing the Compound of the Invention

The compound expressed by Formula (I) can be manufactured by the method shown below, for example.

[First Method]

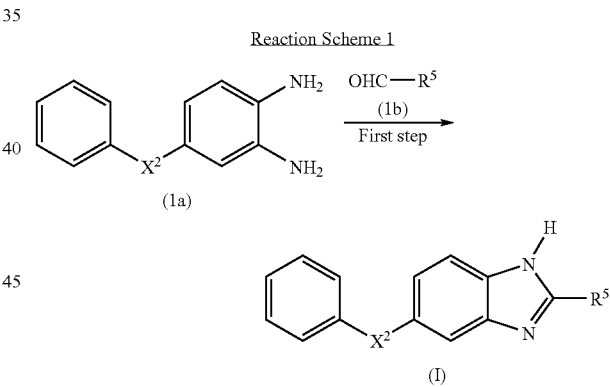

In the above Reaction Scheme 1, $R^5$ indicates the above $R^1$, and $X^2$ indicates the above $X^1$ (hereafter, idem).

This manufacturing method is a method of manufacturing the compound shown in Formula (I) by reacting the phenylenediamine derivative shown in Formula (1a) or a salt thereof with an aldehyde derivative shown in Formula (1b) via an ordinary ring closure.

This reaction is normally carried out using 0.5 to 10 moles, and preferably 0.8 to 2 moles, of the aldehyde derivative shown in Formula (1b) with respect to 1 mole of the phenylenediamine derivative shown in Formula (1a) in the presence of 0.5 to 10 moles, and preferably 0.8 to 3 moles, of sodium hydrogen sulfite, potassium ferricyanide or ferric chloride-oxygen, in a solvent which is inactive to the reaction, e.g., an ester such as ethyl acetate or butyl acetate, water, an alcohol such as methanol, ethanol or isopropanol, N,N-dimethylformamide, N,N-dimethylacetamide, N-methylpyrrolidone, dimethyl sulfoxide and pyridine from 0° C. to 180° C., and preferably from 50° C. to 150° C.

This reaction may be carried out also in the presence of 0.5 to 10 moles and preferably 1 to 5 moles of an organic acid, such as formic acid or acetic acid, or a mineral acid, such as hydrochloric acid or sulfuric acid relative, to 1 mole of the phenylenediamine derivative shown in Formula (1a), in a solvent such as an alcohol, nitrobenzene or polyphosphoric acid from 0° C. to 200° C., and preferably from 50° C. to 180° C.

The phenylenediamine derivative expressed by the above Formula (1a) is known in the art, or can be manufactured in accordance with a method known in the art. Moreover, the aldehyde derivative expressed by the above Formula (1b) is known in the art, or can be manufactured in accordance with a method known in the art.

[Second Method]

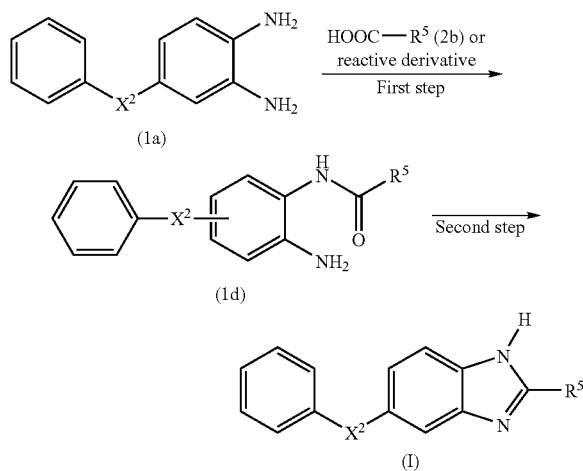

This method is a method involving a first step of amidation of the phenylenediamine derivative shown in Formula (1a) or a salt thereof with a carboxylic acid derivative shown in Formula (2b) or a reactive derivative thereof by a normal method to obtain an acylaminobenzene derivative shown in Formula (1d), and a second step of manufacturing the compound shown in Formula (1) by subjecting the acylaminobenzene derivative shown in Formula (1d) to a dehydration reaction.

<First Step>

In the first step, examples of the reactive derivative of compound (2b) are active esters, i.e., ordinary alkyl esters having 1-6 carbon atoms such as methyl esters, ethyl esters and tert-butyl esters, acid halides such as acid chlorides and acid bromides, acid azides, N-hydroxybenzotriazole, and N-hydroxysuccimide and p-nitrophenol and the like, and mixed acid anhydrides such as symmetrical acid anhydrides, alkylcarboxylic acids and p-toluenesulfonic acid.

When reacting the compound (2b) with a free acid, or when an active ester or acid halide are reacted without being isolated, a condensation agent such as dicyclohexyl carbodiimide, carbonyldiimadazole, diphenyl phosphorylazide, diethyl phosphorylazide, 1-ethyl-3-(3-dimethylamino propyl)carbodiimide hydrochloride and 4-(4,6-dimethoxy-1,3,5-triazin-2-yl)-4-methylmorpholinium or the like may be used.

The reaction is carried out using 0.5 to 10 moles and preferably 0.8 to 2 moles of the carboxylic acid derivative shown in Formula (2b) or a reactive derivative thereof with respect to 1 mole of the phenylenediamine derivative shown in Formula (1a). If the above condensation agent is used, its amount is 0.5 to 20 moles and preferably 0.8 to 3 moles with respect to 1 mole of the phenylenediamine derivative shown in Formula (1a). Although dependent on the reactive derivative or condensation agent used, the reaction is normally carried out in a solvent which is inactive to the reaction, e.g., a halogenated hydrocarbon, such as dichloroethane, chloroform or carbon tetrachloride; an aromatic hydrocarbon, such as benzene, toluene or xylene; an ether, such as diethyl ether, tetrahydrofuran or dioxane; an ester, such as ethyl acetate; an alcohol such as methanol, ethanol, n-propanol or isopropanol; water; acetonitrile; N,N-dimethylformamide; N,N-dimethylacetamide; dimethylsulfoxide; or pyridine; from −20° C. to 150° C., and preferably 0° C. to 100° C.

The reaction may proceed smoothly if it is carried out in the presence of about 0.5 to 20 moles and preferably 0.8 to 5 moles of a base such as triethylamine, diisopropylethylamine, N-methylmorpholine, N,N-dimethyl aniline, N,N-diethylaniline, 4-(N,N-dimethylamino)pyridine, pyridine, picoline, or lutidine, with respect to 1 mole of the phenylediamine derivative shown in Formula (1a).

<Second Step>

The dehydration reaction of the second step may be carried out in a solvent that is inactive to the reaction, e.g., a halogenated hydrocarbon, an aromatic hydrocarbon, or an ether, or in the absence of a solvent, using a catalytic amount or solvent amount of acid, from −20° C. to 200° C., and preferably from 20° C. to 180° C. The acid used may be hydrochloric acid, sulfuric acid, phosphoric acid, acetic acid, trifluoroacetic acid, methane sulfonic acid, trifluoromethanesulfonic acid, p-toluenesulfonic acid, or the like.

The carboxylic acid derivative expressed by the above formula (2b) is known in the art, or can be manufactured by a method known in the art.

[Third Method]

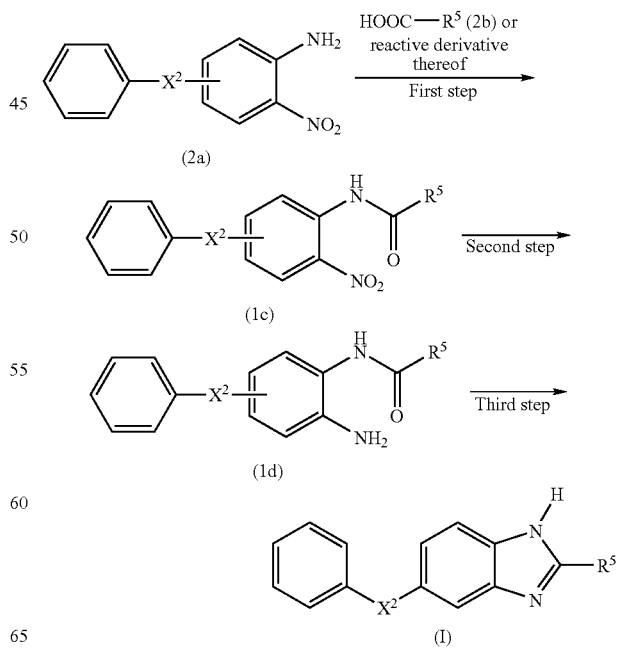

This method is a method involving a first step of amidation of the aminonitrobenzene derivative shown in Formula (2a) or a salt thereof, with a carboxylic acid derivative shown in Formula (2b) or a reactive derivative thereof by the normal method to obtain an acylaminonitrobenzene derivative shown in Formula (1c), a second step of subjecting the obtained acylaminonitrobenzene derivative shown in Formula (1c) to a reduction reaction to obtain the acylaminobenzene derivative (1d), and a third step of manufacturing the compound shown in Formula (I) by a dehydration reaction.

The amidation of the first step may be performed in a similar way to the first step of the second method.

The reduction reaction of the second step may be carried out under any reaction conditions providing that the nitro group is reduced and converted to an amino group, but considering the nature of the other functional groups of the acylaminonitrobenzene derivative (1c), the reaction conditions must be selected. For example, 0.01 to 5 moles and preferably 0.05 to 1 moles of a metal having reducing properties such as reduced iron, stannous chloride or ferric chloride, may be used in water, an alcohol such as methanol, ethanol or isopropanol, an ether such as diethyl ether, tetrahydrofuran in dioxane or a mixture of these solvents, with respect to 1 mole of the acylaminonitrobenzene derivative shown in Formula (1c), in the presence of 1 to 30 moles, and preferably 3 to 10 moles, of an ammonium salt such as ammonium chloride or hydrazine hydrate, from 0° C. to 150° C., and preferably from 20° C. to 120° C. Alternatively, the reaction is carried out in the presence of 0.001 to 1 moles, and preferably 0.01 to 0.3 moles, of a metal having reducing properties such as palladium on a carbon carrier, platinum chloride or Raney nickel with respect to 1 mole of the acylaminonitrobenzene derivative shown in Formula (1c) in an alcohol, an ether, an ester such as ethyl acetate or butyl acetate, an organic acid such as formic acid or acetic acid, or in a mixture of these solvents, from 0° C. to 120° C., and preferably from 20° C. to 100° C., in an atmosphere of hydrogen gas at normal pressure or under compression, or using formic acid, ammonium formate or cyclohexane, or the like, as a hydrogen source.

The dehydration reaction of the third step may be performed in a similar way to the second step of the second method.

The aminonitrobenzene derivative expressed in the above formula (2a) and salts thereof are known in the art, or can be manufactured in accordance with a method known in the art.

[Fourth Method]

In the invention, as shown by the following Reaction Scheme 4, compounds having particular functional groups may be converted to other compounds of the invention by chemically Reaction Scheme

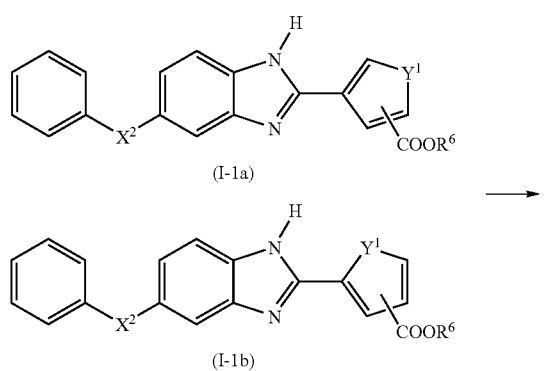

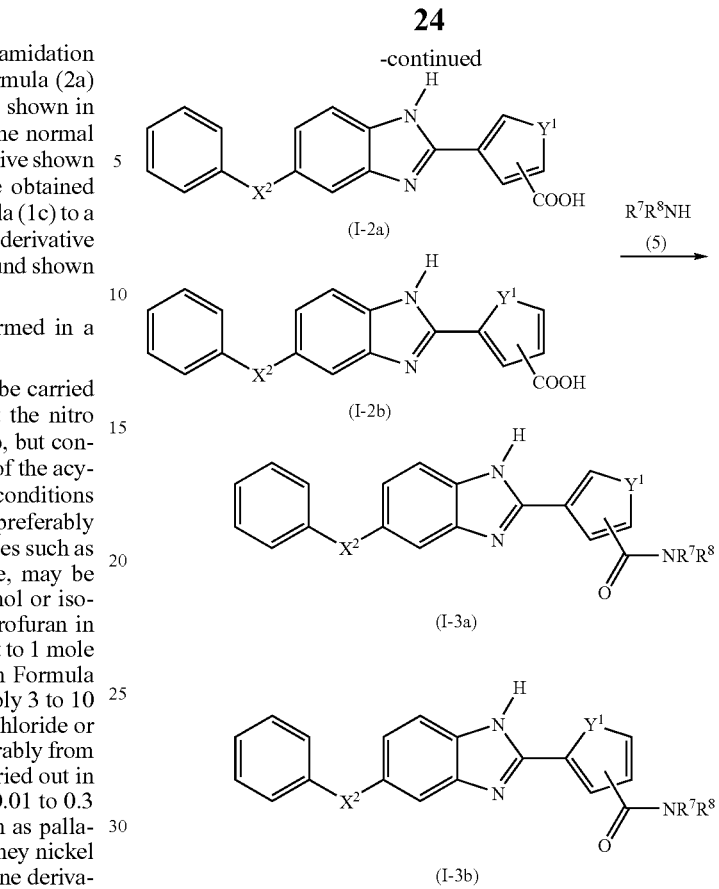

modifying these groups.

In the above Reaction Scheme 4, $Y^1$ indicates an oxygen atom or nitrogen atom, $R^6$ may be any group provided that it is a protective group that can be used with a carboxylic acid, e.g., an alkyl group having 1 to 6 carbon atoms, $NR^7R^8$ indicates the above $NR^3R^4$, and $X^2$ indicates the above $X^1$ (hereafter, idem).

In the derivative having a ($C_1$-$C_6$ alkoxy)carbonyl group shown in Formula (I-1a and I-1b) (which can be manufactured according to any of the above Reaction Schemes 1-3), after manufacturing the carboxylic acid derivatives shown in (I-2a and I-2b) by deprotection of the ester group, the amide derivatives (I-3a and I-3b) can be manufactured by condensation with the amine compound shown in Formula (5) using a normal method.

Specifically, in the first step, conversion to the carboxylic acid derivatives shown in Formulae (I-2a, I-2b), which are obtained by deprotection of the ester groups of the derivatives shown in Formulae (I-1a, I-1b) is performed, depending on the nature of $R^6$, by carrying out the reaction, for example in the case of an alkyl group having 1 to 6 carbon atoms such as methyl, ethyl and n-propyl, in the presence of 0.5 to 10 moles and preferably 1 to 5 moles of a base such as lithium hydroxide, sodium hydroxide or potassium hydroxide, from −20° C. to 150° C., and preferably from 0° C. to 100° C., in a suitable solvent. The suitable solvent is not particularly limited provided that it does not affect the reaction, for example water, methanol, ethanol, n-propanol, isopropanol, tetrahydrofuran, dioxane, diethyl ether, isopropyl ether, N,N-dimethylformamide, N,N-dimethylacetamide, N-methylpyrrolidone and dimethyl sulfoxide may be mentioned, these being used independently or in admixture.

In the second step, the amide compound shown in the general equations (I-3a, I-3b) can be obtained by condensing the amino derivative shown in Formula (5) or a salt thereof, with the carboxylic acid derivative shown in Formulae (I-2a, I-2b) or a reactive derivative thereof by a normal method.

Examples of the reactive derivative of the compounds (I-2a, I-2b) are active esters such as acid halides, e.g., acid chlorides or acid bromides, acid azides, N-hydroxybenzotriazole, N-hydroxysuccimide or p-nitrophenol or the like, and mixed acid anhydrides such as symmetrical acid anhydrides, alkylcarboxylic acid or p-toluenesulfonic acid.

When reacting the carboxylic acid derivative shown in Formulae (I-2a, I-2b) or a reactive derivative thereof with a free acid, or when an active ester or acid halide are reacted without being isolated, a condensation agent such as dicyclohexyl carbodiimide, carbonyldiimadazole, diphenyl phosphorylazide, diethyl phosphorylazide, 1-ethyl-3-(3-dimethylaminopropyl)carbodiimide hydrochloride and 4-(4,6-dimethoxy-1,3,5-triazin-2-yl)-4-methylmorpholinium or the like may be used.

The reaction is carried out using 0.5 to 10 moles and preferably 0.8 to 5 moles of the amine derivative shown in Formula (5) or a salt thereof with respect to 1 mole of the carboxylic acid derivative shown in Formulae (I-2a, I-2b) or a reactive derivative thereof. If the above condensation agent is used, its amount is 0.5 to 20 moles and preferably 0.8 to 3 moles with respect to 1 mole of the carboxylic acid derivative shown in Formulae (I-2a, I-2b), or a reactive derivative thereof. Although dependent on the reactive derivative or condensation agent used, the reaction is normally carried out in a solvent that is inactive to the reaction, e.g., a halogenated hydrocarbon such as dichloroethane, chloroform and carbon tetrachloride, aromatic hydrocarbon such as benzene, toluene or xylene, an ether such as diethyl ether, tetrahydrofuran or dioxane, an ester such as ethyl acetate, an alcohol such as methanol, ethanol, n-propanol or isopropanol, water, acetonitrile, N,N-dimethylformamide, N,N-dimethylacetamide, dimethylsulfoxide, and pyridine, from −20° C. to 150° C., and preferably from 0° C. to 100° C.

The reaction may proceed more smoothly if it is carried out in the presence of 0.5 to 20 moles and preferably 0.8 to 5 moles of a base such as diisopropylethylamine, N-methylmorpholine, N,N-dimethylaniline, N,N-diethylaniline, 4-(N,N-dimethylamino)pyridine, pyridine, picoline, or lutidine, with respect to 1 mole of the carboxylic acid derivative shown in Formulae (I-2a, I-2b), or a reactive derivative thereof.

The amine compound shown in Formula (5) is known in the art, or may be obtained by a method known in the art.

The manufacturing intermediates and the compound of the invention thus obtained may be purified by the usual separation means known in synthetic chemistry of extraction, precipitation, suspension washing, recrystallization, distillation and column chromatography.

Pharmaceutical Composition

The compound shown in Formula (I) and salts thereof, can inhibit prostaglandin D synthase and in particular, hematopoietic synthase, and is therefore useful as a prostaglandin D synthase inhibitor and in particular, a hematopoietic prostaglandin D synthase inhibitor.

Therefore, the invention provides a pharmaceutical composition containing an effective dose of at least one of the compounds shown in Formula (I) or a pharmaceutically acceptable salt thereof, and a pharmaceutical carrier.

The invention further provides a compound shown in Formula (I) and salts thereof that can be used as a prostaglandin D synthase inhibitor and in particular, a hematopoietic prostaglandin D synthase inhibitor.

Thus, since it has a prostaglandin D synthase inhibitory effect, the compound shown in Formula (I) and salts thereof are useful in preventing or improving undesirable conditions caused by prostaglandin D2 originating from this enzyme, or its metabolites. In particular, the compound shown in Formula (I) and salts thereof have a hematopoietic synthase inhibitory effect, so a pharmaceutical composition containing this compound is useful in mammals, and especially man, as a preventive and/or therapeutic agent for allergy diseases, such as bronchial asthma, pollinosis, allergic rhinitis, sinusitis, otitis media, allergic conjunctivitis, spring catarrh, atopic dermatitis, contact dermatitis, and food allergies.

The compound shown in Formula (I) and salts thereof are useful as preventive and/or therapeutic agents for inflammatory diseases such as chronic obstructive pulmonary disease, interstitial pneumonia, hypersensitivity pneumonitis, eosinophilic pneumonia, articular rheumatism, degenerative arthritis, inflammatory bowel disease, skin diseases (psoriasis, eczema, erythema, itch syndrome, pimples etc.), muscular inflammation, muscular dystrophy, post-PTCA restenosis, reperfusion injury, and graft rejection reaction, although these are not exhaustive.

The compound shown in Formula (I) and salts thereof can be expected to prevent exacerbation of Alzheimer disease or brain damage, and/or improve the prognosis after brain damage.

Furthermore, the compound shown in Formula (I) and salts thereof are useful in improving the treatment and prevention of mucus secretion problems, reproductive problems, blood coagulation disorders, pain, vision problems, obesity, immunopathy and autoimmune diseases. Moreover, since it can inhibit cell neoplastic transformation and metastatic tumor growth, it is also useful in cancer therapy, and in the treatment and/or prevention of proliferative diseases due to prostaglandin D2 or its metabolites, such as fibroblast proliferation, diabetic retinopathy, and tumor angiogenesis. Furthermore, since it can suppress prostaglandin-D2-induced smooth muscle contraction, it can also be used in the treatment and/or prevention of infertility, dysmenorrhea, premature delivery, and eosinophile-leucocyte-related disorders.

To apply the compound of the invention or its salts to the treatment or prevention of the above diseases in mammals including humans, the dose is of course varied according to the state and severity of the disease to be treated, the type of compound shown in Formula (I), and its route of administration. Moreover, it varies also according to each patient's age, weight, overall state of health, sex, meals, administration time, excretion rate, concomitant use of other drugs, and response. In general, it may be administered orally or non-orally. In general, the dose is an amount effective in the treatment of the above disorders. For example, the daily dose is about 0.001 to approx. 100 mg and preferably 0.01 to 50 mg per kg of body weight of a mammal, including man. However, another dosage may be used depending on the case.

The compound of the invention or its salt may be administered orally or non-orally (for external use, inhalation, subcutaneous injection, arterial or intravenous injection, intramuscular injection, bladder instillation, intercranial instillation, nosedrops, eyedrops, eyewash, suppositories) by mixing an effective dose with a pharmaceutically permitted excipient in the form of a solid preparation such as a tablet, capsule, granule, powder; a liquid preparation such as a syrup or injection; or an external preparation such as an ointment, lotion, gel or cream.

As the pharmaceutically acceptable carrier, various conventional organic or inorganic carrier materials used as pharmaceutical preparation materials may be blended as an excipient, lubricant, binder or disintegrator in solid preparations; or as a solvent, solubilizing agent, suspending agent, isotonizing agent, buffer, soothing agent or painkiller in liquid preparations. Moreover, pharmaceutical preparation additives such as antiseptics, anti-oxidants, colorants, and sweeteners may also be used if required.

As a suitable example of an excipient, lactose, D-mannitol, starch, crystalline cellulose, and light anhydrous silicic acid may be mentioned. As a suitable example of a lubricant, magnesium stearate, calcium stearate, talc, or colloidal silica may be mentioned. As a suitable example of a binder, crystalline cellulose, soft white sugar, D-mannitol, dextrin, hydroxypropylcellulose, hydroxypropylmethyl cellulose, or polyvinylpyrrolidone may be mentioned. As a suitable example of a disintegrator, starch, carboxymethylcellulose, carboxymethyl-cellulose calcium, crosscarmellose sodium, or carboxymethyl starch sodium may be mentioned. As a suitable example of a solvent, water for injection, alcohol, propylene glycol, macrogol, sesame oil, or corn oil may be mentioned. As a suitable example of a solubilizing agent, polyethylene glycol, propylene glycol, D-mannitol, benzyl benzoate, ethanol, tris-aminomethane, cholesterol, triethanolamine, sodium carbonate, or sodium citrate may be mentioned. As a suitable example of a suspending agent, stearyl triethanolamine, sodium lauryl sulfate, lauryl aminopropionic acid, lecithin, benzalkonium chloride, benzethonium chloride or glycerin monostearate may be mentioned. As a suitable example of a surfactant, hydrophilic polymers such as polyvinyl alcohol, polyvinylpyrrolidone, carboxymethylcellulose sodium, methyl cellulose, hydroxymethylcellulose, hydroxyethylcellulose, or hydroxypropylcellulose may be mentioned. As a suitable example of a buffer, a buffer solution such as phosphate, acetate, carbonate, or citrate may be mentioned. As a suitable example of a soothing agent, benzyl alcohol may be mentioned. As a suitable example of a preservative, p-hydroxybenzoate esters, chlorobutanol, benzyl alcohol, phenethyl alcohol, dehydroacetic acid and sorbic acid may be mentioned. As a suitable example of an antioxidant, sulfites and ascorbates may be mentioned.

EXAMPLES

The present invention is described in detail below with reference to Examples, which are not intended to limit the scope of the invention.

In the following description, $^1$H-NMR spectra were measured using TMS (tetramethylsilane) as an internal standard, and the chemical shifts are indicated by δ (ppm). With respect to the chemical shifts, absorption patterns, coupling constants (J), and numbers of protons are indicated in parentheses.

The following symbols are used for absorption patterns: s=singlet, d=doublet, t=triplet, q=quartet, dd=double doublet, m=multiplet, br=broad, and brs=broad singlet.

Moreover, the following symbols are used for structural formulae of compounds: Me=methyl, Et=ethyl, and Ph=phenyl.

Example 1

5-Benzoyl-2-(2,4-dimethylfuran-3-yl)-benzimidazole (1)

2,4-Dimethylfuran-3-carboxylic acid (30 mg, 0.21 mmol) and 4-(4,6-dimethoxy-1,3,5-triazine-2-yl)-4-methylmorpholinium chloride (65 mg, 0.23 mmol) were added to a methanol (3 ml) solution of 3,4-diaminobenzophenone (43 mg, 0.19 mmol) and stirred overnight, and the solvent was concentrated at reduced pressure. A chloroform/methanol mixture (7:1) and a saturated sodium carbonate were added to the residue and stirred for 30 minutes, and then the mixture was extracted using a chloroform/methanol mixture (7:1). The combined organic layer was washed with a saturated sodium chloride and dried with anhydrous magnesium sulfate.

The residue obtained by concentration at reduced pressure was purified using medium pressure silica gel flash column chromatography (chloroform:methanol=99:1). The obtained adduct was dissolved in acetic acid (4 ml) and stirred at 80° C. overnight. The solution was allowed to cool to room temperature, and the residue obtained by concentration was purified using medium pressure silica gel flash column chromatography (chloroform:methanol=99:1) to afford 5-benzoyl-2-(2,4-dimethylfuran-3-yl)-benzimidazole (22 mg, 35%) as a brown solid.

Melting point: 203-208° C.
$^1$H-NMR (DMSO-d$_6$): δ (ppm) 2.22 (s, 3H), 2.55 (s, 3H), 7.34-7.93 (m, 9H), 8.05 (br, 1H).

Example 2

4-(5-Benzoylbenzimidazol-2-yl)-3,5-dimethylfuran-2-carboxamide (2)

Example 2 (1)

3,5-Dimethyl-4-ethoxycarbonylfuran-2-carboxylic acid (starting material for compound according to Example 2)

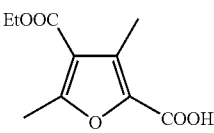

2,4-Dimethyl-5-formylfuran-3-carboxylic acid ethyl ester (1.78 g, 9.1 mmol) reported in the references was dissolved in a mixture of acetic acid (32 ml) and water (8 ml). Amidosulfuric acid (1.19 g, 12.2 mmol) was added to the solution, and cooled to 0° C. in an ice bath. Sodium chlorite was added and stirred for 2 hours, and after addition of water to reaction mixture, precipitate was collected by filtration, thereby giving 3,5-dimethyl-4-ethoxycarbonylfuran-2-carboxylic acid (1.01 g, 52%) as a white solid.

$^1$H-NMR (CDCl$_3$): δ (ppm) 1.38 (t, J=7.3 Hz, 3H), 2.56 (s, 3H), 2.64 (s, 3H), 4.33 (q, J=7.3 Hz, 2H).

Example 2 (2)

3,5-Dimethyl-4-ethoxycarbonylfuran-2-carboxamide (intermediate for compound according to Example 2)

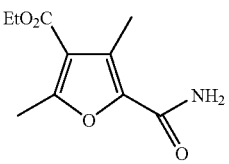

1-Ethyl-3-(3-dimethylaminopropyl)carbodiimide hydrochloride (248 mg, 1.30 mmol) and 1-hydroxybenzotriazole monohydrate (199 mg, 1.30 mmol) were added to a pyridine (4 ml) solution of the 3,5-dimethyl-4-ethoxycarbonylfuran-2-carboxylic acid (250 mg, 1.18 mmol) obtained in Example 2 (1). After a 28% aqueous ammonia solution (0.19 ml, 11.8 mmol) was added, heated to 80° C. and stirred for 4 hours. The mixture was cooled to room temperature with stirring, and after addition of water to reaction mixture, precipitate was collected by filtration, thereby giving 3,5-dimethyl-4-ethoxycarbonylfuran-2-carboxamide (176 mg, 71%) as a white solid.

$^1$H-NMR (CDCl$_3$): δ (ppm) 1.37 (t, J=7.0 Hz, 3H), 2.56 (s, 3H), 2.59 (s, 3H), 4.32 (q, J=7.0 Hz, 2H).

Example 2 (3)

4-(5-Benzoylbenzimidazol-2-yl)-3,5-dimethylfuran-2-carboxamide (2)

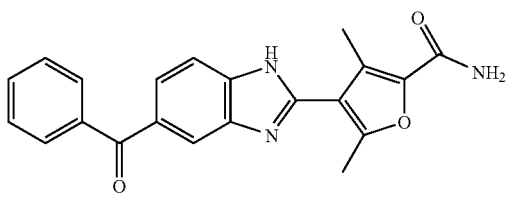

The 3,5-dimethyl-4-ethoxycarbonylfuran-2-carboxamide (176 mg, 0.83 mmol) obtained in Example 2 (2) was dissolved in ethanol (4 ml), and 0.13 ml of a 4 N sodium hydroxide aqueous solution was added and stirred at 75° C. for 4 hours. The solution was neutralized with 1 N hydrochloric acid at room temperature, and after the evaporation, a precipitate (crude carboxylic acid) was collected by filtration and used directly for the subsequent reaction.

The crude carboxylic acid (39 mg, 0.21 mmol) and 4-(4,6-dimethoxy-1,3,5-triazine-2-yl)-4-methylmorpholinium chloride (65 mg, 0.23 mmol) were added to a methanol (3 ml) solution of 3,4-diaminobenzophenone (43 mg, 0.19 mmol) and stirred overnight, and the solvent was concentrated at reduced pressure. A chloroform/methanol mixture (7:1) and a saturated sodium carbonate were added to the residue and stirred for 30 minutes, and then the mixture was extracted using a chloroform/methanol mixture (7:1). The combined organic layer was washed with a saturated sodium chloride and dried with anhydrous magnesium sulfate.

The residue obtained by concentration at reduced pressure was purified using medium pressure silica gel flash column chromatography (chloroform:methanol=99:1). The obtained adduct was dissolved in acetic acid (4 ml) and stirred at 80° C. overnight. The solution was allowed to cool to room temperature, and the residue obtained by concentration was purified using medium pressure silica gel flash column chromatography (chloroform:methanol=99:1) to afford 4-(5-benzoylbenzimidazol-2-yl)-3,5-dimethylfuran-2-carboxamide (42 mg, 62%) as a yellow solid.

Melting point: 143-146° C.

$^1$H-NMR (CDCl$_3$): δ (ppm) 2.67 (s, 3H), 2.72 (s, 3H), 5.76-6.22 (br, 2H), 7.85-7.47 (m, 9H).

Example 3

(4-(5-Benzoylbenzimidazol-2-yl)-3,5-dimethyl-2-furanylcarbonyl)pyrrolidine (3)

Example 3 (1)

(3,5-Dimethyl-4-ethoxycarbonyl-2-furanylcarbonyl)pyrrolidine (starting material for compound according to Example 3)

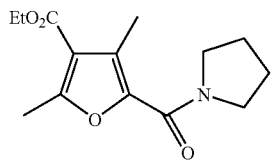

Following the procedure of Example 2 (2) using pyrrolidine instead of 28% aqueous ammonia, (3,5-dimethyl-4-ethoxycarbonyl-2-furanylcarbonyl)pyrrolidine (89%) was obtained as a white solid.

$^1$H-NMR (CDCl$_3$): δ (ppm) 1.37 (t, J=7.3 Hz, 3H), 1.92 (br, 4H), 2.49 (s, 3H), 2.57 (s, 3H), 3.62-3.73 (m, 4H), 4.31 (q, J=7.3 Hz, 2H).

Example 3 (2)

(4-(5-Benzoylbenzimidazol-2-yl)-3,5-dimethyl-2-furanylcarbonyl)pyrrolidine (3)

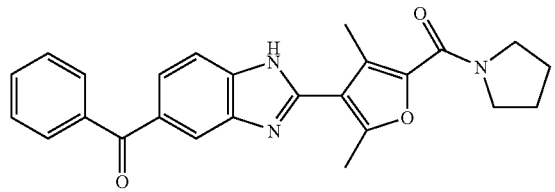

Following the procedure of Example 2 (3) using (3,5-dimethyl-4-ethoxycarbonyl-2-furanylcarbonyl)pyrrolidine instead of 3,5-dimethyl-4-ethoxycarbonylfuran-2-carboxamide, (4-(5-benzoylbenzimidazol-2-yl)-3,5-dimethyl-2-furanylcarbonyl)pyrrolidine (59%) was obtained as a light yellow solid.

Melting point: 112-114° C.

$^1$H-NMR (DMSO-d$_6$): δ (ppm) 1.85 (br, 4H), 2.44, 2.46 (s and s, total 3H), 2.58, 2.60 (s and s, total 3H), 3.46 (br, 2H), 3.74 (br, 2H), 7.42-7.99 (m, 8H), 12.56, 12.67 (s and s, total 1H).

Example 4

N-(3,4-Methylenedioxyphenyl)methyl-4-(5-benzoyl-benzimidazol-2-yl)-3,5-dimethylfuran-2-carboxamide (4)

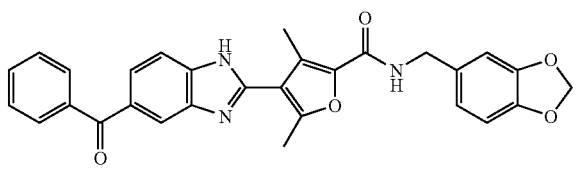

Following the procedure of Example 3 using piperonylamine instead of pyrrolidine, N-(3,4-methylenedioxyphenyl)methyl-4-(5-benzoylbenzimidazol-2-yl)-3,5-dimethylfuran-2-carboxamide (87 mg, 87%) was obtained as a light yellow solid.

Melting point: 122-125° C.

$^1$H-NMR (DMSO-d$_6$): δ (ppm) 2.51, 2.53 (s and s, total 3H), 2.58, 2.61 (s and s, total 3H), 4.28-4.32 (m, 2H), 5.97 (s, 2H), 6.75-6.89 (m, 3H), 7.42-7.99 (m, 8H), 8.71 (brs, 1H), 12.57, 12.68 (s and s, total 1H).

Example 5

4-(5-Benzoylbenzimidazol-2-yl)-pyrrole-2-carboxylic acid (5)

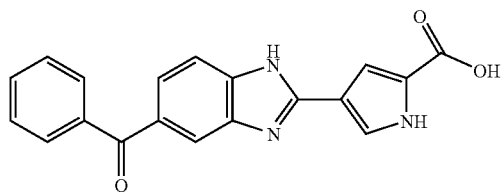

Pyrrole-2-carboxylic acid ethyl ester (3.0 g) was added ethanol (45 ml), nitromethane (45 ml), and aluminium chloride (7.2 g), and then α,α-dichloromethyl methyl ether (3.2 g) was added dropwise while cooling with ice. The resultant mixture was allowed to stand at −20° C. overnight. After the starting material was disappeared, the mixture was extracted with diethylether and water. The combined organic layer was concentrated at reduced pressure, and dried in vacuo. The obtained solid was dissolved in N,N-dimethylformamide (20 ml), and the solution was slowly added dropwise to an N,N-dimethylformamide solution (30 ml) of 3,4-diaminobenzophenone (4.6 g) and sodium hydrogensulfite (2.9 g) at 130° C. After heating at 130° C. for 5 hours, the reaction mixture was cooled to room temperature, and added to water and stirred. The precipitate was collected by filtration, and dried in vacuo.

The obtained solid was dissolved in tetrahydrofuran (10 ml) and ethanol (10 ml), and then a 4 N sodium hydroxide aqueous solution (15 ml) was added and heated under reflux for 4 hours. After the starting material was disappeared, the reaction mixture was cooled to room temperature, and then neutralized with a hydrochloric acid solution. The precipitate was collected by filtration, and heated and dried in vacuo to afford 4-(5-benzoylbenzimidazol-2-yl)-pyrrole-2-carboxylic acid (5.3 g, 75%) as a light yellow solid.

Melting point: 239-241° C.

$^1$H-NMR (DMSO-d$_6$): δ (ppm): 7.40 (d, J=1.6 Hz, 1H), 7.55-7.77 (m, 8H), 7.87 (s, 1H), 12.3 (br, 1H).

Example 6

((4-(5-Benzoylbenzimidazol-2-yl)-pyrrol-2-yl)-carbonyl)pyrrolidine (6)

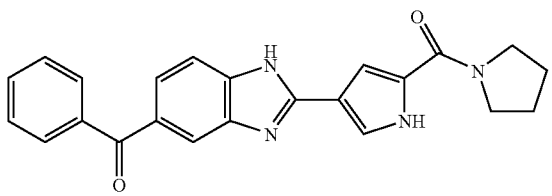

The 4-(5-benzoylbenzimidazol-2-yl)-pyrrole-2-carboxylic acid (130 mg) obtained in Example 5 was dissolved in N,N-dimethylformamide (2 ml) and pyridine (2 ml). Pyrrolidine (56 mg), 1-ethyl-3-(3-dimethylaminopropyl)carbodiimide hydrochloride (112 mg), and 1-hydroxybenzotriazole monohydrate (80 mg) were added and stirred overnight at 80° C. After the starting material was disappeared, the reaction mixture was allowed to cool to room temperature, and then added dropwise to water. The precipitate was collected by filtration, and dried in vacuo to afford ((4-(5-benzoylbenzimidazol-2-yl)-pyrrol-2-yl)-carbonyl)pyrrolidine (118 mg, 78%) as a red solid.

Melting point: 160-162° C.

$^1$H-NMR (DMSO-d$_6$): δ (ppm) 1.86-2.04 (m, 4H), 3.48-3.92 (m, 4H), 7.28 (s, 1H), 7.55-7.77 (m, 9H), 12.0 (br, 1H), 12.8 (br, 1H)

Example 7

2-(2,4-Dimethyl-pyrrol-3-yl)-5-benzoylbenzimidazole (7)

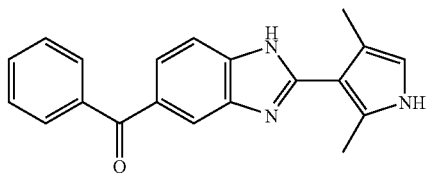

3,4-Diaminobenzophenone (1.48 g) and sodium hydrogensulfite (0.87 g) were added to N,N-dimethylacetamide (5 ml) at 130° C., and stirred for 5 minutes. 2,4-Dimethyl-3-formyl-pyrrole (1.03 g) was added and stirred at 130° C. for 8 hours. The reaction mixture was cooled to room temperature and stirred, and after addition of water to reaction mixture, precipitate was collected by filtration, and dried in vacuo to afford 2-(2,4-dimethyl-pyrrol-3-yl)-5-benzoylbenzimidazole (1.78 g, 81%) as a brown solid.

Melting point: 207-214° C.

$^1$H-NMR (DMSO-$d_6$): δ (ppm) 2.22 (s, 3H), 2.37 (s, 3H), 5.79 (s, 1H), 7.55-7.88 (m, 8H), 11.15 (s, 1H), 12.97 (s, 1H).

Example 8

2-(2-Formyl-3,5-dimethyl-pyrrol-4-yl)-5-benzoyl-benzimidazole (8)

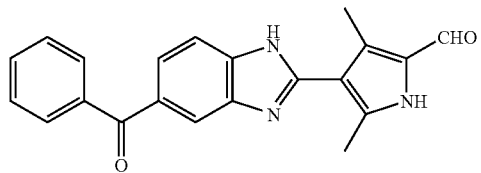

Phosphoryl chloride (2.43 g) was slowly added dropwise to N,N-dimethylformamide (15.9 g) at room temperature, and stirred at room temperature for 30 minutes. To this mixture, an N,N-dimethylformamide solution of the 2-(2,4-dimethyl-pyrrol-3-yl)-5-benzoylbenzimidazole (2.5 g) obtained in Example 7 was slowly added dropwise. After stirring for 2 hours, 50 ml of a 1 N sodium hydroxide aqueous solution was added, heated to 80° C., and stirred for 2 hours. After the starting material was disappeared, reaction mixture was slowly added to water, and precipitate was collected by filtration. The solid was dried in vacuo to afford 2-(2-formyl-3,5-dimethyl-pyrrol-4-yl)-5-benzoylbenzimidazole (1.63 g, 60%) as a brown solid.

Melting point: 253-255° C.

$^1$H-NMR (DMSO-$d_6$): δ (ppm) 2.53 (s, 3H), 2.57 (s, 3H), 7.54-7.80 (m, 7H), 7.93 (s, 1H), 9.66 (s, 1H), 12.30 (br, 1H).

Example 9

2-(2-Acrylonitrile-3,5-dimethyl-pyrrol-4-yl)-5-benzoylbenzimidazole (9)

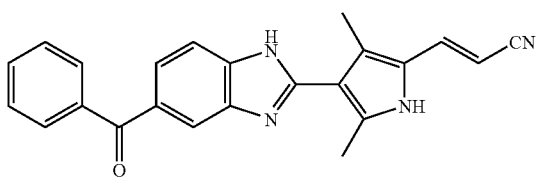

The 2-(2-formyl-3,5-dimethyl-pyrrol-4-yl)-5-benzoyl-benzimidazole (105 mg) obtained in Example 8 was dissolved in tetrahydrofuran (2 ml). Diethyl cyanomethyl phosphonate (54 mg) and sodium methoxide (33 mg) were added and stirred at room temperature for 1 hour. Additional diethyl cyanomethyl phosphonate (54 mg) was added and heated at 60° C. for 4 hours. The reaction mixture was neutralized with a 0.1 N hydrochloric acid solution, and then the resultant mixture was extracted with chloroform (5 ml) and washed with water (2 ml). The resultant organic layer was concentrated, and the residue was purified using medium pressure silica gel flash column chromatography (chloroform:ethyl acetate=1:1), and dried in vacuo to afford 2-(2-acrylonitrile-3,5-dimethyl-pyrrol-4-yl)-5-benzoylbenzimidazole (61.6 mg, 55%) as a light yellow solid.

Melting point: 201-203° C.

$^1$H-NMR (DMSO-$d_6$): δ (ppm) 2.36 (s, 3H), 2.54 (s, 3H), 5.79 (d, J=16.0 Hz, 1H), 7.48-7.98 (m, 10H), 11.85 (s, 1H).

Example 10

4-(5-Benzoylbenzimidazol-2-yl)-3,5-dimethylpyrrole-2-carboxylic acid (10)

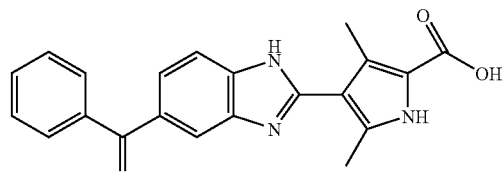

Sodium hydrogensulfite (1.0 g) and 3,5-dimethyl-4-formylpyrrole-2-carboxylic acid ethyl ester (1.5 g) were added to an N,N-dimethylacetamide (20 ml) solution of 3,4-diaminobenzophenone (1.6 g), and the mixture was heated to 120° C. and stirred for 10 hours. After the mixture was allowed to cool to room temperature, a 5% sodium carbonate (60 g) was added and stirred at room temperature, and the precipitate was collected by filtration and washed with water. The obtained solid was dissolved in ethanol (15 ml) and tetrahydrofuran (15 ml), and a 4 N sodium hydroxide aqueous solution (20 ml) was added and heated under reflux for 12 hours. After the starting material was disappeared, the reaction mixture was allowed to cool to room temperature, and neutralized with a 1 N hydrochloric acid solution. The precipitate was collected by filtration to afford 4-(5-benzoylbenzimidazol-2-yl)-dimethylpyrrole-2-carboxylic acid (2.3 g, 90%) as a light yellow solid.

Melting point: 192-194° C.

$^1$H-NMR (DMSO-$d_6$): δ (ppm) 2.49 (s, 3H), 2.55 (s, 3H), 7.49-8.01 (m, 8H), 11.63 (brs, 1H), 11.68-12.57 (br, 1H).

Example 11

N-Methyl-N-(2-dimethylaminoethyl)-4-(5-benzoyl-benzimidazol-2-yl)-3,5-dimethylpyrrole-2-carboxa-mide (11)

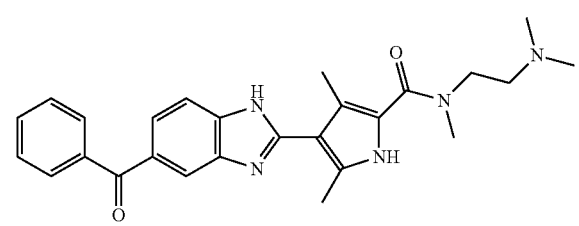

1-Ethyl-3-(3-dimethylaminopropyl)carbodiimide hydrochloride (88 mg, 0.46 mmol) and 1-hydroxybenzotriazole monohydrate (70 mg, 0.46 mmol) were added to a pyridine (2 ml) solution of the 4-(5-benzoylbenzimidazol-2-yl)-3,5-dimethylpyrrole-2-carboxylic acid (150 mg, 0.42 mmol) obtained in Example 10. N,N,N'-Trimethyl ethylenediamine (43 mg, 0.42 mmol) was added to the resultant solution and heated. The reaction mixture was stirred for 5 hours at 60° C. (internal temperature), and then allowed to cool to room temperature. The solvent was evaporated, and the residue was purified using medium pressure silica gel flash column chromatography (NH silica gel, chloroform:methanol=98:2) to afford N-methyl-N-(2-dimethylaminoethyl-4-(5-benzoylbenzimidazol-2-yl)-3,5-dimethylpyrrole-2-carboxamide (112 mg, 61%) as a light yellow amorphous.

$^1$H-NMR (DMSO-$d_6$): δ (ppm) 2.17 (s, 6H), 2.30 (s, 3H), 2.45, 2.47 (s and s, total 3H), 2.95-2.99 (m, 2H), 2.99 (s, 3H), 3.51 (t, J=4.3 Hz, 2H), 7.56-7.89 (m, 8H), 7.89 (brs, 1H), 12.00, 12.14 (brs and brs, total 1H).

Example 12

4-(5-Benzoylbenzimidazol-2-yl)-3,5-dimethylpyrrole-2-carboxamide (12)

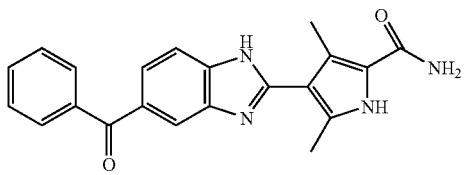

Following the procedure of Example 11 using a 7 N ammonia in methanol solution of instead of N,N,N'-trimethylethylenediamine, 4-(5-benzoylbenzimidazol-2-yl)-3,5-dimethylpyrrole-2-carboxamide (55%) was obtained as a dark brown solid.

Melting point: 188-190° C.

$^1$H-NMR (DMSO-$d_6$): δ (ppm) 2.47 (s, 3H), 2.49 (s, 3H), 6.99 (br, 2H), 7.54-7.77 (m, 7H), 7.91 (s, 1H), 11.4 (s, 1H), 12.02-12.39 (br 1H).

Example 13

2-(2-Cyano-3,5-dimethyl-pyrrol-4-yl)-5-benzoylbenzimidazole (13)

Example 13 (1)

5-Cyano-2,4-dimethylpyrrole-3-carboxyaldehyde

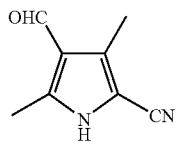

Phosphorus oxychloride (10.2 ml, 110 mmol) was added dropwise to N,N-dimethylformamide (8.04 g, 110 mmol) and stirred for 1 hour. An N,N-dimethylformamide (25 ml) solution of 2-cyano-3,5-dimethylpyrrole (12.0 g, 100 mmol) reported in Synthesis, 1999, 46 was added dropwise over a period of 30 minutes. After stirring for 3 hours, the mixture was poured into iced water (approximately 500 g) and neutralized with solid sodium hydrogencarbonate. The reaction mixture was extracted with ethyl acetate, and washed with water and a saturated sodium chloride. The combined organic layer was dried with anhydrous sodium sulfate. The desiccant was filtered off, and the residue obtained by evaporation at reduced pressure was purified using medium pressure silica gel flash column chromatography (ethyl acetate:chloroform=1:20 to 1:5) to afford 5-cyano-2,4-dimethylpyrrole-3-carboxyaldehyde (7.96 g, 54%) as a light yellow solid.

Melting point: 208-210° C.

$^1$H-NMR (CDCl$_3$): δ (ppm) 2.46 (s, 3H), 2.57 (s, 3H), 9.10 (brs, 1H), 9.97 (s, 1H).

Example 13 (2)

2-(2-Cyano-3,5-dimethyl-pyrrol-4-yl)-5-benzoylbenzimidazole (13)

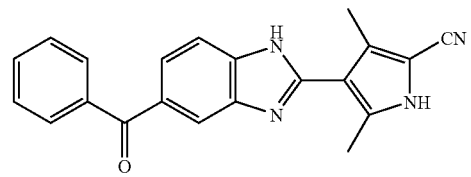

3,4-Diaminobenzophenone (6.37 g, 30 mmol) was dissolved in N,N-dimethylacetamide (90 ml), and then sodium hydrogensulfite (3.43 g, 33 mmol) was added to the solution. While heating the mixture to 130° C. with stirring, an N,N-dimethylacetamide (20 ml) solution of the 5-cyano-2,4-dimethylpyrrole-3-carboxyaldehyde (4.89 g, 33 mmol) obtained in Example 13 (1) was added dropwise. The reaction mixture was stirred at 130° C. for 12 hours, and then water and a saturated sodium hydrogencarbonate were added to the residue obtained by evaporation at reduced pressure. The precipitate was collected by filtration, washed with water and diethylether, and dried in vacuo. The obtained crude solid was purified using medium pressure silica gel flash column chromatography (methanol:chloroform=1:50 to 1:15) to afford 2-(2-cyano-3,5-dimethyl-pyrrol-4-yl)-5-benzoylbenzimidazole (7.85 g, 77%) as a light yellow solid.

Melting point: 159-163° C.

$^1$H-NMR (DMSO-$d_6$): δ (ppm) 2.41 (s, 3H), 2.52 (s, 3H), 7.52-7.98 (m, 8H), 12.12-12.48 (br, 2H).

Example 14

N-(Methoxy)-4-(5-benzoylbenzimidazol-2-yl)-3,5-dimethylpyrrole-2-carboxamide (14)

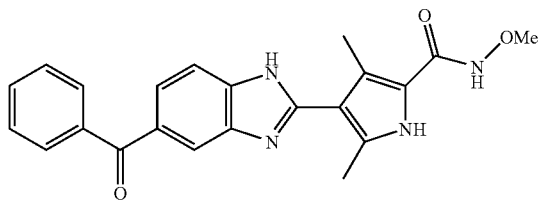

Following the procedure of Example 11 using O-methylhydroxylamine hydrochloride instead of N,N,N'-trimethylethylenediamine, N-(methoxy)-4-(5-benzoylbenzimidazol-2-yl)-3,5-dimethylpyrrole-2-carboxamide (60%) was obtained as a dark brown solid.

Melting point: 203-205° C.

$^1$H-NMR: (DMSO-$d_6$): δ (ppm) 2.45, 2.45, 2.47, 2.48 (s and s and s and s, total 6H), 3.71 (s, 3H), 7.56-7.95 (m, 8H), 10.75, 10.77 (s and s, total 1H), 11.46, 11.50 (s and s, total 1H), 12.14, 12.28 (s and s, total 1H).

Example 15

(N-Methoxy-N-methyl)-4-(5-benzoylbenzimidazol-2-yl)-3,5-dimethylpyrrole-2-carboxamide (15)

Example 15 (1)

3,5-Dimethyl-4-formylpyrrole-2-carboxylic acid

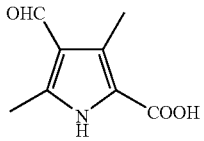

3,5-Dimethyl-4-formylpyrrole-2-carboxylic acid ethyl ester (19.52 g, 100 mmol) reported in the references was suspended in ethanol (100 ml) and a 2 N sodium hydroxide aqueous solution (100 ml, 200 mmol), and then stirred for 4 hours under reflux condition. After the completion of the reaction, 200 ml of water and 100 ml of a 2 N hydrochloric acid aqueous solution were added under the ice cooled. The precipitate was collected by filtration, washed with water and diethylether, and dried at reduced pressure to afford 3,5-dimethyl-4-formylpyrrole-2-carboxylic acid (16.18 g, 97%) as a light brown solid.

Melting point: 233-237° C.
$^1$H-NMR (DMSO-$d_6$): δ (ppm) 2.45 (s, 3H), 2.48 (s, 3H), 9.90 (s, 1H), 11.95 (brs, 1H), 12.58 (br, 1H).

Example 15 (2)

(N-Methoxy-N-methyl)-3,5-dimethyl-4-formylpyrrole-2-carboxamide

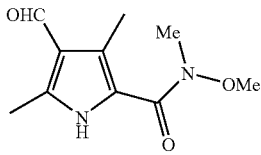

The 3,5-dimethyl-4-formylpyrrole-2-carboxylic acid (10.0 g, 60 mmol) obtained in Example 15 (1) was suspended in N,N-dimethylformamide (120 ml). To this suspension were added 1-hydroxybenzotriazole monohydrate (9.65 g, 63 mmol), 1-ethyl-3-(3-dimethylaminopropyl)carbodiimide hydrochloride (12.65 g, 66 mmol), N,O-dimethylhydroxylamine hydrochloride (7.02 g, 72 mmol), and triethylamine (12.6 ml, 90 mmol) under the ice cooled, and stirred at room temperature for 16 hours. Water was added to the reaction mixture, and the solution was extracted with ethyl acetate. The extract was washed with a saturated sodium hydrogencarbonate, water, and a saturated sodium chloride, and then dried with anhydrous sodium sulfate. The desiccant was filtered off, and the residue obtained by evaporation at reduced pressure was purified using medium pressure silica gel flash column chromatography (ethyl acetate:chloroform=1:10 to 1:3) to afford (N-methoxy-N-methyl)-3,5-dimethyl-4-formylpyrrole-2-carboxamide (6.32 g, 50%) as a light yellow solid.

Melting point: 129-131° C.
$^1$H-NMR (CDCl$_3$): δ (ppm) 2.55 (s, 3H), 2.57 (s, 3H), 3.34 (s, 3H), 3.70 (s, 3H), 9.43 (brs, 1H), 10.04 (s, 1H).

Example 15 (3)

(N-Methoxy-N-methyl)-4-(5-benzoylbenzimidazol-2-yl)-3,5-dimethylpyrrole-2-carboxamide (15)

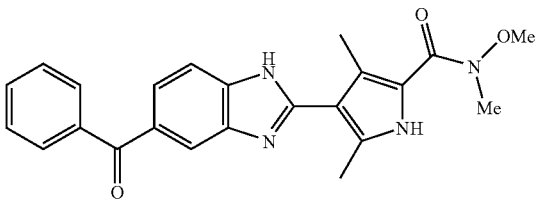

3,4-Diaminobenzophenone (5.31 g, 25 mmol) was dissolved in N,N-dimethylacetamide (70 ml), and sodium hydrogensulfite (2.86 g, 27.5 mmol) was added to the solution. While heating the mixture to 130° C. with stirring, an N,N-dimethylacetamide (15 ml) solution of the (N-methoxy-N-methyl)-3,5-dimethyl-4-formylpyrrole-2-carboxamide (5.78 g, 27.5 mmol) obtained in Example 15 (2) was added dropwise. The reaction mixture was stirred at 130° C. for 16 hours, and then water and a saturated sodium hydrogencarbonate were added to the residue obtained by evaporation at reduced pressure. The precipitate was collected by filtration, washed with water and diethylether, and then dried in vacuo. The obtained crude solid was purified using medium pressure silica gel flash column chromatography (methanol:chloroform=1:100 to 1:20) to afford (N-methoxy-N-methyl)-4-(5-benzoylbenzimidazol-2-yl)-3,5-dimethylpyrrole-2-carboxamide (7.25 g, 72%) as a light yellow solid.

Melting point: 127-132° C.
$^1$H-NMR (DMSO-$d_6$): δ (ppm) 2.43 (s, 3H), 2.50 (s, 3H), 3.26 (s, 3H), 3.63 (s, 3H), 7.50-8.00 (m, 8H), 11.31 (brs, 1H), 12.20 (br, 1H).

Example 16

N-(3-Methoxypropyl)-4-(5-benzoylbenzimidazol-2-yl)-3,5-dimethylpyrrole-2-carboxamide (16)

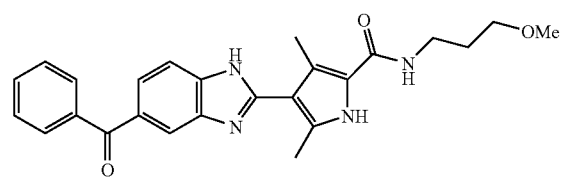

Following the procedure of Example 11 using 3-methoxypropylamine instead of N,N,N'-trimethylethylenediamine, N-(3-methoxypropyl)-4-(5-benzoylbenzimidazol-2-yl)-3,5-dimethylpyrrole-2-carboxamide (61%) was obtained as a white solid.

Melting point: 256-258° C.
$^1$H-NMR (DMSO-$d_6$): δ (ppm) 1.73-1.79 (m, 2H), 2.48 (s, 3H), 2.50 (s, 3H), 3.26 (s, 3H), 3.28-3.33 (m, 2H), 3.41 (t, J=6.5 Hz, 2H), 7.42 (br, 1H), 7.59-7.93 (m, 8H), 11.37 (brs, 1H), 12.09, 12.24 (brs and brs, total 1H).

Example 17

N-(3-Dimethylaminopropyl)-4-(5-benzoylbenzimidazol-2-yl)-3,5-dimethylpyrrole-2-carboxamide (17)

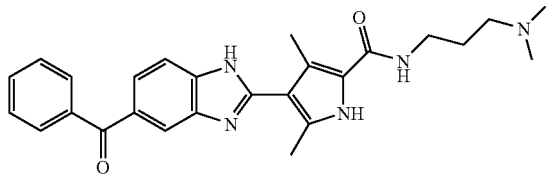

Following the procedure of Example 11 using N,N-dimethyl-1,3-propanediamine instead of N,N,N'-trimethylethylenediamine, N-(3-dimethylaminopropyl)-4-(5-benzoylbenzimidazol-2-yl)-3,5-dimethylpyrrole-2-carboxamide (51%) was obtained as a white solid.
Melting point: 238-248° C.
$^1$H-NMR (DMSO-$d_6$): δ (ppm) 1.63-1.69 (m, 2H), 2.16 (s, 6H), 2.31 (t, J=7.1 Hz, 2H), 2.45 (s, 3H), 2.47 (s, 3H), 3.27-3.32 (m, 2H), 7.54-7.93 (m, 9H), 11.38 (s, 1H), 12.10, 12.24 (s and s, total 1H).

Example 18

N-(2-Acetamidoethyl)-4-(5-benzoylbenzimidazol-2-yl)-3,5-dimethylpyrrole-2-carboxamide (18)

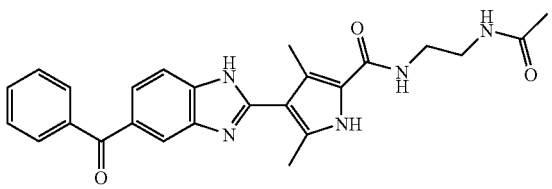

Following the procedure of Example 11 using N-acetylethylenediamine instead of N,N,N'-trimethylethylenediamine, N-(2-acetamidoethyl)-4-(5-benzoylbenzimidazol-2-yl)-3,5-dimethylpyrrole-2-carboxamide (67%) was obtained as a white solid.
Melting point: 272-273° C.
$^1$H-NMR (DMSO-$d_6$): δ (ppm) 1.82 (s, 3H), 2.45 (s, 3H), 2.50 (s, 3H), 3.20-3.23 (m, 2H), 3.29-3.32 (m, 2H), 7.46-7.98 (m, 10H), 11.35, 11.39 (brs and brs, total 1H), 12.10, 12.25 (s and s, total 1H).

Example 19

N-(2-Ethoxycarbonylethyl)-4-(5-benzoylbenzimidazol-2-yl)-3,5-dimethylpyrrole-2-carboxamide (19)

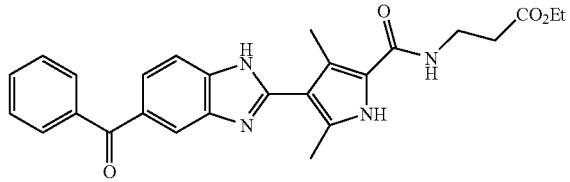

Following the procedure of Example 11 using β-alanine ethyl ester hydrochloride instead of N,N,N'-trimethylethylenediamine, N-(2-ethoxycarbonylethyl)-4-(5-benzoylbenzimidazol-2-yl)-3,5-dimethylpyrrole-2-carboxamide (65%) was obtained as a purple solid.
Melting point: 135-137° C.
$^1$H-NMR (DMSO-$d_6$): δ (ppm) 1.20 (t, J=7.3 Hz, 3H), 2.47 (s, 3H), 2.50 (s, 3H), 2.58 (t, J=6.8 Hz, 2H), 3.48-3.50 (m, 2H), 4.09 (q, J=7.0 Hz, 2H), 7.36-7.98 (m, 10H), 11.4 (br, 1H).

Example 20

N-(1-Methoxycarbonylmethyl)-4-(5-benzoylbenzimidazol-2-yl)-3,5-dimethylpyrrole-2-carboxamide (20)

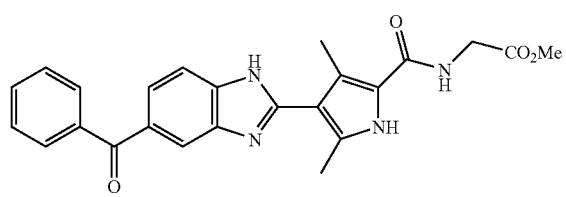

Following the procedure of Example 11 using a glycine methyl ester hydrochloride instead of N,N,N'-trimethylethylenediamine, N-(1-methoxycarbonylmethyl)-4-(5-benzoylbenzimidazol-2-yl)-3,5-dimethylpyrrole-2-carboxamide (65%) was obtained as a purple solid.
Melting point: 149-151° C.
$^1$H-NMR (DMSO-$d_6$): δ (ppm) 2.48 (s, 3H), 2.51 (s, 3H), 3.67 (s, 3H), 4.03 (d, J=5.9 Hz, 2H), 7.37-8.02 (m, 9H), 11.55 (br, 1H).

Example 21

N-(2-Carboxyethyl)-4-(5-benzoylbenzimidazol-2-yl)-3,5-dimethylpyrrole-2-carboxamide (21)

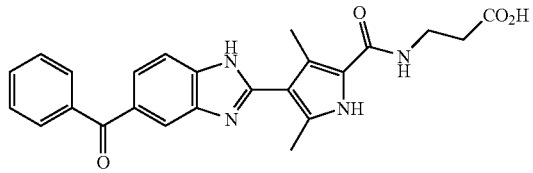

The N-(2-ethoxycarbonylethyl)-4-(5-benzoylbenzimidazol-2-yl)-3,5-dimethylpyrrole-2-carboxamide (300 mg) obtained in Example 19 was dissolved in tetrahydrofuran (5 ml) and ethanol (5 ml), and a 4 N sodium hydroxide aqueous solution (10 ml) was added to the solution and stirred at room temperature for 1 hour. The reaction mixture was neutralized with a 4 N hydrochloric acid solution, and then the precipitate was collected by filtration. The solid was dried in vacuo to afford N-(2-carboxyethyl)-4-(5-benzoylbenzimidazol-2-yl)-3,5-dimethylpyrrole-2-carboxamide (211 mg, 75%) as a purple solid.

Melting point: 256-258° C.

¹H-NMR (DMSO-d₆): δ (ppm) 2.40-2.50 (m, 2H), 2.47 (s, 3H), 2.50 (s, 3H), 3.38-3.53 (m, 2H), 7.54-7.95 (m, 10H), 11.60 (br, 1H).

Example 22

N-(1-Carboxymethyl)-4-(5-benzoylbenzimidazol-2-yl)-3,5-dimethylpyrrole-2-carboxamide (22)

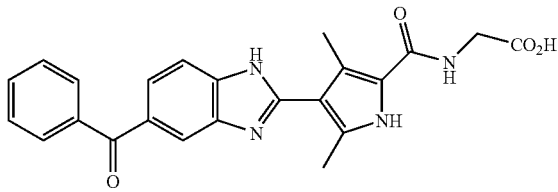

Following the procedure of Example 21 using N-(1-methoxycarbonylmethyl)-4-(5-benzoylbenzimidazol-2-yl)-3,5-dimethylpyrrole-2-carboxamide instead of N-(2-ethoxycarbonylethyl)-4-(5-benzoylbenzimidazol-2-yl)-3,5-dimethylpyrrole-2-carboxamide, N-(1-carboxymethyl)-4-(5-benzoylbenzimidazol-2-yl)-3,5-dimethylpyrrole-2-carboxamide (67%) was obtained as a purple solid.

Melting point: 274-276° C.

¹H-NMR (DMSO-d₆): δ (ppm) 2.47 (s, 3H), 2.54 (s, 3H), 3.79 (brs, 2H), 7.55-7.97 (m, 10H), 11.9 (br, 1H).

Example 23

N-(2-Pyrrolidine-1-yl-ethyl)-4-(5-benzoylbenzimidazol-2-yl)-3,5-dimethylpyrrole-2-carboxamide (23)

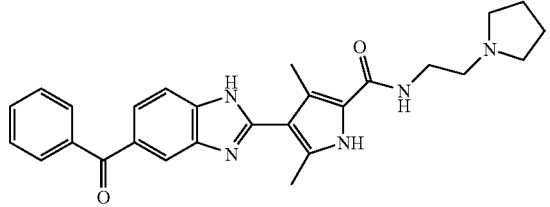

Following the procedure of Example 11 using 1-(2-aminoethyl)-pyrrolidine instead of N,N,N'-trimethylethylenediamine, N-(2-pyrrolidine-1-yl-ethyl)-4-(5-benzoylbenzimidazol-2-yl)-3,5-dimethylpyrrole-2-carboxamide (43%) was obtained as a light yellow amorphous.

¹H-NMR (CDCl₃): δ (ppm) 1.70 (br, 4H), 2.23 (s, 3H), 2.29 (s, 3H), 2.57 (br, 4H), 2.71 (br, 2H), 3.48 (br, 2H), 6.96 (br, 1H), 7.46-8.19 (m, 9H), 10.36 (s, 1H).

Example 24

N-(2-Piperidine-1-yl-ethyl)-4-(5-benzoylbenzimidazol-2-yl)-3,5-dimethylpyrrole-2-carboxamide (24)

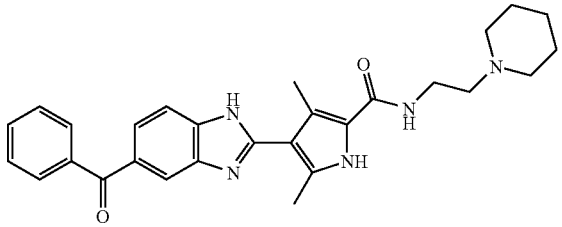

Following the procedure of Example 11 using 1-(2-aminoethyl)-piperidine instead of N,N,N'-trimethylethylenediamine, N-(2-piperidine-1-yl-ethyl)-4-(5-benzoylbenzimidazol-2-yl)-3,5-dimethylpyrrole-2-carboxamide (71%) was obtained as a white solid.

Melting point: 230-237° C.

¹H-NMR (DMSO-d₆): δ (ppm) 1.39 (br, 2H), 1.51 (br, 4H), 2.40-2.50 (m, 5H), 2.97-3.00 (m, 1H), 3.32-3.37 (m, 2H), 7.27 (br, 1H), 7.56-7.93 (m, 8H), 11.45 (br, 1H), 12.1, 12.25 (s and s, total 1H).

Example 25

N-(Cyclohexylmethyl)-4-(5-benzoylbenzimidazol-2-yl)-3,5-dimethylpyrrole-2-carboxamide (25)

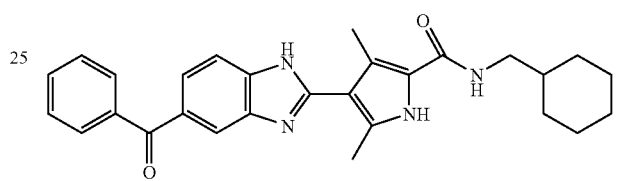

Following the procedure of Example 11 using cyclohexylmethylamine instead of N,N,N'-trimethylethylenediamine, N-(cyclohexylmethyl)-4-(5-benzoylbenzimidazol-2-yl)-3,5-dimethylpyrrole-2-carboxamide (73%) was obtained as a white solid.

Melting point: 254-255° C.

¹H-NMR (DMSO-d₆): δ (ppm) 0.91-0.97 (m, 2H), 1.17-1.22 (m, 3H), 1.51 (br, 1H), 1.63-1.75 (m, 5H), 2.46 (s, 3H), 2.49 (s, 3H), 3.10 (t, J=6.1 Hz, 2H), 7.38-7.41 (m, 1H), 7.55-7.90 (m, 9H), 11.36 (s, 1H).

Example 26

N-(5-Methylisoxazole-3-yl)-4-(5-benzoylbenzimidazol-2-yl)-3,5-dimethylpyrrole-2-carboxamide (26)

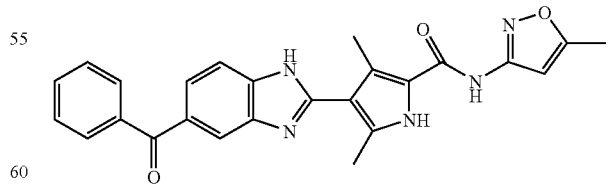

Following the procedure of Example 11 using 3-amino-5-methylisoxazole instead of N,N,N'-trimethylethylenediamine, N-(5-methylisoxazole-3-yl)-4-(5-benzoylbenzimidazol-2-yl)-3,5-dimethylpyrrole-2-carboxamide (45%) was obtained as a light yellow solid.

Melting point: 271-273° C.

$^{1}$H-NMR (DMSO-$d_6$): δ (ppm) 2.41 (s, 3H), 2.57 (s, 3H), 2.59 (s, 3H), 6.73 (s, 1H), 7.59-7.99 (m, 8H), 8.11 (s, 1H), 10.77 (s, 1H), 12.56 (s, 1H).

Example 27

N-(4-Cyanophenyl)-4-(5-benzoylbenzimidazol-2-yl)-3,5-dimethylpyrrole-2-carboxamide (27)

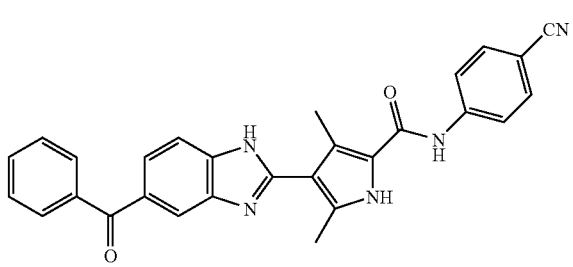

Following the procedure of Example 11 using 4-cyanoaniline instead of N,N,N'-trimethylethylenediamine, N-(4-cyanophenyl)-4-(5-benzoylbenzimidazol-2-yl)-3,5-dimethylpyrrole-2-carboxamide (38%) was obtained as a light yellow solid.

Melting point: 252-254° C.

$^{1}$H-NMR (DMSO-$d_6$): δ (ppm) 2.51 (s, 3H), 2.58 (s, 3H), 7.58-8.07 (m, 12H), 10.6 (br, 1H).

Example 28

N-(Indole-5-yl)-4-(5-benzoylbenzimidazol-2-yl)-3,5-dimethylpyrrole-2-carboxamide (28)

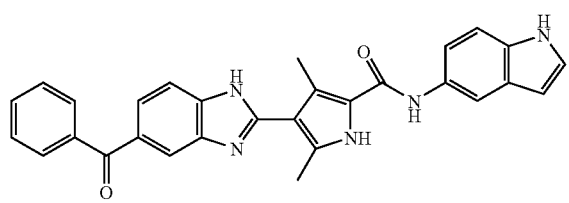

Following the procedure of Example 11 using 5-aminoindole instead of N,N,N'-trimethylethylenediamine, N-(indole-5-yl)-4-(5-benzoylbenzimidazol-2-yl)-3,5-dimethylpyrrole-2-carboxamide (63%) was obtained as a light yellow solid.

Melting point: 167-169° C.

$^{1}$H-NMR (DMSO-$d_6$): δ (ppm) 2.53, 2.55 (s and s, 3H), 2.58, 2.59 (s and s, 3H), 6.40 (t, J=2.2 Hz, 1H), 7.29-7.38 (m, 3H), 7.56-7.95 (m, 9H), 9.30 (d, J=4.9 Hz, 1H), 11.00 (brs, 1H), 11.56, 11.60 (s and s, total 1H), 12.14, 12.29 (s and s, total 1H).

Example 29

N-(3,4-Methylenedioxyphenyl-1-yl)-4-(5-benzoylbenzimidazol-2-yl)-3,5-dimethylpyrrole-2-carboxamide (29)

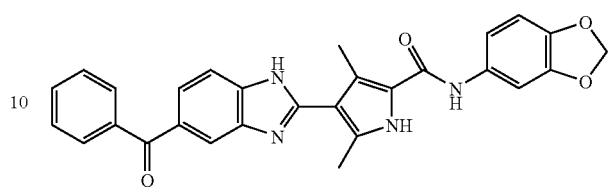

Following the procedure of Example 11 using 3,4-methylenedioxyaniline instead of N,N,N'-trimethylethylenediamine, N-(3,4-methylenedioxyphenyl-5-yl)-4-(5-benzoylbenzimidazol-2-yl)-3,5-dimethylpyrrole-2-carboxamide (55%) was obtained as a light yellow solid.

Melting point: 160-162° C.

$^{1}$H-NMR (DMSO-$d_6$): δ (ppm) 2.52 (s, 3H), 2.55 (s, 3H), 6.00 (s, 2H), 6.87 (d, J=8.3 Hz, 1H), 7.07 (dd, J=2.1, 8.3 Hz, 1H), 7.39 (d, J=2.1 Hz, 1H), 7.55-7.77 (m, 8H), 7.91 (brs, 1H), 9.41 (s, 1H).

Example 30

N-(2,3-Dihydrobenzofuran-5-yl)-4-(5-benzoylbenzimidazol-2-yl)-3,5-dimethylpyrrole-2-carboxamide (30)

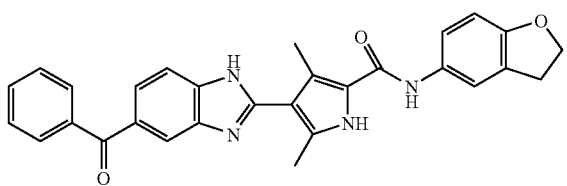

Following the procedure of Example 11 using 2,3-dihydro-5-aminobenzofuran instead of N,N,N'-trimethylethylenediamine, N-(2,3-dihydrobenzofuran-5-yl)-4-(5-benzoylbenzimidazol-2-yl)-3,5-dimethylpyrrole-2-carboxamide (63%) was obtained as a light yellow solid.

Melting point: 170-172° C.

$^{1}$H-NMR (DMSO-$d_6$): δ (ppm) 2.50 (s, 3H), 2.55 (s, 3H), 3.19 (t, J=8.4 Hz, 2H), 4.52 (t, J=8.4 Hz, 2H), 6.73 (d, J=8.6 Hz, 1H), 7.30 (s, 1H), 7.31 (d, J=8.4 Hz, 1H), 7.55-7.91 (m, 9H), 11.56 (br, 1H), 12.14, 12.28 (s and s, total 1H).

Example 31

N-(Benzothiazole-6-yl)-4-(5-benzoylbenzimidazol-2-yl)-3,5-dimethylpyrrole-2-carboxamide (31)

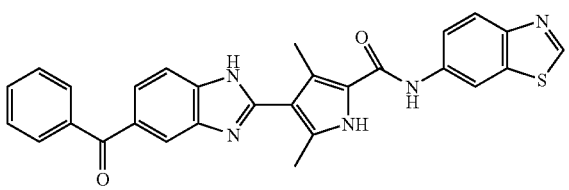

Following the procedure of Example 11 using 6-aminobenzothiazole instead of N,N,N'-trimethylethylenediamine, N-(benzothiazole-6-yl)-4-(5-benzoylbenzimidazol-2-yl)-3,5-dimethylpyrrole-2-carboxamide (75%) was obtained as a light yellow solid.

Melting point: 155-157° C.

$^1$H-NMR (DMSO-d$_6$): δ (ppm) 2.55 (s, 3H), 2.56 (s, 3H), 7.55-8.08 (m, 11H), 8.62 (s, 1H), 9.27 (s, 1H), 9.79 (s, 1H), 11.71 (s, 1H).

Example 32

N-(3,4-Ethylenedioxyphenyl)-4-(5-benzoylbenzimidazol-2-yl)-3,5-dimethylpyrrole-2-carboxamide (32)

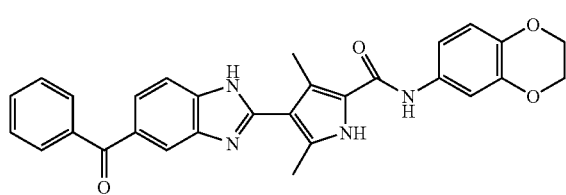

Following the procedure of Example 11 using 3,4-ethylenedioxyaniline instead of N,N,N'-trimethylethylenediamine, N-(3,4-ethylenedioxyphenyl)-4-(5-benzoylbenzimidazol-2-yl)-3,5-dimethylpyrrole-2-carboxamide (63%) was obtained as a light yellow solid.

Melting point: 145-147° C.

$^1$H-NMR (DMSO-d$_6$): δ (ppm) 2.53 (s, 3H), 2.55 (s, 3H), 4.13-4.30 (m, 4H), 6.81 (d, J=9.0 Hz, 1H), 7.09 (dd, J=9.0, 2.0 Hz, 1H), 7.32 (d, J=2.0 Hz, 1H), 7.55-7.98 (m, 8H), 9.32, 9.34 (s and s, total 1H), 11.55, 11.59 (s and s, total 1H), 12.14, 12.29 (s and s, total 1H).

Example 33

N-(2-Pyridylmethyl)-4-(5-benzoylbenzimidazol-2-yl)-3,5-dimethylpyrrole-2-carboxamide (33)

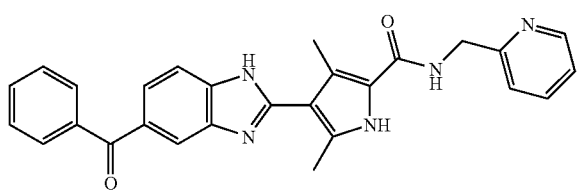

Following the procedure of Example 11 using 2-aminomethylpyridine instead of N,N,N'-trimethylethylenediamine, N-(2-pyridylmethyl)-4-(5-benzoylbenzimidazol-2-yl)-3,5-dimethylpyrrole-2-carboxamide (87%) was obtained as a light yellow amorphous.

$^1$H-NMR (DMSO-d$_6$): δ (ppm) 2.48, 2.50 (s and s, total 3H), 2.55, 2.57 (s and s, total 3H), 4.59 (br, 2H), 7.28-8.05 (m, 12H), 8.53 (s, 1H), 11.51 (br, 1H), 12.14, 12.28 (s and s, total 1H).

Example 34

N-(2-(2-Pyridyl)ethyl)-4-(5-benzoylbenzimidazol-2-yl)-3,5-dimethylpyrrole-2-carboxamide (34)

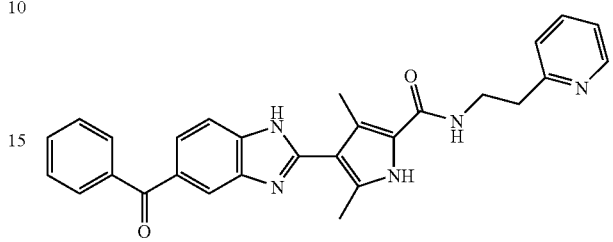

Following the procedure of Example 11 using 2-(2-aminoethyl)pyridine instead of N,N,N'-trimethylethylenediamine, N-(2-(2-pyridyl)ethyl)-4-(5-benzoylbenzimidazol-2-yl)-3,5-dimethylpyrrole-2-carboxamide (54%) was obtained as a white solid.

Melting point: 237.5-243.9° C.

$^1$H-NMR (DMSO-d$_6$): δ (ppm) 2.44 (s, 3H), 2.46 (s, 3H), 2.99-3.03 (m, 2H), 3.62-3.64 (m, 2H), 7.23-7.92 (m, 12H), 8.53 (br, 1H), 11.4 (s, 1H), 12.1 (s, 1H).

Example 35

N-(3,4-Dichlorobenzyl)-4-(5-benzoylbenzimidazol-2-yl)-3,5-dimethylpyrrole-2-carboxamide (35)

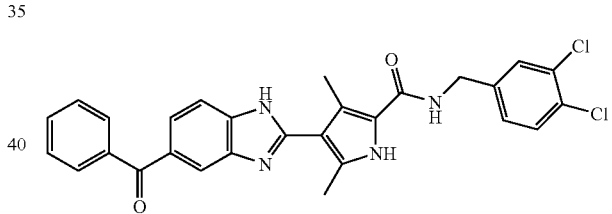

Following the procedure of Example 11 using 3,4-dichlorobenzylamine instead of N,N,N'-trimethylethylenediamine, N-(3,4-dichlorobenzyl)-4-(5-benzoylbenzimidazol-2-yl)-3,5-dimethylpyrrole-2-carboxamide (63%) was obtained as a purple solid.

Melting point: 141-143° C.

$^1$H-NMR (DMSO-d$_6$): δ (ppm) 2.48 (s, 3H), 2.53 (s, 3H), 4.46 (d, J=5.4 Hz, 2H), 7.27-8.15 (m, 12H), 11.51 (s, 1H).

Example 36

N-(3,4-Dimethoxybenzyl)-4-(5-benzoylbenzimidazol-2-yl)-3,5-dimethylpyrrole-2-carboxamide (36)

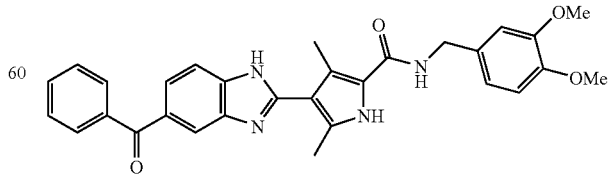

Following the procedure of Example 11 using 3,4-dimethoxybenzylamine instead of N,N,N'-trimethylethylenediamine, N-(3,4-dimethoxybenzyl)-4-(5-benzoylbenzimidazol-2-yl)-3,5-dimethylpyrrole-2-carboxamide (68%) was obtained as a purple solid.

Melting point: 120-122° C.

$^1$H-NMR (DMSO-d$_6$): δ (ppm) 2.47 (s, 3H), 2.54 (s, 3H), 3.73 (s, 3H), 3.75 (s, 3H), 4.41 (d, J=5.4 Hz, 2H), 6.85-6.98 (m, 3H), 7.55-7.95 (m, 8H), 11.44 (brs, 1H).

Example 37

N-(3,4-Methylenedioxyphenylmethyl)-4-(5-benzoyl-benzimidazol-2-yl)-3,5-dimethylpyrrole-2-carboxamide (37)

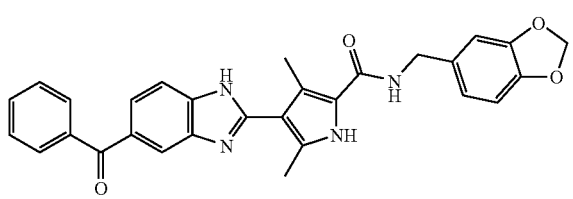

Following the procedure of Example 11 using piperonylamine instead of N,N,N'-trimethylethylenediamine, N-(3,4-methylenedioxyphenylmethyl)-4-(5-benzoylbenzimidazol-2-yl)-3,5-dimethylpyrrole-2-carboxamide (56%) was obtained as a light yellow solid.

Melting point: 165-167° C.

$^1$H-NMR (DMSO-d$_6$): δ (ppm) 2.47 (s, 3H), 2.50 (s, 3H), 4.38 (d, J=5.6 Hz, 2H), 5.99 (s, 2H), 6.81-6.93 (m, 3H), 7.55-7.77 (m, 7H), 7.90 (brs, 1H).

Example 38

N-(2,3,4,5-Tetrahydro-3-oxo-pyridazine-6-yl-methyl)-4-(5-benzoylbenzimidazol-2-yl)-3,5-dimethylpyrrole-2-carboxamide (38)

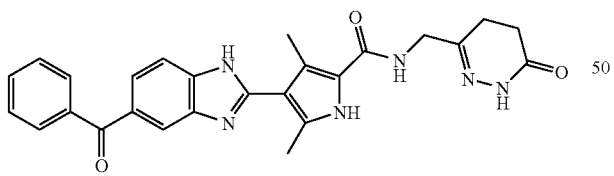

Following the procedure of Example 11 using 6-aminomethyl-4,5-dihydropyridazin-3(2H)-one instead of N,N,N'-trimethylethylenediamine, N-(2,3,4,5-tetrahydro-3-oxo-pyridazine-6-yl-methyl)-4-(5-benzoylbenzimidazol-2-yl)-3,5-dimethylpyrrole-2-carboxamide (14%) was obtained as a light red solid.

Melting point: 287° C.

$^1$H-NMR (DMSO-d$_6$): δ (ppm) 2.29-2.33 (m, 2H), 2.46-2.50 (m, 2H), 2.50 (s, 6H), 4.10 (s, 2H), 7.56-7.93 (m, 8H), 10.60 (s, 1H), 11.48 (br, 1H), 12.13, 12.28 (s and s, total 1H).

Example 39

((4-(5-Benzoylbenzimidazol-2-yl)-3,5-dimethylpyrrol-2-yl)-carbonyl)pyrrolidine (39)

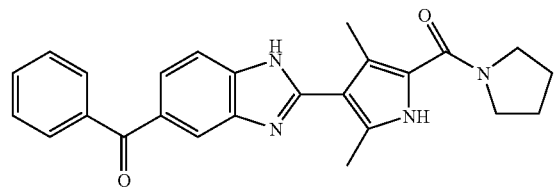

Following the procedure of Example 11 using pyrrolidine instead of N,N,N'-trimethylethylenediamine, ((4-(5-benzoylbenzimidazol-2-yl)-3,5-dimethylpyrrol-2-yl)-carbonyl)pyrrolidine (73%) was obtained as a light yellow solid.

Melting point: 155-157° C.

$^1$H-NMR (DMSO-d$_6$): δ (ppm) 1.85 (br, 4H), 2.48 (s, 3H), 2.50 (s, 3H), 3.48 (br, 4H), 7.55-7.77 (m, 8H), 7.89 (s, 1H), 11.3 (s, 1H).

Example 40

((4-(5-benzoylbenzimidazol-2-yl)-3,5-dimethylpyrrol-2-yl)-carbonyl)morpholine (40)

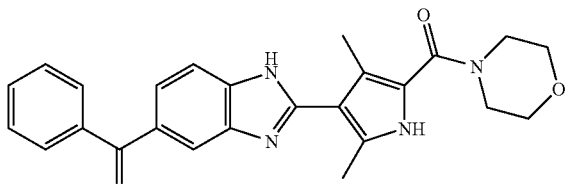

Following the procedure of Example 11 using morpholine instead of N,N,N'-trimethylethylenediamine, ((4-(5-benzoyl-benzimidazol-2-yl)-3,5-dimethylpyrrol-2-yl)-carbonyl)morpholine (65%) was obtained as a light yellow solid.

Melting point: 201-203° C.

$^1$H-NMR (DMSO-d$_6$): δ (ppm) 2.30 (s, 3H), 2.48 (s, 3H), 3.54 (brs, 4H), 3.61 (brs, 4H), 7.55-7.76 (m, 8H), 7.91 (s, 1H), 11.51 (brs, 1H).

Example 41

((4-(5-Benzoylbenzimidazol-2-yl)-3,5-dimethylpyrrol-2-yl)-carbonyl)-4-phenylpiperazine (41)

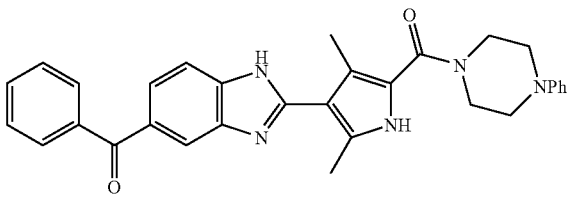

Following the procedure of Example 11 using 1-phenylpiperazine instead of N,N,N'-trimethylethylenediamine, ((4-(5-benzoylbenzimidazol-2-yl)-3,5-dimethylpyrrol-2-yl)-carbonyl)-4-phenylpiperazine (70%) was obtained as an ocher solid.

Melting point: 145-147° C.

$^1$H-NMR (DMSO-$d_6$): δ (ppm) 2.33 (s, 3H), 2.23-2.57 (m, 2H), 2.50 (s, 3H), 3.01-3.54 (m, 4H), 3.70 (br, 2H), 6.82 (t, J=7.3 Hz, 1H), 6.98 (d, J=8.1 Hz, 2H), 7.15-7.28 (m, 2H), 7.55-8.08 (m, 8H), 11.43 (brs, 1H).

Example 42

((4-(5-Benzoylbenzimidazol-2-yl)-3,5-dimethylpyrrol-2-yl)-carbonyl)pyrazoline (42)

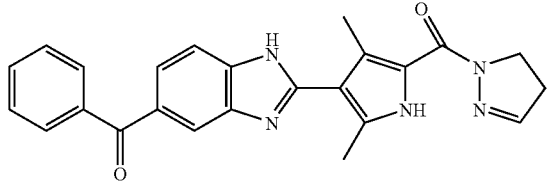

Following the procedure of Example 11 using pyrazoline instead of N,N,N'-trimethylethylenediamine, ((4-(5-benzoylbenzimidazol-2-yl)-3,5-dimethylpyrrol-2-yl)-carbonyl)pyrazoline (73%) was obtained as a light yellow solid.

Melting point: 148-150° C.

$^1$H-NMR (DMSO-$d_6$): δ (ppm) 2.47 (s, 3H), 2.49 (s, 3H), 2.85-3.00 (m, 2H), 3.79-3.93 (m, 2H), 7.29 (s, 1H), 7.54-7.80 (m, 7H), 7.91 (s, 1H), 11.20 (s, 1H), 12.23 (br, 1H).

Example 43

((4-(5-Benzoylbenzimidazol-2-yl)-3,5-dimethylpyrrol-2-yl)-carbonyl)-4-hydroxypiperidine (43)

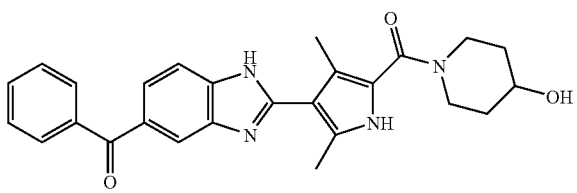

Following the procedure of Example 11 using 4-hydroxypiperidine instead of N,N,N'-trimethylethylenediamine, ((4-(5-benzoylbenzimidazol-2-yl)-3,5-dimethylpyrrol-2-yl)-carbonyl)-4-hydroxypiperidine (55%) was obtained as a light yellow solid.

Melting point: 288-290° C.

$^1$H-NMR (DMSO-$d_6$): δ (ppm) 1.27-1.48 (m, 2H), 1.69-1.87 (m, 2H), 2.28 (s, 3H), 2.47 (s, 3H), 3.14-3.35 (m, 2H), 3.65-3.97 (m, 3H), 4.78 (s, 1H), 7.52-7.96 (m, 8H), 11.43 (s, 1H), 11.85-12.33 (br, 1H).

Example 44

((4-(5-Benzoylbenzimidazol-2-yl)-3,5-dimethylpyrrol-2-yl)-carbonyl)-4-ethoxycarbonylpiperidine (44)

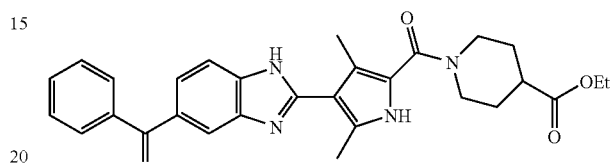

Following the procedure of Example 11 using isonipecotic acid ethyl ester instead of N,N,N'-trimethylethylenediamine, ((4-(5-benzoylbenzimidazol-2-yl)-3,5-dimethylpyrrol-2-yl)-carbonyl)-4-ethoxycarbonylpiperidine (72%) was obtained as a brown solid.

Melting point: 272-274° C.

$^1$H-NMR (CDCl$_3$): δ (ppm) 1.27 (t, J=7.1 Hz, 3H), 1.74 (br, 2H), 1.97 (br, 2H), 2.35 (brs, 3H), 2.54 (br, 3H), 2.58-2.59 (m, 1H), 3.06-3.11 (br, 2H), 4.15 (q, J=7.1 Hz, 2H), 4.22 (br, 2H), 7.47-8.15 (m, 8H), 10.52 (br, 1H), 11.53, 11.60 (s and s, total 1H).

Example 45

((4-(5-Benzoylbenzimidazol-2-yl)-3,5-dimethylpyrrol-2-yl)-carbonyl)piperidine-4-carboxylic acid (45)

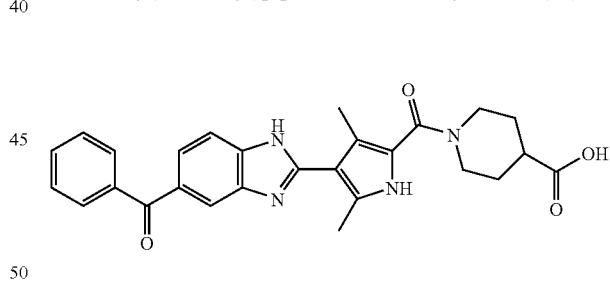

A 1 N sodium hydroxide aqueous solution (16.2 ml, 16.2 mmol) was added to an ethanol (15 ml) solution of the ((4-(5-benzoylbenzimidazol-2-yl)-3,5-dimethylpyrrol-2-yl)-carbonyl)-4-ethoxycarbonylpiperidine (4.19 g, 10.8 mmol) obtained in Example 44, and stirred at 100° C. for 4 hours. The reaction mixture was allowed to cool to room temperature with stirring, and then neutralized with 6 N hydrochloric acid (12 ml, 16.2 mmol). The precipitate was collected by filtration, and dried at reduced pressure to afford ((4-(5-benzoylbenzimidazol-2-yl)-3,5-dimethylpyrrol-2-yl)-carbonyl)piperidine-4-carboxylic acid (3.02 g, 78%) as white crystals.

Melting point: 267-271° C.

$^1$H-NMR (CDCl$_3$): δ (ppm) 1.74 (m, 2H), 1.98 (d, J=10 Hz, 2H), 2.35 (s, 3H), 2.53 (s, 3H), 2.58-2.59 (m, 1H), 3.14 (dd, J=10, 10 Hz, 2H), 4.20 (d, J=10 Hz, 2H), 7.49-8.11 (m, 8H), 10.39 (br, 1H), 11.50 (br, 1H).

Example 46

N-Dimethylaminoethyl-1-((4-(5-benzoylbenzimidazol-2-yl)-3,5-dimethylpyrrol-2-yl)-carbonyl)piperidine-4-carboxamide (46)

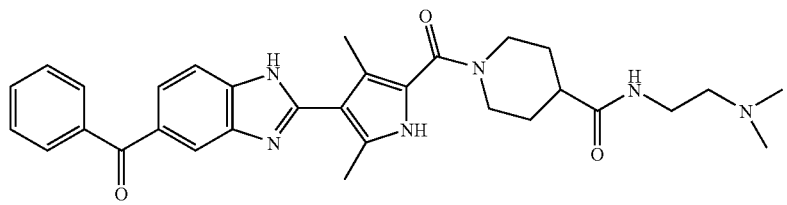

1-Ethyl-3-(3-dimethylaminopropyl)carbodiimide hydrochloride (31 mg, 0.16 mmol) and 1-hydroxybenzotriazole monohydrate (25 mg, 0.16 mmol) were added to a pyridine (4 ml) solution of the ((4-(5-benzoylbenzimidazol-2-yl)-3,5-dimethylpyrrol-2-yl)-carbonyl)piperidine-4-carboxylic acid (70 mg, 0.15 mmol) obtained in Example 45. N,N-Dimethylethylenediamine (13 mg, 0.15 mmol) was added to the reaction mixture and heated. The reaction mixture was stirred at 60° C. (internal temperature) for 10 hours, and then allowed to cool to room temperature with stirring. The solvent was evaporated, and the residue was purified using medium pressure silica gel flash column chromatography (NH silica gel, chloroform:methanol=98:2) to afford N-dimethylaminoethyl-1-((4-(5-benzoylbenzimidazol-2-yl)-3,5-dimethylpyrrol-2-yl)-carbonyl)piperidine-4-carboxamide (44 mg, 55%) as white crystals.

Melting point: 258-260° C.

$^1$H-NMR (DMSO-$d_6$): δ (ppm) 1.48-1.72 (m, 4H), 2.13 (s, 6H), 2.26 (brs, 3H), 2.42, 2.46 (brs and brs, total 3H), 2.94-3.18 (m, 3H), 3.32 (br 4H), 4.09 (br, 2H), 7.55-7.90 (m, 8H), 11.42, 11.46 (s and s, total 1H), 12.02, 12.17 (s and s, total 1H).

Example 47

N-Methyl-N-(2-dimethylaminoethyl)-1-((4-(5-benzoylbenzimidazol-2-yl)-3,5-dimethylpyrrol-2-yl)-carbonyl)piperidine-4-carboxamide (47)

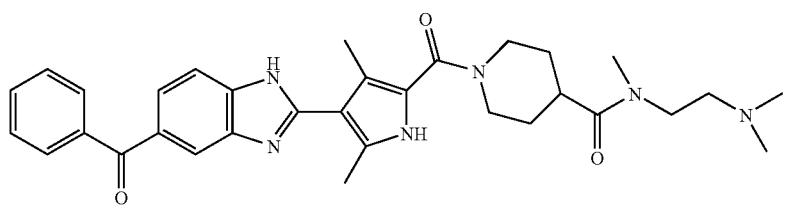

Following the procedure of Example 46 using N,N,N'-trimethylethylenediamine instead of N,N-dimethylethylenediamine, N-methyl-N-(2-dimethylaminoethyl)-1-((4-(5-benzoylbenzimidazol-2-yl)-3,5-dimethylpyrrol-2-yl)-carbonyl)piperidine-4-carboxamide (68%) was obtained as white crystals.

Melting point: 264-266° C.

$^1$H-NMR (CDCl$_3$): δ (ppm) 1.75 (br, 4H), 2.22 (s, 3H), 2.27 (s, 3H), 2.32, 2.34 (s and s, total 3H), 2.40 (t, J=4.6 Hz, 1H), 2.47 (t, J=4.6 Hz, 1H), 2.52, 2.54 (s and s, total 3H), 2.85 (br, 1H), 2.98-3.08 (m, 2H), 3.11 (s, 3H), 3.42-3.44 (m, 2H), 4.30 (m, 2H), 7.51-8.07 (m, 8H), 11.14 (s, 1H), 11.80 (s, 1H).

Example 48

N-(3-Dimethylaminopropyl)-1-((4-(5-benzoylbenzimidazol-2-yl)-3,5-dimethylpyrrol-2-yl)-carbonyl)piperidine-4-carboxamide (48)

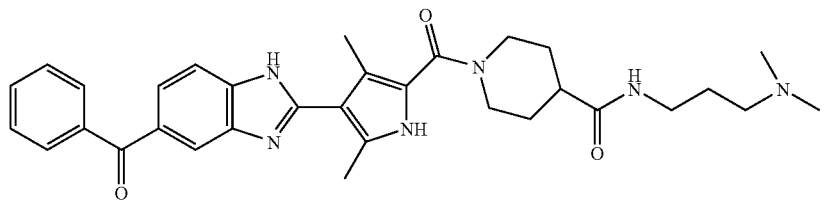

Following the procedure of Example 46 using N,N-dimethyl-1,3-propanediamine instead of N,N-dimethylethylenediamine, N-(3-dimethylaminopropyl)-1-((4-(5-benzoylbenzimidazol-2-yl)-3,5-dimethylpyrrol-2-yl)-carbonyl)piperidine-4-carboxamide (41%) was obtained as a white solid.

Melting point: 247-251° C.
$^1$H-NMR (DMSO-$d_6$): δ (ppm) 1.49-1.73 (m, 6H), 2.10 (s, 6H), 2.18 (t, J=7.3 Hz, 2H), 2.27, 2.28 (s and s, total 3H), 2.39, 2.50 (s and s, total 3H), 2.95-3.12 (m, 5H), 4.11 (br, 2H), 7.56-7.91 (m, 8H), 11.42, 11.46 (brs and brs, total 1H), 12.02, 12.17 (s and s, total 1H).

Example 49

N-(3-Methoxypropyl)-1-((4-(5-benzoylbenzimidazol-2-yl)-3,5-dimethylpyrrol-2-yl)-carbonyl)piperidine-4-carboxamide (49)

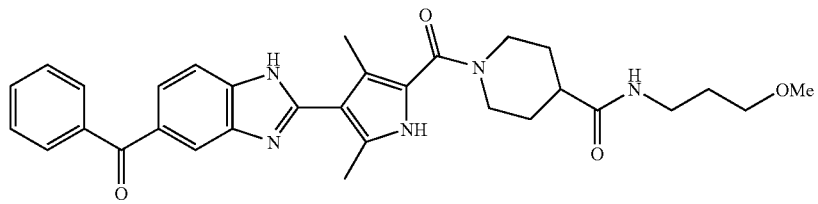

Following the procedure of Example 46 using 3-methoxypropylamine instead of N,N-dimethylethylenediamine, N-(3-methoxypropyl)-1-((4-(5-benzoylbenzimidazol-2-yl)-3,5-dimethylpyrrol-2-yl)-carbonyl)piperidine-4-carboxamide (98%) was obtained as a white solid.

Melting point: 289-291° C.
$^1$H-NMR (CDCl$_3$): δ (ppm) 1.72-1.87 (m, 6H), 2.34, 2.36 (s and s, total 3H), 2.37 (m, 1H), 2.53, 2.55 (s and s, total 3H), 3.03 (dd, J=12.7, 12.7 Hz, 2H), 3.25-3.38 (m, 2H), 3.34 (s, 3H), 3.46 (t, J=5.7 Hz, 2H), 4.32 (d, J=12.7 Hz, 2H), 6.82 (brs, 1H), 7.48-7.82 (m, 7H), 8.00, 8.16 (s and s, total 1H), 10.41, 10.46 (brs and brs, total 1H), 11.50, 11.56 (brs and brs, total 1H).

Example 50

N-Cyclohexylmethyl-1-((4-(5-benzoylbenzimidazol-2-yl)-3,5-dimethylpyrrol-2-yl)-carbonyl)piperidine-4-carboxamide (50)

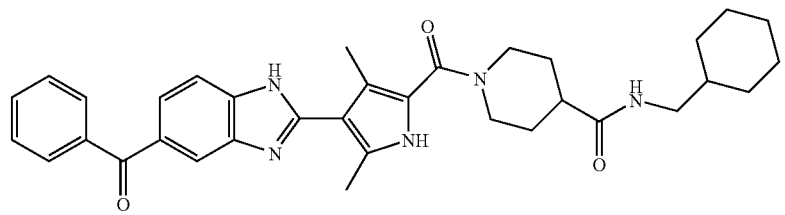

Following the procedure of Example 46 using cyclohexylmethylamine instead of N,N-dimethylethylenediamine, N-cyclohexylmethyl-1-((4-(5-benzoylbenzimidazol-2-yl)-3,5-dimethylpyrrol-2-yl)-carbonyl)piperidine-4-carboxamide (64%) was obtained as a white solid.

Melting point: 274-276° C.

$^1$H-NMR (CDCl$_3$): δ (ppm) 1.71-1.86 (m, 4H), 1.95 (br, 5H), 2.33, 2.34 (s and s, total 3H), 2.53, 2.54 (s and s, total 3H), 2.59 (br, 2H), 2.99 (br, 5H), 3.30 (br, 4H), 4.29 (d, J=12.0 Hz, 2H), 7.47-7.80 (m, 8H), 7.98, 8.12 (s and s, total 1H), 10.78, 10.82 (brs and brs, total 1H), 11.67, 11.75 (br and br, total 1H).

Example 51

5-Benzoyl-2-(pyrrol-2-yl)-benzimidazole (51)

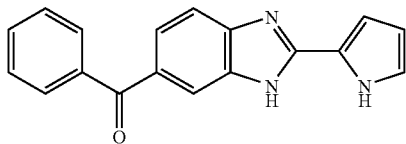

N,N-Dimethylacetamide (5 ml) was heated to 130° C., and 3,4-diaminobenzophenone (150 mg, 0.71 mol) and sodium hydrogensulfite (89 mg, 0.85 mol) were added and stirred for 5 minutes. 2-Formyl-pyrrole (81 mg, 0.85 mol) was added and stirred at 130° C. for 1.5 hours. The reaction mixture was allowed to cool to room temperature with stirring, and after addition of water to reaction mixture, precipitate was collected by filtration to afford 5-benzoyl-2-(pyrrol-2-yl)-benzimidazole (129 mg, 63%) as a pale yellow solid.

Melting point: 128-133° C.

$^1$H-NMR (DMSO-d$_6$): δ (ppm) 6.26 (s, 1H), 6.96 (s, 1H), 7.04 (s, 1H), 7.55-7.77 (m, 8H), 7.89 (s, 1H), 11.92 (s, 1H).

Example 52

5-Benzoyl-2-(3,5-dimethylpyrrol-2-yl)-benzimidazole (52)

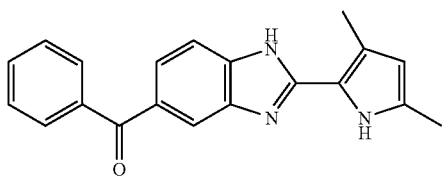

3,5-Dimethylpyrrole-2-carboxylic acid (99 mg, 0.71 mmol) was added to a pyridine (3 ml) solution of 3,4-diaminobenzophenone (150 mg, 0.71 mmol). 1-Ethyl-3-(3-dimethylaminopropyl)carbodiimide hydrochloride (149 mg, 0.78 mmol) and 1-hydroxybenzotriazole monohydrate (119 mg, 0.78 mmol) were further added, and the mixture was heated to 70° C. and stirred overnight. The reaction mixture was allowed to cool to room temperature with stirring, and then the solvent was evaporated. The residue was purified using medium pressure silica gel flash column chromatography (NH silica gel, chloroform:methanol=98:2). The residue was dissolved in acetic acid (3 ml), and stirred for 8 hours at 100° C. The reaction mixture was allowed to cool to room temperature with stirring, and then the solvent was evaporated. The residue was purified using medium pressure silica gel flash column chromatography (NH silica gel, chloroform:methanol=98:2), to afford 5-benzoyl-2-(3,5-dimethylpyrrol-2-yl)-benzimidazole (34 mg, 15% in two steps) as a yellow solid.

Melting point: 225-229° C.

$^1$H-NMR (DMSO-d$_6$): δ (ppm) 2.23 (s, 3H), 2.37 (s, 3H), 5.79 (s, 1H), 7.55-7.88 (m, 8H), 11.09, 11.21 (s and s, total 1H), 11.90, 12.06 (s and s, total 1H).

Example 53

5-(5-Benzoylbenzimidazol-2-yl)-2,4-dimethylpyrrole-3-carboxylic acid ethyl ester (53)

Example 53 (1)

5-Formyl-2,4-dimethyl-pyrrole-3-carboxylic acid ethyl ester (starting material for compound according to Example 53)

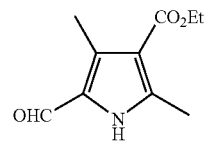

2,4-Diethoxycarbonyl-3,5-dimethylpyrrole (2.0 g) was dissolved in ethanol (20 ml), and a 1 N sodium hydroxide solution (20 ml) was added and stirred overnight at 80° C. After cooling to room temperature, the reaction mixture was neutralized with a hydrochloric acid solution. The precipitate was collected by filtration, and dried in vacuo. The obtained solid was dissolved in trifluoroacetic acid (20 ml), and stirred for 1 hour at 40° C. While cooling with ice, triethyl orthoformate (2.5 ml) was slowly added dropwise to the reaction mixture. The mixture was allowed to room temperature, and then stirred for 2 hours. The resultant was concentrated at reduced pressure. The residue was added to a saturated sodium hydrogencarbonate and stirred, and then the precipitate was collected by filtration. The obtained solid was purified using medium pressure silica gel flash column chromatography (hexane:ethyl acetate=5:1 to 1:1), and dried in vacuo to afford 5-formyl-2,4-dimethyl-pyrrole-3-carboxylic acid ethyl ester (1.21 g, 74%) as a light yellow solid.

Example 53 (2)

5-(5-Benzoylbenzimidazole-2-yl)-2,4-dimethylpyrrole-3-carboxylic acid ethyl ester (53)

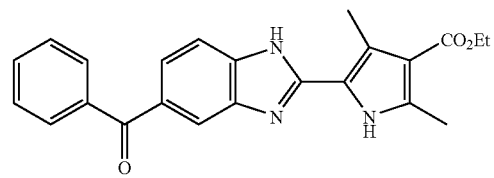

Sodium hydrogen sulfite (101 mg) and the 5-formyl-2,4-dimethyl-pyrrole-3-carboxylic acid ethyl ester (146 mg) obtained in Example 53 (1) were added to an N,N-dimethylacetamide (5 ml) solution of 3,4-diaminobenzophenone (160 mg). The mixture was heated to 120° C. and stirred for 10 hours. The reaction mixture was allowed to cool to room temperature, and then a 5% sodium carbonate (6 ml) was added and stirred at room temperature. The precipitate was collected by filtration to afford 5-(5-benzoylbenzimidazole-2-yl)-2,4-dimethylpyrrole-3-carboxylic acid ethyl ester (248 mg, 85%) as a light yellow solid.

Melting point: 185-187° C.

$^1$H-NMR (DMSO-$d_6$): δ (ppm) 1.32 (t, J=7.2 Hz, 3H), 2.50 (s, 3H), 2.52 (s, 3H), 4.29 (q, J=7.2 Hz, 2H), 7.55-7.77 (m, 7H), 7.95 (s, 1H), 11.8 (brs, 1H).

Example 54

5-(5-Benzoylbenzimidazole-2-yl)-2,4-dimethylpyrrole-3-carboxylic acid (54)

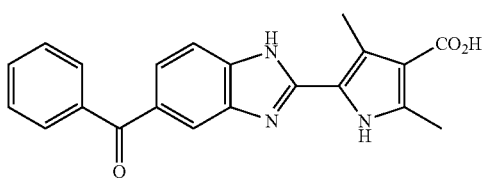

The 5-(5-benzoylbenzimidazole-2-yl)-2,4-dimethylpyrrole-3-carboxylic acid ethyl ester (200 mg) obtained in Example 53 (2) was dissolved in ethanol (5 ml) and tetrahydrofuran (5 ml). To this solution was added a 4 N sodium hydroxide aqueous solution (10 ml), and the mixture was heated under reflux for 12 hours. After the starting material was disappeared, the reaction mixture was allowed to cool to room temperature, and neutralized with a 1 N hydrochloric acid solution. The precipitate was collected by filtration to afford 5-(5-benzoylbenzimidazol-2-yl)-2,4-dimethylpyrrole-3-carboxylic acid (139 mg, 75%) as a light yellow solid.

Melting point: >300° C.

$^1$H-NMR (DMSO-$d_6$): δ (ppm) 2.50 (s, 3H), 2.63 (s, 3H), 7.55-7.77 (m, 8H), 7.90 (s, 1H), 12.20 (br, 1H).

Example 55

2-(5-Pyrrolidine-1-yl-methyl-furan-2-yl)-5-benzoyl-benzimidazole (55)

Example 55 (1)

5-Pyrrolidine-1-yl-methyl-furan-2-carboxylic acid ethyl ester (starting material for compound according to Example 55)

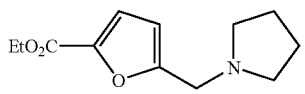

Pyrrolidine (0.75 g, 10.6 mmol) was added to an N,N-dimethylacetamide (15 ml) solution of 5-chloromethylfuran-2-carboxylic acid ethyl ester (1.0 g, 5.3 mmol), and stirred at room temperature for 24 hours. The solvent was evaporated, and the residue was purified using medium pressure silica gel flash column chromatography (NH silica gel, chloroform:methanol=98:2) to afford 5-pyrrolidine-1-yl-methyl-furan-2-carboxylic acid ethyl ester (793 mg, 67%).

$^1$H-NMR (DMSO-$d_6$): δ (ppm) 1.70 (br, 3H), 2.54 (br, 4H), 3.17 (br, 4H), 3.70 (s, 2H), 4.29 (br, 2H), 6.59 (s, 1H), 6.75 (br, 1H).

Example 55 (2)

5-Pyrrolidine-1-yl-methyl-furan-2-carboxylic acid (starting material for compound according to Example 55)

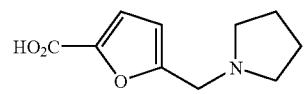

The 5-pyrrolidine-1-yl-methyl-furan-2-carboxylic acid ethyl ester (770 mg, 3.45 mmol) obtained in Example 55 (1) was dissolved in ethanol (4 ml). A 1 N sodium hydroxide aqueous solution (5.17 ml) was added dropwise to the solution, and the mixture was stirred overnight. The reaction mixture was neutralized with a 1 N hydrochloric acid solution (5.17 ml), and then ethanol was evaporated. The residue was dried to afford 5-pyrrolidine-1-yl-methyl-furan-2-carboxylic acid containing sodium chloride (1.08 g, sodium chloride content: 38% wt., quant.) as a white solid, which was used directly for the following reaction.

Example 55 (3)

2-(5-Pyrrolidine-1-yl-methyl-furan-2-yl)-5-benzoyl-benzimidazole (55)

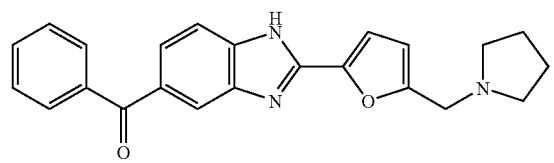

5-Pyrrolidine-1-yl-methyl-furan-2-carboxylic acid (62% purity, 223 mg, 0.71 mmol) was added to a pyridine (3 ml) solution of 3,4-diaminobenzophenone (150 mg, 0.71 mmol). 1-Ethyl-3-(3-dimethylaminopropyl)carbodiimide hydrochloride (149 mg, 0.78 mmol) and 1-hydroxybenzotriazole monohydrate (119 mg, 0.78 mmol) were further added, and the reaction mixture was heated to 70° C. and stirred overnight. The reaction mixture was allowed to cool to room temperature, and the solvent was evaporated. The residue was purified using medium pressure silica gel flash column chromatography (NH silica gel, chloroform:methanol=98:2), and the obtained residue was dissolved in acetic acid (3 ml) and stirred at 100° C. for 8 hours. The solution was allowed to cool to room temperature with stirring, and then the solvent was evaporated. The residue was purified using medium pressure silica gel flash column chromatography (NH silica gel, chloroform:methanol=98:2), to afford 2-(5-pyrrolidine-1-yl-methyl-furan-2-yl)-5-benzoylbenzimidazole (143 mg, 55% in two steps) as a yellow oil.

¹H-NMR (CDCl₃): δ (ppm) 1.90 (br, 4H), 2.81 (br, 4H), 3.88 (s, 2H), 6.45 (d, J=3.5 Hz, 1H), 7.19 (d, J=3.5 Hz, 1H), 7.44-7.84 (m, 8H), 8.10 (s, 1H).

Example 56

2-(5-Dimethylaminomethyl-furan-2-yl)-5-benzoyl-benzimidazole (56)

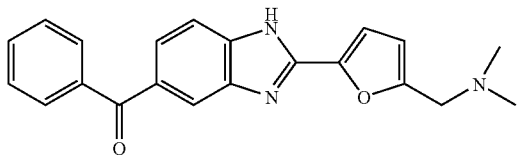

Following the procedure of Example 55 using dimethylamine instead of pyrrolidine, 2-(5-dimethylaminomethyl-furan-2-yl)-5-benzoylbenzimidazole (203 mg, 83%) was obtained as a light yellow amorphous.

¹H-NMR (DMSO-d₆): δ (ppm) 2.21 (s, 6H), 3.59 (s, 2H), 6.56 (d, J=3.2 Hz, 1H), 7.22 (d, J=3.2 Hz, 1H), 7.54-7.92 (m, 8H), 13.23 (br, 1H).

Example 57

5-(5-Benzoylbenzimidazol-2-yl)-furan-2-carboxylic acid (57)

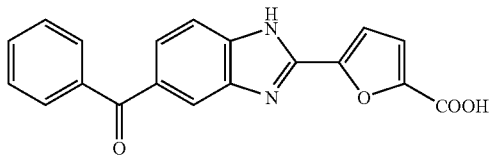

N,N-Dimethylacetamide (5 ml) was heated to 130° C., and 3,4-diaminobenzophenone (63 mg, 0.30 mmol) and sodium hydrogensulfite (37 mg, 0.36 mmol) were added and the mixture was stirred for 5 minutes. 5-Formyl-furan-2-carboxylic acid (50 mg, 0.36 mmol) was added and stirred at 130° C. for 1.5 hours. The reaction mixture was allowed to cool to room temperature with stirring, and after addition of water to reaction mixture, precipitate was collected by filtration to afford 5-(5-benzoylbenzimidazol-2-yl)-furan-2-carboxylic acid (63 mg, 64%) as a pale yellow solid.

Melting point: 170° C.

¹H-NMR (DMSO-d₆): δ (ppm) 7.39-8.01 (m, 10H), 13.61 (s, 1H).

Example 58

2-(5-Bromo-furan-2-yl)-5-benzoylbenzimidazole (58)

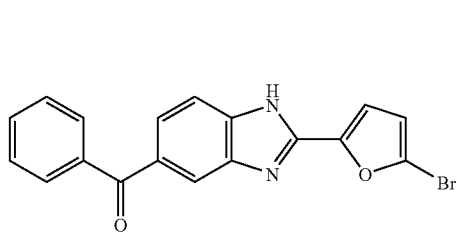

Following the procedure of Example 1 using 5-bromofuran-2-carboxylic acid instead of 2,4-dimethylfuran-3-carboxylic acid, 2-(5-bromo-furan-2-yl)-5-benzoylbenzimidazole (92%) was obtained as a yellow solid.

Melting point: 167-172° C.

¹H-NMR (CDCl₃): δ (ppm) 6.59 (d, J=3.4 Hz, 1H), 7.23 (d, J=3.4 Hz, 1H), 7.41-7.81 (m, 8H), 8.06 (s, 1H).

Example 59

(4-(5-Benzoylbenzimidazol-2-yl)-2-furanylcarbonyl) pyrrolidine (59)

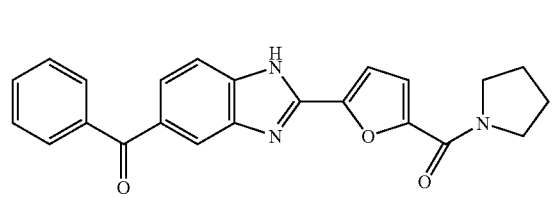

1-Ethyl-3-(3-dimethylaminopropyl)carbodiimide hydrochloride (63 mg, 0.33 mmol) and 1-hydroxybenzotriazole monohydrate (51 mg, 0.33 mmol) were added to a pyridine (4 ml) solution of the 5-(5-benzoylbenzimidazol-2-yl)-furan-2-carboxylic acid (100 mg, 0.30 mmol) obtained in Example 57. Pyrrolidine (21 mg, 0.30 mmol) was added and then heated. The reaction mixture was stirred at 70° C. for 6 hours, and then allowed to cool to room temperature with stirring. The solvent was evaporated, and the residue was purified using medium pressure silica gel flash column chromatography (NH silica gel, chloroform:methanol=98:2) to afford (4-(5-benzoylbenzimidazol-2-yl)-2-furanylcarbonyl)pyrrolidine (102 mg, 88%) as a brown oil.

¹H-NMR (CDCl₃): δ (ppm) 1.95-2.10 (m, 4H), 3.68 (t, j=6.8 Hz, 2H), 3.82 (t, J=6.8 Hz, 2H), 7.04 (d, J=3.7 Hz, 1H), 7.32 (d, J=3.7 Hz, 1H), 7.45-7.83 (m, 8H), 8.12 (s, 1H).

Example 60

5-(5-Benzoylbenzimidazol-2-yl)-furan-2-carboxamide (60)

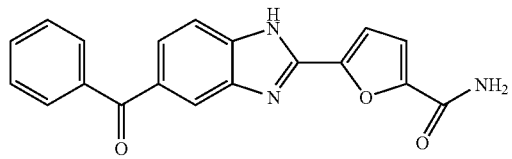

Following the procedure of Example 59 using a 28% aqueous ammonia instead of pyrrolidine, 5-(5-benzoylbenzimidazol-2-yl)-furan-2-carboxamide (96%) was obtained as a brown oil.

$^1$H-NMR (CDCl$_3$): δ (ppm) 6.58-8.19 (m, 12H), 12.76 (s, 1H).

Example 61

N-(2-Dimethylaminoethyl)-5-(5-benzoylbenzimidazol-2-yl)-furan-2-carboxamide (61)

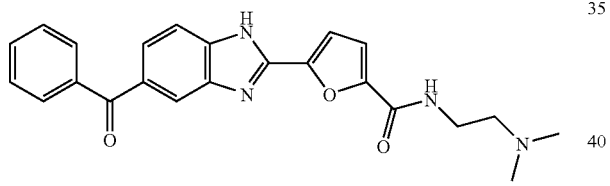

Following the procedure of Example 59 using N,N-dimethylethylenediamine instead of pyrrolidine, (N-(2-dimethylaminoethyl)-5-(5-benzoylbenzimidazol-2-yl)-furan-2-carboxamide (64%) was obtained as a brown oil.

$^1$H-NMR (CDCl$_3$): δ (ppm) 2.32 (s, 6H), 3.22 (br, 2H), 3.56 (br, 2H), 5.51 (br, 1H), 7.19-8.09 (m, 11H).

Example 62

N-(3,4-Methylenedioxyphenylmethyl)-5-(5-benzoylbenzimidazol-2-yl)-furan-2-carboxamide (62)

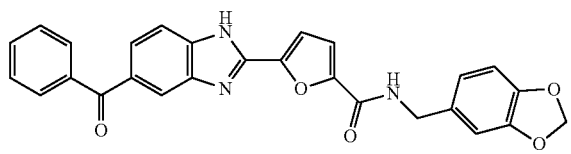

Following the procedure of Example 59 using piperonylamine instead of pyrrolidine, N-(3,4-methylenedioxyphenylmethyl)-5-(5-benzoylbenzimidazol-2-yl)-furan-2-carboxamide (77%) was obtained as a brown oil.

$^1$H-NMR (CDCl$_3$): δ (ppm) 4.42 (s, 2H), 5.85 (s, 2H), 6.63-7.96 (m, 15H).

Example 63

(4-(5-Benzoylbenzimidazol-2-yl)-2-furanylcarbonyl)thiazolidine (63)

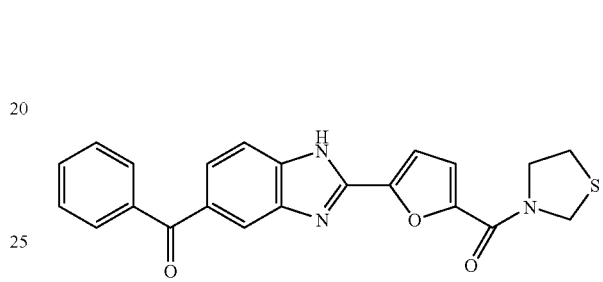

Following the procedure of Example 59 using thiazolidine instead of pyrrolidine, (4-(5-benzoylbenzimidazol-2-yl)-2-furanylcarbonyl)thiazolidine (64%) was obtained as a brown oil.

$^1$H-NMR (CDCl$_3$): δ (ppm) 2.25 (s, 2H), 3.12-3.26 (m, 4H), 7.28 (d, J=3.6 Hz, 1H), 7.34 (d, J=3.6 Hz, 1H), 7.48-7.82 (m, 8H), 8.08 (s, 1H).

Example 64

(N,N-Dimethyl)-4-(5-benzoylbenzimidazol-2-yl)-3,5-dimethylpyrrole-2-carboxamide (64)

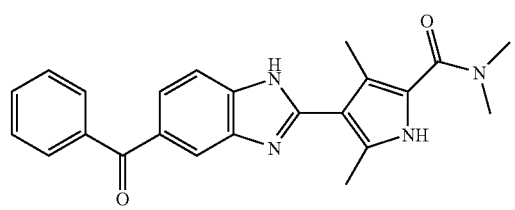

Following the procedure of Example 11 using a 40% dimethylamine aqueous solution instead of N,N,N'-trimethylethylenediamine, (N,N-dimethyl)-4-(5-benzoylbenzimidazol-2-yl)-3,5-dimethylpyrrole-2-carboxamide (95%) was obtained as a light yellow solid.

Melting point: 165-170° C.

¹H-NMR (DMSO-d₆): δ (ppm) 2.28, 2.30 (s and s, total 3H), 2.50, 2.51 (s and s, total 3H), 3.01 (s, 6H), 7.53-7.98 (m, 8H), 11.38, 11.42 (brs and brs, total 1H), 12.03, 12.17 (brs and brs, total 1H).

Example 65

(N-Hydroxy-N-methyl)-4-(5-benzoylbenzimidazol-2-yl)-3,5-dimethylpyrrole-2-carboxamide (65)

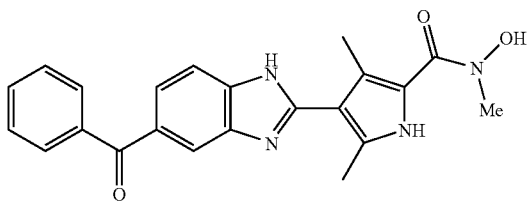

Following the procedure of Example 11 using N-methylhydroxylamine hydrochloride instead of N,N,N'-trimethylethylenediamine, (N-hydroxy-N-methyl)-4-(5-benzoylbenzimidazol-2-yl)-3,5-dimethylpyrrole-2-carboxamide (41%) was obtained as a light yellow solid.

Melting point: 227-229° C. (decomposition)

¹H-NMR (DMSO-d₆): δ (ppm) 2.38-2.57 (m, 6H), 3.30 (s, 3H), 7.54-8.00 (m, 8H), 9.92 (s, 1H), 11.19, 11.23 (brs and brs, total 1H), 12.11, 12.25 (s and s, total 1H).

Example 66

(N-Methyl)-4-(5-benzoylbenzimidazol-2-yl)-3,5-dimethylpyrrole-2-carboxamide (66)

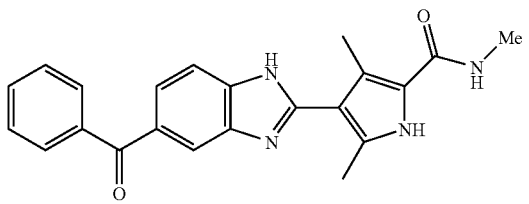

Following the procedure of Example 11 using a 40% methylamine aqueous solution instead of N,N,N'-trimethylethylenediamine, (N-methyl)-4-(5-benzoylbenzimidazol-2-yl)-3,5-dimethylpyrrole-2-carboxamide (81%) was obtained as a light yellow solid.

Melting point: 188-190° C.

¹H-NMR (DMSO-d₆): δ (ppm) 2.41-2.53 (m, 6H), 2.78, 2.79 (s and s, total 3H), 7.33-7.47 (br, 1H), 7.52-7.99 (m, 8H), 11.36, 11.40 (brs and brs, total 1H), 12.11, 12.26 (s and s, total 1H).

Example 67

(N-Hydroxymethyl)-4-(5-benzoylbenzimidazol-2-yl)-3,5-dimethylpyrrole-2-carboxamide (67)

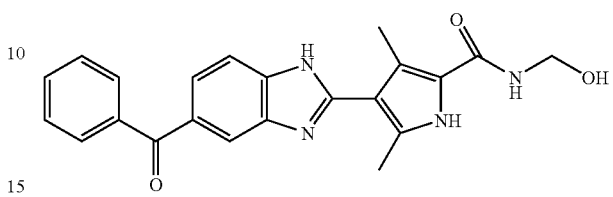

A 37% formaldehyde solution (0.17 ml) and a 1 N sodium hydroxide aqueous solution (0.02 ml) were added to a dimethyl sulfoxide (3 ml) solution of the 4-(5-benzoylbenzimidazol-2-yl)-3,5-dimethylpyrrole-2-carboxamide (358 mg, 1.0 mmol) obtained in Example 12, and the reaction mixture was stirred at room temperature for two days. After water was added to the reaction mixture, and the precipitate was collected by filtration. The solid was washed with water and dried at reduced pressure. The crude solid were purified using medium pressure silica gel flash column chromatography (methanol:chloroform=1:15 to 1:10) to afford (N-hydroxymethyl)-4-(5-benzoylbenzimidazol-2-yl)-3,5-dimethylpyrrole-2-carboxamide (76%) as a light yellow solid.

Melting point: 196-210° C.

¹H-NMR (DMSO-d₆): δ (ppm) 2.48 (s, 3H), 2.53 (s, 3H), 4.72 (dd, J=6.6, 6.6 Hz, 2H), 5.59 (t, J=6.6 Hz, 1H), 7.53-7.78 (m, 7H), 7.91 (s, 1H), 8.03 (t, J=6.3 Hz, 1H), 11.44 (brs, 1H), 12.10-12.18 (br, 1H).

Example 68

4-(5-Phenoxybenzimidazole-2-yl)-3,5-dimethylpyrrole-2-carboxylic acid ethyl ester (68)

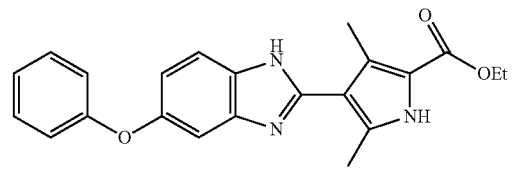

Sodium hydrogensulfite (0.87 g, 8.4 mmol) and 3,5-dimethyl-4-formylpyrrole-2-carboxylic acid ethyl ester (1.64 g, 8.4 mmol) were added to an N,N-dimethyl acetamide (25 ml) solution of 4-phenoxy-1,2-phenylenediamine (1.60 g, 8.0 mmol) reported in the references, and the reaction mixture was heated to 110° C. and stirred for 18 hours. The reaction mixture was allowed to cool to room temperature, and a 5% sodium carbonate was added. The mixture was extracted with ethyl acetate, and the extract was washed with water and a saturated sodium chloride, and then dried with anhydrous sodium sulfate. The desiccant was filtered off, and then the residue obtained by evaporation at reduced pressure was purified using medium pressure silica gel flash column chromatography (methanol:chloroform=1:100 to 1:30) to afford 4-(5-phenoxybenzimidazole-2-yl)-3,5-dimethylpyrrole-2-carboxylic acid ethyl ester (2.27 g, 76%) as a light yellow solid.

Melting point: 239-242° C.

$^1$H-NMR (CDCl$_3$): δ (ppm) 1.39 (t, J=7.1 Hz, 3H), 2.57 (s, 6H), 4.35 (q, J=7.1 Hz, 2H), 6.96-7.82 (m, 8H), 8.94 (brs, 1H), 9.17 (br, 1H).

Example 69

4-(5-Phenoxybenzimidazole-2-yl)-3,5-dimethylpyrrole-2-carboxylic acid (69)

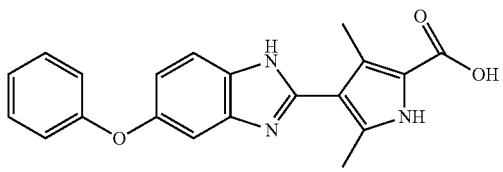

The 4-(5-phenoxybenzimidazole-2-yl)-3,5-dimethylpyrrole-2-carboxylic acid ethyl ester (1.88 g, 5.0 mmol) obtained in Example 68 was dissolved in ethanol (10 ml) and tetrahydrofuran (5 ml). To this solution was added a 4 N sodium hydroxide aqueous solution (6 ml, 24 mmol), and the mixture was stirred at 80° C. for 6 hours. The reaction mixture was cooled to 0° C., and neutralized with a 1 N hydrochloric acid solution. The precipitate was collected by filtration, and washed with water and dried at reduced pressure to afford 4-(5-phenoxybenzimidazole-2-yl)-3,5-dimethylpyrrole-2-carboxylic acid (1.70 g, 98%) as a light yellow solid.

Melting point: 167-172° C. (decomposition)

$^1$H-NMR (DMSO-d$_6$): δ (ppm) 2.42 (s, 3H), 2.47 (s, 3H), 6.85-7.16 (m, 5H), 7.30-7.38 (m, 2H), 7.54 (d, J=8.6 Hz, 1H), 11.44 (brs, 1H), 11.50-12.38 (br, 3H).

Example 70

((4-(5-Phenoxybenzimidazole-2-yl)-3,5-dimethylpyrrol-2-yl)-2-carbonyl)pyrrolidine (70)

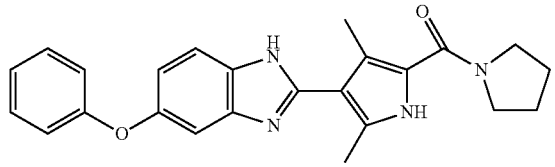

1-Hydroxybenzotriazole monohydrate (84 mg, 0.55 mmol), 1-ethyl-3-(3-dimethylaminopropyl)carbodiimide (115 mg, 0.6 mmol), and pyrrolidine (0.06 ml, 0.75 mmol) were added to an N,N-dimethylformamide (3 ml) solution of the 4-(5-phenoxybenzimidazole-2-yl)-3,5-dimethylpyrrole-2-carboxylic acid (174 mg, 0.5 mmol) obtained in Example 67, and stirred at 60° C. for 19 hours. The reaction mixture was allowed to cool to room temperature, and water and a saturated sodium hydrogencarbonate were added. The precipitate was collected by filtration. The obtained crude solid were purified using medium pressure silica gel flash column chromatography (methanol:chloroform=1:20 to 1:10) to afford ((4-(5-phenoxybenzimidazole-2-yl)-3,5-dimethylpyrrol-2-yl)-2-carbonyl)pyrrolidine (116 mg, 58%) as a light yellow solid.

Melting point: 251-254° C.

$^1$H-NMR (CDCl$_3$): δ (ppm) 1.90 (br, 4H), 2.25 (s, 3H), 2.28 (s, 3H), 3.55 (br, 4H), 6.91-7.72 (m, 8H), 9.44 (s, 1H), 10.30 (brs, 1H).

Example 71

((4-(5-Phenoxybenzimidazole-2-yl)-3,5-dimethylpyrrol-2-yl)-2-carbonyl)morpholine (71)

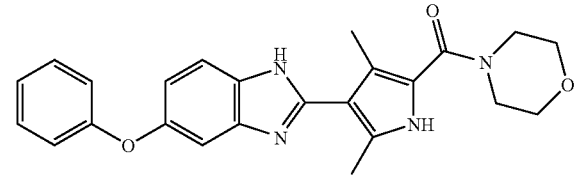

Following the procedure of Example 70 using morpholine instead of pyrrolidine, ((4-(5-phenoxybenzimidazole-2-yl)-3,5-dimethylpyrrol-2-yl)-2-carbonyl)morpholine (67%) was obtained as a light yellow solid.

Melting point: 268-270° C.

$^1$H-NMR (CDCl$_3$): δ (ppm) 2.24 (s, 3H), 2.28 (s, 3H), 3.38-3.82 (m, 8H), 6.91-7.12 (m, 4H), 7.21-7.73 (m, 4H), 9.43 (s, 1H), 10.00 (brs, 1H).

Example 72

N-(2-(2-Pyridyl)ethyl)-4-(5-phenoxybenzimidazole-2-yl)-3,5-dimethylpyrrole-2-carboxamide (72)

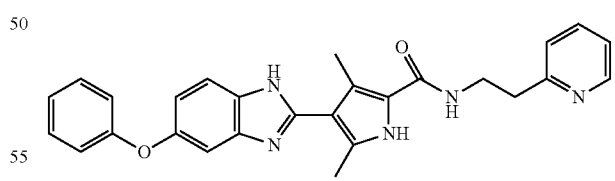

Following the procedure of Example 70 using 2-(2-aminoethyl)pyridine instead of pyrrolidine, N-(2-(2-pyridyl)ethyl)-4-(5-phenoxybenzimidazole-2-yl)-3,5-dimethylpyrrole-2-carboxamide (76%) was obtained as a light yellow solid.

Melting point: 290-293° C.

$^1$H-NMR (DMSO-d$_6$): δ (ppm) 2.42 (s, 3H), 2.43 (s, 3H), 3.01 (t, J=7.1 Hz, 2H), 3.64 (dt, J=12.5, 7.1 Hz, 2H), 6.83-7.84 (m, 12H), 8.43-8.65 (m, 1H), 11.31 (s, 1H), 11.81, 11.92 (s and s, total 1H).

Example 73

N-(Methoxy)-4-(5-phenoxybenzimidazole-2-yl)-3,5-dimethylpyrrole-2-carboxamide (73)

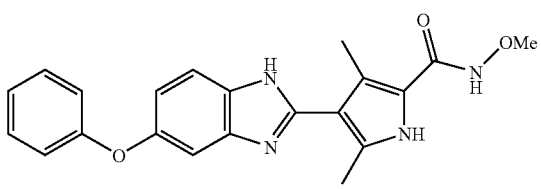

Following the procedure of Example 70 using O-methylhydroxylamine hydrochloride instead of pyrrolidine, N-(methoxy)-4-(5-phenoxybenzimidazole-2-yl)-3,5-dimethylpyrrole-2-carboxamide (71%) was obtained as a light yellow solid.

Melting point: 166-168° C.
$^1$H-NMR (CDCl$_3$): δ (ppm) 2.43 (s, 6H), 3.71 (s, 3H), 6.83-7.64 (m, 8H), 10.71 (s, 1H), 11.38 (s, 1H), 11.83, 11.94 (s and s, total 1H).

Example 74

(N-Methoxy-N-methyl)-4-(5-phenoxybenzimidazole-2-yl)-3,5-dimethylpyrrole-2-carboxamide (74)

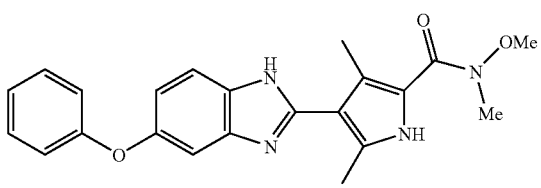

Following the procedure of Example 15 (3) using 4-phenoxy-1,2-phenylenediamine instead of 3,4-diaminobenzophenone, (N-methoxy-N-methyl)-4-(5-phenoxybenzimidazole-2-yl)-3,5-dimethylpyrrole-2-carboxamide (74%) was obtained as a light yellow solid.

Melting point: 130-134° C.
$^1$H-NMR (CDCl$_3$): δ (ppm) 2.57 (s, 6H), 3.35 (s, 3H), 3.72 (s, 3H), 6.92-7.85 (m, 8H), 9.14-9.43 (br, 2H).

Example 75

2-(2-Cyano-3,5-dimethylpyrrol-4-yl)-5-phenoxybenzimidazole (75)

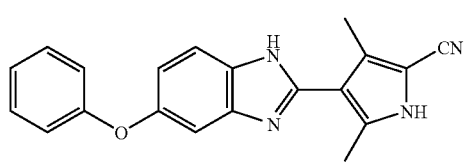

Following the procedure of Example 13 (2) using 4-phenoxy-1,2-phenylenediamine instead of 3,4-diaminobenzophenone, (2-(2-cyano-3,5-dimethylpyrrol-4-yl)-5-phenoxybenzimidazole (77%) was obtained as a light yellow solid.

Melting point: 278-280° C.
$^1$H-NMR (CDCl$_3$): δ (ppm) 2.42 (s, 3H), 2.48 (s, 3H), 6.90-7.77 (m, 8H), 10.61 (brs, 1H), 11.31 (s, 1H).

Example 76

4-(5-Phenoxybenzimidazole-2-yl)-3,5-dimethylfuran-2-carboxamide (76)

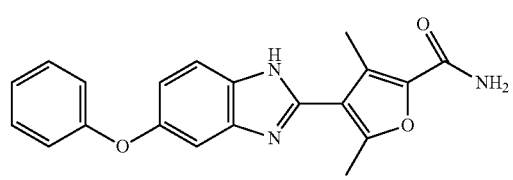

Following the procedure of Example 2 (3) using 4-phenoxy-1,2-phenylenediamine instead of 3,4-diaminobenzophenone, 4-(5-phenoxybenzimidazole-2-yl)-3,5-dimethylfuran-2-carboxamide (59%) was obtained as a light yellow solid.

Melting point: 248-251° C.
$^1$H-NMR (DMSO-d$_6$): δ (ppm) 2.49 (s, 3H), 2.57 (s, 3H), 6.89-7.86 (m, 10H), 12.27 (brs, 1H).

Comparative Example 1

4-(5-(4-Pyridylsulfenyl)-6-phenoxybenzimidazole-2-yl)-3,5-dimethylpyrrole-2-carboxylic acid ethyl ester

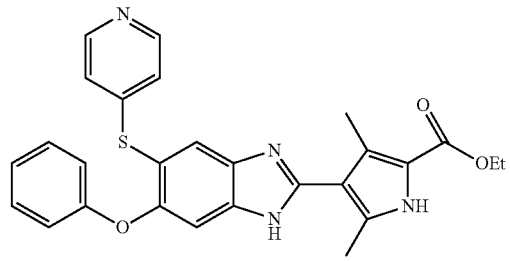

A mixture was prepared by adding 2.0 g (35.8 mmol) of an iron powder to 2.75 g (8.10 mmol) of 4-phenoxy-2-nitro-5-(4-pyridylsulfenyl)aniline reported in Japanese Unexamined Patent Application Publication No. 2000-026430. Ten milliliters (10.0 mmol) of a 1 N ammonium chloride aqueous solution was added to this mixture and stirred at 85° C. for 3 hours. The reaction mixture was cooled to room temperature again, 60 ml of ethyl acetate was added, and the insoluble material was filtered with Celite®. The resultant filtrate was separated, and then the ethyl acetate layer was washed with water and dried with anhydrous magnesium sulfate. After the filtration, the filtrate was concentrated, and then dried at reduced pressure to afford a crude diamine (2.0 g).

One gram (3.23 mmol) of the obtained crude diamine was dissolved in 15 ml of N,N-dimethylacetamide, and 0.37 g (3.55 mmol) of sodium hydrogensulfite and 0.69 g (3.53 mmol) of 3,5-dimethyl-4-formylpyrrole-2-carboxylic acid ethyl ester were added to the solution. The reaction mixture was heated to 130° C. and stirred for 16 hours. The reaction mixture was allowed to cool to room temperature, and then the solvent was evaporated at reduced pressure. A 5% sodium hydrogencarbonate was added to the residue, and the precipitate was collected by filtration, washed with water, and dried at reduced pressure. The obtained crude solid was purified using medium pressure silica gel flash column chromatography (methanol:chloroform=1:50 to 1:10) to afford 4-(5-(4-pyridylsulfenyl)-6-phenoxybenzimidazole-2-yl)-3,5-dimethylpyrrole-2-carboxylic acid ethyl ester (0.75 g, 48%) as an amorphous.

$^1$H-NMR (DMSO-d$_6$) δ (ppm): 1.35 (t, J=7.2 Hz, 3H), 2.46 (s, 3H), 2.55 (s, 3H), 4.29 (q, J=7.2 Hz), 7.10-7.80 (m, 9H), 8.23-8.36 (m, 2H), 11.61 (br, 1H), 12.20 (br, 1H)

Comparative Example 2

(N,N-Dimethyl)-4-(5-(4-pyridylsulfenyl)-6-phenoxybenzimidazole-2-yl)-3,5-dimethylpyrrole-2-carboxamide

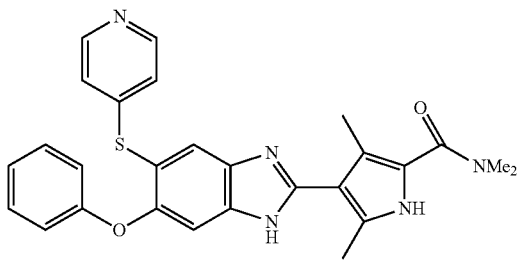

Five milliliters of ethanol and 3.5 ml (3.5 mmol) of a 1 N sodium hydroxide aqueous solution were added to 0.48 g (1.0 mmol) of the 4-(5-(4-pyridylsulfenyl)-6-phenoxybenzimidazole-2-yl)-3,5-dimethylpyrrole-2-carboxylic acid ethyl ester obtained in Comparative Example 1, and the reaction mixture was stirred at 60° C. for 17 hours. The reaction mixture was allowed to cool and concentrated, and the insoluble material was filtered off by adding water. The filtrate was neutralized with a 2 N hydrochloric acid solution, and the precipitate was collected by filtration, washed with water, and dried at reduced pressure to afford crude carboxylic acid (0.22 g). 0.2 g (0.4 mmol) of the crude carboxylic acid was dissolved in 3 ml of N,N-dimethylformamide, and then 92 mg (0.5 mmol) of 1-ethyl-3-(3-dimethylaminopropyl)carbodiimide and 0.25 ml (2.2 mmol) of a 40% dimethylamine aqueous solution were added to the solution. The reaction mixture was stirred at 60° C. for 18 hours. The reaction mixture was allowed to cool to room temperature, and the solvent was evaporated at reduced pressure. The obtained residue was purified using medium pressure silica gel flash column chromatography (methanol:chloroform=1:100 to 1:10) to afford (N,N-dimethyl)-4-(5-(4-pyridylsulfenyl)-6-phenoxybenzimidazole-2-yl)-3,5-dimethylpyrrole-2-carboxamide (83 mg, 43%) as an amorphous.

$^1$H-NMR (DMSO-d$_6$) δ (ppm): 2.44-2.55 (m, 6H), 3.02 (s, 6H), 7.08-7.81 (m, 9H), 8.33-8.47 (m, 2H), 11.56 (br, 1H), 12.18 (br, 1H).

Comparative Example 3

Comparative Example 3 (1)

2-Furaldehyde-5-diethylphosphonate

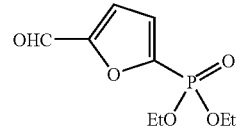

A tetrahydrofuran (30 ml) solution of 2-furaldehyde diethyl acetal (13.6 g, 80 mmol) was cooled to −78° C., and then a 1.6 M n-butyllithium in hexane solution (50 ml, 80 mmol) was added dropwise and stirred at −78° C. for 1 hour. Chlorodiethyl phosphonate (12.7 ml, 88 mmol) was added to the reaction mixture and stirred at the same temperature for 30 minutes. A saturated ammonium chloride was added to the reaction mixture. The precipitate was filtered off, and water was added to the residue obtained by distilling the filtrate solvent at reduced pressure. The mixture was extracted with ethyl acetate, washed with water and a saturated sodium chloride, and then dried with anhydrous sodium sulfate. After the desiccant was filtered off, 80% acetic acid (100 ml) was added to the residue obtained by evaporation at reduced pressure, and stirred at 90° C. for 4 hours. The reaction mixture was cooled to room temperature, and water was added to the residue obtained by distilling the solvent at reduced pressure. The mixture was extracted with ethyl acetate, and the extract was washed with water, a saturated sodium hydrogencarbonate, water, and a saturated sodium chloride, and then dried with anhydrous sodium sulfate. The desiccant was filtered off, and then the residue obtained by evaporation at reduced pressure was purified using medium pressure silica gel flash column chromatography (ethyl acetate:hexane=1:1 to 5:1) to afford 2-furaldehyde-5-diethylphosphonate (1.65 g, 9%) as a light yellow oil.

$^1$H-NMR (CDCl$_3$): δ (ppm) 1.30-1.50 (m, 6H), 4.02-4.35 (m, 4H), 7.18-7.32 (m, 2H), 9.80 (s, 1H).

Comparative Example 3 (2)

5-Benzophenone-2-(2-diethylphosphono-5-furanyl)benzimidazole

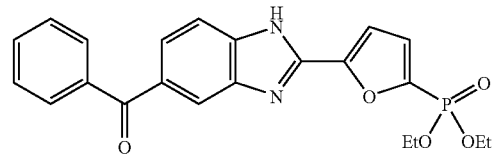

Sodium hydrogensulfite (0.46 g, 4.4 mmol) was added to an N,N-dimethyl formamide (10 ml) solution of 3,4-diaminobenzophenone (0.85 g, 4.0 mmol), and heated to 100° C. An N,N-dimethyl formamide (5 ml) solution of the 2-furaldehyde-5-diethylphosphonate (1.16 g, 5.0 mmol) obtained in Comparative Example 3 (1) was added dropwise to the mixture, and stirred at 100° C. for 3 hours. The reaction mixture was allowed to cool to room temperature, and a 5% sodium carbonate was added. The mixture was extracted with ethyl acetate, and the extract was washed with water and a saturated sodium chloride, and then dried with anhydrous sodium sulfate. The desiccant was filtered off, and then the residue obtained by distilling the solvent at reduced pressure was purified using medium pressure silica gel flash column chromatography (ethyl acetate:chloroform=1:5 to 1:1) to afford 5-benzophenone-2-(2-diethylphosphono-5-furanyl)benzimidazole (1.05 g, 62%) as a light yellow oil.

$^{1}$H-NMR (CDCl$_{3}$): δ (ppm) 1.38 (t, J=7.1 Hz, 6H), 4.13-4.35 (m, 4H), 7.20-8.28 (m, 10H), 10.65-11.38 (br, 1H).

Comparative Example 3 (3)

5-Benzophenone-2-(2-phosphono-5-furanyl)benzimidazole dihydrate

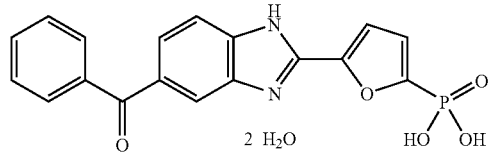

47% Hydrobromic acid (6.0 ml) and water (4.0 ml) were added to the 5-benzophenone-2-(2-diethylphosphono-5-furanyl)benzimidazole (424 mg, 1.0 mmol) obtained in Comparative Example 3 (2), and stirred at 100° C. for 8 hours. The reaction mixture was allowed to cool to room temperature, and the solvent was evaporated at reduced pressure. Water was added to the residue, and the precipitate was collected by filtration, washed with water, and dried at reduced pressure to afford a 5-benzophenone-2-(2-phosphono-5-furanyl)benzimidazole dihydrate (359 mg, 89%) as a light yellow solid.

Melting point: 224-229° C.

Anal. Calcd. for $C_{18}H_{13}N_{2}O_{5}P+2H_{2}O$: C, 53.47%; H, 4.24%; N, 6.93%.

Found: C, 53.74%; H, 4.19%; N, 6.92%.

$^{1}$H-NMR (DMSO-d$_{6}$): δ (ppm) 7.08-7.17 (m, 1H), 7.31-7.39 (m, 1H), 7.53-7.87 (m, 9H), 7.97 (s, 1H).

Experiment 1

Hematopoietic Synthase Inhibitory Activity

Experiment 1 was carried out according to the method of Urade, Y. et al. (J. Biol. Chem. 262, 3820-3825, (1987)). More specifically, the reaction mixture (49 μL); 100 mM Tris-HCl (pH 8.0), 1 mM reduced glutathione, 0.1 mg/mL γ-globulin, and human hematopoietic synthase (quantum sufficient), and a test compound (final concentration: 0.01-100 μM) were preincubated at 25° C. for 5 minutes. In place of the test compound, a DMSO solution (final concentration: 1%) was used in the solvent control group (Control Group). Subsequently, 1 μL of [$^{14}$C] prostaglandin H2 (final concentration: 10 μM) was added to start the reaction. One minute after the start of the reaction, 250 μL of a reaction stopper solution (diethylether/methanol/1M citric acid (30/4/1) cooled to −20° C. was added to stop the reaction.

Thereafter, 50 μL of the upper layer portion (organic solvent phase) was applied to a TLC plate and developed at −20° C. for 45 minutes (developer: diethylether/methanol/acetic acid (capacity ratio=90/2/1)). After drying the plate, the plate was exposed to an imaging plate for 1 to 24 hours, and the radioactivity corresponding to prostaglandin D2 was analyzed using an image analyzer (product of FUJIFILM Corporation). The area (%) occupied by the prostaglandin D2 band per lane was calculated, and the concentration of the test compound required to inhibit 50% of the hematopoietic synthase (IC50 value) was calculated by comparison with the Control group in each experiment. Table 1-3 show the results.

TABLE 1

| Compound No. | Concentration of Pharmaceutical Compound Required to Inhibit 50% of Hematopoietic Synthase (μM) |
|---|---|
| 1 | 0.796 |
| 2 | 0.274 |
| 3 | 0.178 |
| 4 | 0.278 |
| 5 | 1.45 |
| 6 | 1.74 |
| 7 | 0.588 |
| 9 | 0.110 |
| 10 | 0.436 |
| 11 | 0.269 |
| 12 | 0.100 |
| 13 | 0.540 |
| 14 | 0.355 |
| 15 | 0.256 |
| 16 | 2.28 |
| 17 | 0.124 |
| 18 | 0.080 |
| 19 | 0.874 |
| 20 | 0.871 |
| 21 | 0.304 |
| 22 | 0.829 |
| 23 | 0.223 |
| 24 | 0.496 |
| 25 | 0.286 |
| 26 | 0.149 |
| 27 | 0.309 |
| 28 | 0.073 |
| 29 | 0.053 |
| 30 | 0.113 |

TABLE 2

| Compound No. | Concentration of Pharmaceutical Compound Required to Inhibit 50% of Hematopoietic Synthase (μM) |
|---|---|
| 31 | 0.090 |
| 32 | 0.124 |
| 34 | 0.072 |
| 35 | 0.746 |
| 36 | 0.195 |
| 37 | 0.213 |
| 38 | 0.136 |
| 39 | 0.351 |
| 40 | 0.592 |
| 41 | 1.45 |
| 42 | 0.063 |
| 43 | 0.791 |
| 44 | 1.67 |
| 45 | 0.643 |
| 46 | 0.758 |
| 47 | 0.269 |
| 48 | 0.124 |
| 49 | 0.649 |
| 50 | 0.843 |
| 52 | 4.80 |
| 53 | 3.08 |
| 56 | 4.78 |
| 57 | 4.13 |
| 58 | 2.37 |

TABLE 2-continued

| Compound No. | Concentration of Pharmaceutical Compound Required to Inhibit 50% of Hematopoietic Synthase (μM) |
|---|---|
| 59 | 3.56 |
| 60 | 4.36 |
| 62 | 2.43 |
| 63 | 1.25 |

TABLE 3

| Compound Number | Concentration of Pharmaceutical Compound Required to Inhibit 50% of Hematopoietic Synthase (μM) |
|---|---|
| 64 | 0.377 |
| 65 | 0.124 |
| 66 | 0.077 |
| 67 | 0.109 |
| 68 | 0.210 |
| 69 | 0.491 |
| 70 | 0.614 |
| 71 | 0.870 |
| 72 | 0.209 |
| 73 | 0.240 |
| 74 | 0.263 |
| 75 | 0.218 |
| 76 | 0.109 |
| HQL-79 | 24.4 |
| Comparative Example 1 | >30 μM |
| Comparative Example 2 | >30 μM |
| Comparative Example 3 | 29.3 |

The above results clearly show that the compounds of the invention have a higher hematopoietic synthase inhibitory activity than HQL-79, which is known as a hematopoietic synthase inhibitor.

Experiment 2

Inhibitory Activity for Prostaglandin D2 Production Into Bronchoalveolar Lavage Fluid in Rats A physiological saline solution containing 1 mg of ovalbumin and 4 mg of alum was subcutaneously injected into the backs of 7-week-old male Brawn Norway rats in an amount of 1 mL/body, and 0.06 mg of killed pertussis bacteria were intraperitoneally injected into each rat to perform active sensitization. Fourteen days after sensitization, the rats inhaled 2% ovalbumin for 10 minutes. One hour after inhalation, bronchoalveolar lavage fluid was collected. The amount of PGD2 in the bronchoalveolar lavage fluid was determined using an EIA kit. Two hours before antigen inhalation, a test compound (10 mg/kg) was orally administered. Table 4 shows the results.

TABLE 4

| Compound No. | Inhibition (%) of the PGD2 Amount in Bronchoalveolar Lavage Fluid |
|---|---|
| 3 | 36 |
| 13 | 48 |
| 15 | >72 |
| 40 | 65 |
| 42 | 88 |

The results clearly show that the oral administration of 10 mg/kg of the compounds of the invention can strongly inhibit the PGD2 amount in the bronchoalveolar lavage fluid.

Experiment 3

Ameliorating Activity for Antigen-Induced Nasal Congestion in Guinea Pig

A physiological saline solution containing 1 mg/mL of ovalbumin was subcutaneously injected into the backs of 5-week-old male Std:Hartley guinea pigs in an amount of 1 mL/body for active sensitization (primary sensitization). One week and two weeks after primary sensitization, 20 μL each of a physiological saline solution containing 10 mg/mL of ovalbumin was instilled into the nasal cavities using a micropipette (sensitization by nasal administration). Three weeks after primary sensitization, 10 μL each of a physiological saline solution containing 20 mg/mL of ovalbumin was instilled into the nasal cavities using a micropipette to induce a rhinitis reaction.

Before, and 10 minutes and 2, 3, 4, 5, 6 and 7 hours after nasal instillation of ovalbumin, the nasal airway resistance per 100 breaths was determined using a comprehensive respiratory function analysis system ("Pulmos-I", a product of M.I.P.S. Co., Ltd.), and the average at each measurement time was calculated and expressed as nRaw. The increase % of nRaw was calculated according to the following formula.

Increase(%) of nRaw at each measurement time=
(nRaw at each measurement time−nRaw before induction)÷nRaw before induction×100

Nasal congestion was evaluated by measuring the area under the curve of nRaw increase % during the period of 3 to 7 hours after induction ($AUC_{3-7\ hr}$). "$I_{3-7\ hr}$" refers to the increase of nRaw during the period of 3 to 7 hours after induction.

$$AUC_{3-7hr} = \frac{1}{2}(I_{3hr} + 2 \times I_{4hr} + 2 \times I_{5hr} + 2 \times I_{6hr} + I_{7hr})$$

To confirm the effects on nasal congestion by inhibition of PGD2 production, Compound 15 was selected as a representative compound and orally administered once a day for 15 consecutive days from the day of nasal sensitization performed 1 week after primary sensitization to the day of induction performed 3 weeks after primary sensitization. On the nasal sensitization days (1 week and 2 weeks after primary sensitization) and the induction day, compound 15 was orally administered 1 hour before intranasal instillation of ovalbumin.

A leukotriene antagonist, Pranlukast, and a thromboxane antagonist, Ramatoroban, both of which are highly effective against nasal congestion, were used as positive control substances. Table 5 shows the results.

TABLE 5

| Compound | Dose (mg/kg) | $AUC_{3-7\ hr}$ (% · hr) | Inhibition (%) |
|---|---|---|---|
| Normal group | — | 27.0 ± 15.9 | — |
| Control Group | — | 564.8 ± 103.4** | 0 |
| Compound 15 | 3 | 273.9 ± 69.1## | 60.8 |
|  | 10 | 153.5 ± 27.1## | 76.5 |
|  | 30 | 65.7 ± 28.9## | 92.8 |
| Pranlukast | 30 | 126.3 ± 41.7$$ | 81.5 |
| Ramatroban | 30 | 183.4 ± 29.3$$ | 70.9 |

The repeated oral administration of 3, 10 or 30 mg/kg of compound 15 inhibited antigen-induced nasal congestion (increase of nasal airway resistance: $AUC_{3-7h}$) dose-dependently, and the percentages of inhibition by the respective amounts were 60.8%, 76.5%, and 92.8%. The nasal congestion-ameliorating action by 10 mg/kg of compound 15 was equivalent to the effect achieved by the administration of 30 mg/kg of Pranlukast or Ramatroban. When administered in the same dose, i.e., 30 mg/kg, compound 15 exhibited a more potent ameliorating effect than the positive control substances.

Examples of formulations comprising the compound of the invention as an active ingredient are given below.

Formulation Example 1 Tablets

| Compound of Example 15 | 50 mg |
|---|---|
| Corn starch | 50 mg |
| Microcrystalline cellulose | 50 mg |
| Hydroxypropylcellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets (250 mg per tablet) were prepared using the above ingredients in the indicated amounts according to a routine method.

Formulation Example 2 Granules

| Compound of Example 19 | 300 mg |
|---|---|
| Lactose | 540 mg |
| Corn starch | 100 mg |
| Hydroxypropylcellulose | 50 mg |
| Talc | 10 mg |

Granules (1000 mg per packet) were prepared using the above ingredients in the indicated amounts according to a routine method.

Formulation Example 3 Capsules

| Compound of Example 20 | 100 mg |
|---|---|
| Lactose | 30 mg |
| Corn starch | 50 mg |
| Microcrystalline cellulose | 10 mg |
| Magnesium stearate | 3 mg |

Capsules (193 mg per capsule) were prepared using the above ingredients in the indicated amounts according to a routine method.

Formulation Example 4 Injection Fluid

| Compound of Example 21 | 100 mg |
|---|---|
| Sodium chloride | 3.5 mg |
| Distilled water for injection | q.s. |
| (2 ml per ampoule) | |

An injection fluid was prepared using the above ingredients in the indicated amounts according to a routine method.

Formulation Example 5 Syrup

| Compound of Example 27 | 200 mg |
|---|---|
| Purified sucrose | 60 g |
| Ethyl parahydroxybenzoate | 5 mg |
| Butyl parahydroxybenzoate | 5 mg |
| Flavor | q.s. |
| Coloring agent | q.s. |
| Purified water | q.s. |

A syrup was prepared using the above ingredients in the indicated amounts according to a routine method.

Formulation Example 6 Suppositories

| Compound of Example 35 | 300 mg |
|---|---|
| "Witepsol W-35" | 1400 mg |

(trade name of Dynamite Nobel Co., Ltd., a mixture of mono-, di- and triglycerides of saturated fatty acids from lauric acid to stearic acid)

Suppositories were prepared using the above ingredients in the indicated amounts according to a routine method.

INDUSTRIAL APPLICABILITY

According to the present invention, benzimidazole compounds represented by Formula (I) or salts thereof, which are useful as prostaglandin D synthase inhibitors can be provided.

The benzimidazole compounds or salts thereof according to the present invention have excellent prostaglandin D synthase inhibitory activity.

Owing to their excellent prostaglandin D synthase inhibitory activity, the benzimidazole compounds or salts thereof according to the present invention are useful as prophylactic and/or preventive agents for diseases associated with prostaglandin D2 or metabolites thereof, such as allergic and inflammatory diseases, and as aggravation inhibitors for Alzheimer's disease and brain damage, and can also be expected to have other useful medicinal effects.

The invention claimed is:

1. A benzimidazole compound represented by Formula (I)

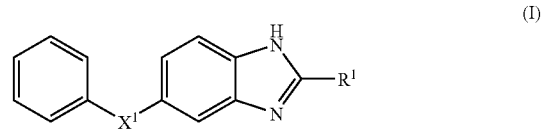

(I)

wherein $X^1$ is oxygen or carbonyl, and $R^1$ is a pyrrole ring having 1 to 3 substituents;
excluding compounds represented by Formula (I) wherein at least one of the substituents is a phosphoric acid group or a phosphoric ester group;
or a salt thereof.

2. The benzimidazole compound or salt thereof according to claim 1, wherein $X^1$ is carbonyl.

3. The benzimidazole compound or salt thereof according to claim 1, wherein:

$X^1$ is oxygen or carbonyl;

$R^1$ is a pyrrole ring having 1 to 3 substituents, and the substituents on the pyrrole ring are selected from the group consisting of halogen, cyano, nitro, $C_{1-6}$ alkyl one or more substituents, $C_{3-7}$ cycloalkyl that may have one or more substituents, $C_{2-6}$ alkenyl that may have one or more substituents, and —(C=O)—$R^2$;

$R^2$ is hydrogen, hydroxy, $C_{1-6}$ alkyl that may have one or more substituents, $C_{1-6}$ alkoxy that may have one or more substituents, or —$NR^3R^4$; and $R^3$ and $R^4$ are the same or different, and are each hydrogen, hydroxy, $C_{1-6}$ alkyl that may have one or more substituents, $C_{1-6}$ alkoxy that may have one or more substituents, amino, mono- or di($C_1$-$C_6$ alkyl)amino that may have one or more substituents, $C_6$-$C_{14}$ aryl that may have one or more substituents, or a saturated or unsaturated heterocyclic group that may have one or more substituents, or $R^3$ and $R^4$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom, and the cyclic amino group may have one or more substituents.

4. The benzimidazole compound or salt thereof according to claim 1, wherein:

$X^1$ is carbonyl;

$R^1$ is a pyrrole ring having 1 to 3 substituents, and the substituents on the pyrrole ring are each halogen, cyano, nitro, $C_{1-6}$ alkyl that may have 1 to 3 substituents selected from the group consisting of halogen, hydroxy, and —$NR^{3'}R^{4'}$, $C_{2-6}$ alkenyl that may have 1 to 3 substituents selected from the group consisting of cyano, carboxy, and ($C_1$-$C_6$ alkoxy)carbonyl, or —(C=O)—$R^2$;

$R^2$ is hydrogen, hydroxy, $C_{1-6}$ alkoxy, or —$NR^3R^4$;

$R^{3'}$ and $R^{4'}$ are the same or different, and are each hydrogen or $C_{1-6}$ alkyl, or $R^{3'}$ and $R^{4'}$, taken together with the adjacent nitrogen atom, may form a saturated or unsaturated cyclic amino group that may have, in the ring structure, 1 or 2 heteroatoms selected from the group consisting of nitrogen, oxygen, and sulfur, in addition to the adjacent nitrogen atom; and one of $R^3$ and $R^4$ is hydrogen or $C_{1-6}$ alkyl, and the other is hydrogen, hydroxy, $C_{1-6}$ alkyl that may have one or more substituents, $C_{1-6}$ alkoxy that may have one or more substituents, amino, mono- or di($C_1$-$C_6$ alkyl)amino that may have one or more substituents, $C_{6-14}$ aryl that may have one or more substituents, or a monocyclic or bicyclic, saturated or unsaturated heterocyclic group that may have one or more substituents, or $R^3$ and $R^4$, taken together with the adjacent nitrogen atom, may form a saturated or unsaturated cyclic amino group that may have, in the ring structure, one heteroatom selected from the group consisting of nitrogen, oxygen, and sulfur, in addition to the adjacent nitrogen atom, the cyclic amino group optionally having 1 to 3 substituents selected from the group consisting of halogen, hydroxy, cyano, nitro, formyl, carboxy, $C_{1-6}$ alkyl that may have one or more substituents, $C_{6-14}$ aryl that may have one or more substituents, ($C_1$-$C_6$ alkoxy)carbonyl that may have one or more substituents, and mono- or di($C_1$-$C_6$ alkyl)aminocarbonyl that may have one or more substituents.

5. The benzimidazole compound or salt thereof according to claim 1, wherein:

$X^1$ is carbonyl;

$R^1$ is a pyrrole ring having 1 to 3 substituents as well as a hydrogen atom bonded to the nitrogen atom, and the substituents attached to the pyrrole ring are selected from the group consisting of halogen, cyano, nitro, $C_{1-6}$ alkyl that may have one or more substituents selected from the group consisting of halogen, hydroxy, dimethylamino, and pyrrolidinyl, ethenyl that may have one substituent selected from the group consisting of cyano, carboxy, and ($C_1$-$C_6$ alkoxy)carbonyl, and —(C=O)—$R^2$;

$R^2$ is hydrogen, hydroxy, $C_{1-6}$ alkoxy, or —$NR^3R^4$; and one of $R^3$ and $R^4$ is hydrogen or $C_{1-6}$ alkyl, and the other is hydrogen, hydroxy, $C_{1-3}$ alkyl that may have one or more substituents, $C_{1-3}$ alkoxy that may have one or more substituents, phenyl that may have one or more substituents, or a heterocyclic group selected from the group consisting of morpholino, isoxazolyl, indolyl, methylenedioxyphenyl, ethylenedioxyphenyl, dihydrobenzofuranyl, and benzothiazolyl [the heterocyclic group may have one or more substituents], or $R^3$ and $R^4$, taken together with the adjacent nitrogen atom, may form a saturated or unsaturated cyclic amino group that may have, in the ring structure, one heteroatom selected from nitrogen and oxygen, in addition to the adjacent nitrogen atom.

6. The benzimidazole compound or salt thereof according to claim 1, wherein:

$X^1$ is carbonyl;

$R^1$ is a pyrrole ring having 2 or 3 substituents as well as a hydrogen atom bonded to the nitrogen atom, the substituents on two carbon atoms of the pyrrole ring being $C_{1-6}$ alkyl, and the remaining carbon atom having a hydrogen atom bonded thereto or cyano or —(C=O)—$R^2$ as a substituent bonded thereto;

$R^2$ is hydroxy, $C_{1-3}$ alkoxy, or —$NR^3R^4$; and one of $R^3$ and $R^4$ is hydrogen or $C_{1-3}$ alkyl, and the other is hydrogen, hydroxy, $C_{1-3}$ alkyl that may have one or more substituents, $C_{1-3}$ alkoxy that may have one or more substituents, phenyl that may have 1 to 3 substituents selected from the group consisting of halogen, cyano, and $C_{1-6}$ alkoxy, morpholino, isoxazolyl, indolyl, methylenedioxyphenyl, ethylenedioxyphenyl, dihydrobenzofuranyl, or benzothiazolyl, or —$NR^3R^4$ is pyrrolidinyl, thiazolidinyl, pyrazolinyl, morpholino, or piperazinyl.

7. The benzimidazole compound or salt thereof according to claim 1, wherein:

$X^1$ is carbonyl;

$R^1$ is a pyrrole ring that has three substituents as well as a hydrogen atom bonded to the nitrogen atom and that is attached to the benzimidazole ring at the 4-position, and of the substituents on pyrrole ring, substituents at the 3- and the 5-positions are $C_{1-3}$ alkyl, and the substituent at the 2-position is cyano or —(C=O)—$R^2$;

$R^2$ is hydroxy, ethoxy, or —$NR^3R^4$; and one of $R^3$ and $R^4$ is hydrogen or $C_{1-3}$ alkyl, and the other is hydrogen, hydroxy, $C_{1-3}$ alkyl that may have one or more substituents, $C_{1-3}$ alkoxy that may have one or more substituents, or phenyl that may have 1 to 3 substituents selected from the group consisting of halogen, cyano, and $C_{1-3}$ alkoxy, or —$NR^3R^4$ is pyrrolidinyl, pyrazolinyl, or morpholino.

8. The benzimidazole compound or salt thereof according to claim 1, wherein:

X¹ is carbonyl;

R¹ is a pyrrole ring that has three substituents, as well as a hydrogen atom bonded to the nitrogen atom, and that is attached to the benzimidazole ring at the 4-position, and of the substituents on the pyrrole ring, the substituents at the 3- and 5-positions are methyl, and the substituent at the 2-position is —(C=O)—R²;

R² is hydroxy, ethoxy, or —NR³R⁴; and one of R³ and R⁴ is hydrogen or $C_{1-3}$ alkyl, and the other is $C_{1-3}$ alkyl that may have one or more substituents, or $C_{1-3}$ alkoxy, or —NR³R⁴ is pyrrolidinyl or morpholino.

9. The benzimidazole compound or salt thereof according to claim 1, which is:
- 4-(5-benzoylbenzimidazol-2-yl)-3,5-dimethylpyrrole-2-carboxylic acid,
- 2-(2-cyano-3,5-dimethyl-pyrrol-4-yl)-5-benzoylbenzimidazole,
- N-(methoxy)-4-(5-benzoylbenzimidazol-2-yl)-3,5-dimethylpyrrole- 2-carboxamide,
- (N-methoxy-N-methyl)-4-(5-benzoylbenzimidazol-2-yl)-3,5-dimethylpyrrole-2-carboxamide,
- N-(3-dimethylaminopropyl)-4-(5-benzoylbenzimidazol-2-yl)-3,5-dimethylpyrrole-2-carboxamide,
- N-(2-(2-pyridyl)ethyl)-4-(5-benzoylbenzimidazol-2-yl)-3,5-dimethylpyrrole-2-carboxamide,
- ((4-(5-benzoylbenzimidazol-2-yl)-3,5-dimethylpyrrol-2-yl)carbonyl)morpholine,
- ((4-(5-benzoylbenzimidazol-2-yl)-3,5-dimethylpyrrol-2-yl)carbonyl)pyrazoline, or
- (N,N-dimethyl)-4-(5-benzoylbenzimidazol-2-yl)-3,5-dimethylpyrrole-2-carboxamide.

10. A pharmaceutical composition comprising an effective amount of the compound according to claim 1 or a pharmaceutically acceptable salt thereof, and a pharmaceutically acceptable carrier.

11. A method for treating diseases in which prostaglandin D2 or metabolites thereof participates, the method comprising administering, to a patient, an effective amount of the compound according to claim 1 or a pharmaceutically acceptable salt thereof, wherein the disease in which prostaglandin D2 or metabolites thereof participate is at least one disease selected from the group consisting of nasal congestion, pollinosis, allergic rhinitis, and sinusitis.

12. A method for inhibiting the production of prostaglandin D2 synthetase comprising administering an effective amount of the compound according to claim 1 or a pharmaceutically acceptable salt thereof, and a pharmaceutically acceptable carrier to a patient in need of such treatment.

* * * * *